US007414057B2

(12) United States Patent
Bakshi et al.

(10) Patent No.: US 7,414,057 B2
(45) Date of Patent: Aug. 19, 2008

(54) PIPERAZINE UREA DERIVATIVES AS MELANOCORTIN-4 RECEPTOR AGONISTS

(75) Inventors: Raman Kumar Bakshi, Edison, NJ (US); Ravi P. Nargund, East Brunswick, NJ (US); Brenda L. Palucki, Hillsborough, NJ (US); Min K. Park, Whippany, NJ (US); Zhixiong Ye, Princeton, NJ (US)

(73) Assignee: Merck & Co., Inc., Rahway, NJ (US)

( * ) Notice: Subject to any disclaimer, the term of this patent is extended or adjusted under 35 U.S.C. 154(b) by 440 days.

(21) Appl. No.: 10/526,178

(22) PCT Filed: Sep. 5, 2003

(86) PCT No.: PCT/US03/27892

§ 371 (c)(1),
(2), (4) Date: Feb. 28, 2005

(87) PCT Pub. No.: WO2004/024720

PCT Pub. Date: Mar. 25, 2004

(65) Prior Publication Data
US 2006/0040906 A1 Feb. 23, 2006

Related U.S. Application Data

(60) Provisional application No. 60/409,879, filed on Sep. 11, 2002.

(51) Int. Cl.
C07D 401/12 (2006.01)
C07D 403/12 (2006.01)
A61K 31/453 (2006.01)
A61K 31/4545 (2006.01)
A61P 3/04 (2006.01)
A61P 3/10 (2006.01)

(52) U.S. Cl. .................. 514/252.13; 544/360
(58) Field of Classification Search ........... 544/360; 514/252.13
See application file for complete search history.

(56) References Cited

U.S. PATENT DOCUMENTS

| 5,576,290 | A | 11/1996 | Hadley | |
|---|---|---|---|---|
| 5,721,250 | A | * | 2/1998 | Morriello et al. ......... 514/318 |
| 5,936,089 | A | | 8/1999 | Carpino et al. |
| 6,051,555 | A | | 4/2000 | Hadley |
| 6,166,037 | A | | 12/2000 | Budhu et al. |
| 6,294,534 | B1 | | 9/2001 | Nargund et al. |
| 6,344,449 | B1 | * | 2/2002 | Rudolf et al. ......... 514/211.05 |
| 6,350,760 | B1 | | 2/2002 | Bakshi et al. |
| 6,458,790 | B2 | | 10/2002 | Palucki et al. |

FOREIGN PATENT DOCUMENTS

| DE | 197 13 000 | 10/1998 |
|---|---|---|
| WO | WO 96/35713 | 11/1996 |
| WO | WO 96/38471 | 12/1996 |
| WO | WO 99/09984 | 3/1999 |
| WO | WO 99/64002 | 12/1999 |
| WO | WO 00/74649 | 12/2000 |
| WO | WO 01/58891 | 8/2001 |
| WO | WO 01/70337 | 9/2001 |
| WO | WO 01/70708 | 9/2001 |
| WO | WO 01/91752 | 12/2001 |
| WO | WO 02/15909 | 2/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/068387 | 9/2002 |
| WO | WO 02/068388 | 9/2002 |
| WO | WO 02/070511 | 9/2002 |
| WO | WO 03/007949 | 1/2003 |
| WO | WO 03/009847 | 2/2003 |
| WO | WO 03/031410 | 4/2003 |

OTHER PUBLICATIONS

Cody et al., Hum. Genet., 105:426-427, 1999.*
Schioth et al., Regulatory Peptides, 106, 7-12, 2002.*
Rudolf et al., CA 128:197358, 1998.*
Wessells et al., J. of Urology, vol. 160(2), (1998), pp. 389-393, "Synthetic melanotropic peptide initiates erections in men with psychogenic erectile dysfunction . . . ".
Giraudo et al., Brain Research, vol. 809 (1998), pp. 302-306, "Feeding effects of hypothalamic injection of melanocortin 4 receptor ligands".
Chen et al., Cell, vol. 91 (1997), pp. 789-798, "Exocrine gland dysfunction in MC5-R-deficient mice: . . . ".
Chaki et al., Exp. Opin. Ther. Patents (2001), vol. 11(11), pp. 1677-1692, "Recent advances in feeding suppressing agents: Potential therapeutic strategy for the treatment of obesity".
Dorr et al., Life Sciences, vol. 58 (1996), pp. 1777-1784, "Evaluation of melanotan-II, a superpotent cyclic melanotropic peptide in a pilot phase-I clinical study".
Kask et al., Biochem. & Biophys. Res. Comm., vol. 245 (1998), pp. 90-93, "Selective antagonist for the melanocortin 4 receptor (HS014) increases food intake in free-feeding rats".
Huszar et al., Cell, vol. 88 (1997), pp. 131-141, "Targeted disruption of the melanocortin-4 receptor results in obesity in mice".
Wikberg et al., Pharma., vol. 42 (2000), pp. 393-420, "New aspects on the melanocortins and their receptors".
Wikberg et al., Exp. Op. Ther. Patents, vol 11 (2001), pp. 61-76, "Melanocortin receptors: New opportunities in drug discovery".
Anderssson, Exp. Op. Ther. Patents, vol. 11 (2001), pp. 1583-1592, "Ligands to the melanocortin receptors".
Peptides: Frontiers of Peptide Science, Fifteenth American Peptide Symposium, Jun. 14-19, 1997 (Nashville, TN).
Corcos et al., Society for Neuroscience, vol. 23 (1997), Abstract 267.9, "HP 228 is a potent agonist of melanocortin receptor 4, and significantly attenuates obesity and diabetes in Zucker fatty rats".
Marsh, Nat. Genet., vol. 21 (1999), pp. 119-122, "Response of melanocortin-4 receptor-deficient mice to anorectic and orexigenic peptides".

* cited by examiner

Primary Examiner—Venkataraman Balasubram
(74) Attorney, Agent, or Firm—Richard C. Billups; Baerbel R. Brown; Catherine D. Fitch

(57) ABSTRACT

Certain novel piperazine urea derivatives are agonists of the human melanocortin-4 receptor (MC-4R) and, in particular, are receptor-subtype selective agonists of MC-4R. They are useful for the treatment, control, or prevention of diseases and disorders responsive to the activation of MC-4R, such as obesity and diabetes.

26 Claims, No Drawings

PIPERAZINE UREA DERIVATIVES AS MELANOCORTIN-4 RECEPTOR AGONISTS

CROSS-REFERENCE TO RELATED APPLICATIONS

This application is a U.S. National Phase application under 35 U.S.C. §371 of PCT Application No. PCT/US03/27892, filed Sep. 5, 2003, which claims priority under 35 U.S.C. §119 from U.S. Provisional Application No. 60/409,879, filed Sep. 11, 2002.

FIELD OF THE INVENTION

The present invention relates to piperazine urea derivatives, their synthesis, and their use as melanocortin-4 receptor (MC-4R) agonists. More particularly, the compounds of the present invention are receptor-subtype selective partial agonists of the melanocortin-4 receptor (MC-4R) and are useful for the treatment, control, or prevention of disorders responsive to partial activation of MC-4R, such as obesity and diabetes.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feeding behavior (S. Q. Giraudo et al., "Feeding effects of hypothalamic injection of melanocortin-4 receptor ligands," *Brain Research*, 80: 302-306 (1998)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," *Biochem. Biophys. Res. Commun.*, 245: 90-93 (1998)). MC-5R is expressed in many tissues, including white fat, placenta and exocrine glands. A low level of expression is also observed in the brain. MC-5R knockout mice reveal reduced sebaceous gland lipid production (Chen et al., *Cell*, 91: 789-798 (1997)).

Evidence for the involvement of MC-R's in obesity includes: i) the agouti ($A^{vy}$) mouse which ectopically expresses an antagonist of the MC-1R, MC-3R and MC-4R is obese, indicating that blocking the action of these three MC-R's can lead to hyperphagia and metabolic disorders; ii) MC-4R knockout mice (D. Huszar et al., *Cell*, 88: 131-141 (1997)) recapitulate the phenotype of the agouti mouse and these mice are obese; iii) the cyclic heptapeptide MT-II (a non-selective MC-1R, -3R, -4R, and -5R agonist), when injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," *Society for Neuroscience Abstracts*, 23: 673 (1997)). The appetite suppressing effect of MT-II is no longer observed in mice lacking the MC-4R (D. J. Marsh, et al., "Response of melanocortin-4 receptor-deficient mice to anorectic and orexigenic peptides," *Nat. Genet.*, 21: 119-122 (1999)).

Based on the above observations, the melanocortin system in the brain is thought to play a crucial role in regulating feeding and energy balance and that MC-4R agonists are considered to be useful for the treatment of obesity. Reference is made to the following publications for a discussion of the involvement of the MC-4R in the central regulation of feeding behavior and body weight and the potential of MC-4R agonists for the treatment of obesity: (1) J. Wikberg, et al., "New aspects of the melanocortins and their receptors," *Pharmacological Res.*, 42: 393-420 (2000); (2) J. Wikberg, "Melanocortin receptors: new opportunities in drug discovery," *Exp. Opin. Ther. Patents*, 11: 61-76 (2001); (3) P. M. Andersson, et al., "Ligands to the melanocortin receptors," *Exp. Opin. Ther. Patents*, 11: 1583-1592 (2001); (4) S. Chaki and A. Nakazato, "Recent advances in feeding suppressing agents: potential therapeutic strategy for the treatment of obesity," *Exp. Opin. Ther. Patents*, 11: 1677-1692 (2001).

Melanocortin receptor involvement in male and female sexual dysfunction has also been reported. Erectile dysfunction denotes the medical condition of inability to achieve penile erection sufficient for successful sexual intercourse. The term "impotence" is oftentimes employed to describe this prevalent-condition. Synthetic melanocortin receptor agonists (melanotropic peptides) have been found to initiate erections in men with psychogenic erectile dysfunction [See H. Wessells et al., "Synthetic Melanotropic Peptide Initiates Erections in Men With_Psychogenic Erectile Dysfunction: Double-Blind, Placebo Controlled Crossover Study," J. Urol., 160: 389-393 (1998); Fifteenth American Peptide Symposium, Jun. 14-19, 1997 (Nashville Tenn.)]. In the above study, the centrally acting α-melanocyte-stimulating hormone analog, melanotan-II (M-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH$_2$, which contains the 4-10 melanocortin receptor binding region common to α-MSH and adrenocorticotropin, but with a lactam bridge. It is a non-selective MC-1R, -3R, -4R, and -5R agonist (Dorr et al., Life Sciences, Vol. 58, 1777-1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response.

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine and piperidine derivatives have been disclosed in WO 99/64002 (16 Dec. 1999); WO 00/74679 (14 Dec. 2000); WO 01/70708 (27 Sep. 2001); WO 01/70337 (27 Sep. 2001); WO 01/91752 (6 Dec. 2001); WO 02/15909 (28

Feb. 2002); WO 02/59095 (1 Aug. 2002); U.S. Pat. No. 6,294, 534 (25 Sep. 2001); U.S. Pat. No. 6,350,760 (26 Feb. 2002) and U.S. Pat. No. 6,458,790 (1 Oct. 2002) as agonists of the melanocortin receptor(s) and particularly as selective agonists of the MC-4R receptor and their utility for the treatment of obesity and diabetes, and sexual dysfunction, including erectile dysfunction and female sexual dysfunction. Analogous piperazine and piperidine derivatives as melanocortin receptor agonists for the treatment of obesity and diabetes have been disclosed in WO 02/59107 (1 Aug. 2002); WO 02/59108 (1 Aug. 2002); and WO 02/59117 (1 Aug. 2002); and WO 02/068387 (6 Sep. 2002); WO 02/068388 (6 Sep. 2002); WO 03/007949 (30 Jan. 2003); WO 03/009847 (6 Feb. 2003); and WO 03/31410.

There exists a continuing need for potent and receptor-subtype selective MC-4R agonists with improved pharmacodynamnic and pharmacokinetic properties for the treatment, control, or prevention of obesity and diabetes. In particular, there is a need for potent and receptor-subtype selective MC-4R agonists useful for the treatment, control, or prevention of obesity and diabetes, but with diminished erectogenic properties.

It is therefore an object of the present invention to provide piperazine urea derivatives which are melanocortin-4 receptor (MC-4R) agonists useful for the treatment, control, or prevention of obesity and diabetes.

It is another object of the present invention to provide piperazine urea derivatives which are receptor-subtype selective agonists of the melanocortin-4 (MC-4R) receptor.

It is another object of the present invention to provide piperazine urea derivatives which are receptor-subtype selective partial agonists of the melanocortin-4 (MC-4R) receptor.

It is another object of the present invention to provide pharmaceutical compositions comprising the melanocortin-4 receptor agonists of the present invention with a pharmaceutically acceptable carrier.

It is another object of the present invention to provide methods for the treatment or prevention of disorders, diseases, or conditions responsive to the activation of the melanocortin-4 receptor in a subject in need thereof by administering the compounds and pharmaceutical compositions of the present invention.

It is another object of the present invention to provide methods for the treatment, control, or prevention of obesity and diabetes mellitus by administering the compounds and pharmaceutical compositions of the present invention to a subject in need thereof.

These and other objects will become readily apparent from the detailed description that follows.

SUMMARY OF THE INVENTION

The present invention relates to piperazine urea derivatives of structural formula I:

(I)

These piperazine urea derivatives are effective as melanocortin-4 receptor agonists and are particularly effective as receptor-subtype selective melanocortin-4 receptor (MC-4R) partial agonists. They are useful for the treatment, control or prevention of disorders responsive to the activation of MC-4R, such as obesity and diabetes.

The present invention also relates to pharmaceutical compositions comprising the compounds of the present invention and a pharmaceutically acceptable carrier.

The present invention also relates to methods for the treatment, control, or prevention of disorders, diseases, or conditions responsive to the activation of the melanocortin-4 receptor in a subject in need thereof by administering the compounds and pharmaceutical compositions of the present invention.

The present invention also relates to methods for the treatment, control, or prevention of obesity and diabetes mellitus by administering the compounds and pharmaceutical compositions of the present invention.

The present invention also relates to methods for treating or preventing obesity by administering the compounds of the present invention in combination with a therapeutically effective amount of another agent known to be useful to treat or prevent the condition.

The present invention also relates to methods for treating or preventing diabetes by administering the compounds of the present invention in combination with a therapeutically effective amount of another agent known to be useful to treat or prevent the condition.

DETAILED DESCRIPTION OF THE INVENTION

The present invention relates to piperazine urea derivatives useful as melanocortin-4 receptor agonists, in particular, as receptor-subtype selective MC-4R partial agonists. Compounds of the present invention are described by structural formula I:

(I)

or a pharmaceutically acceptable salt thereof; wherein m is 1 or 2;

each p is independently 0, 1, or 2;

each n is independently 0, 1, or 2;

$R^1$ is selected from the group consisting of hydrogen, $C_{1-8}$ alkyl, $(CHR^{12})_n$—$C_{3-6}$ cycloalkyl, $(CHR^{12})_n$—$O(CHR^{12})$aryl, $(CHR^{12})_n$-aryl, and $(CHR^{12})_n$-heteroaryl;

in which aryl and heteroaryl are unsubstituted or substituted with one to three groups independently selected from $R^{11}$; and alkyl and cycloalkyl are unsubstituted or substituted with one to three groups independently selected from $R^{11}$ and oxo;

$R^3$, $R^4$, $R^5$, $R^6$, $R^7$, $R^8$, $R^9$, and $R^{10}$ are each independently selected from the group consisting of
hydrogen,
$C_{1-8}$ alkyl,
$(CH_2)_n$-aryl,
$(CH_2)_n C_{3-6}$ cycloalkyl,
$(CH_2)_n$-heteroaryl, and
$(CH_2)_n$-heterocyclyl;

in which aryl and heteroaryl are unsubstituted or substituted with one to three groups independently selected from $R^{11}$; and alkyl, cycloalkyl, and heterocyclyl are unsubstituted or substituted with one to three groups independently selected from $R^{11}$ and oxo;

or $R^3$ and $R^5$ and the carbon atoms to which they are attached form a 5- to 7-membered ring;
or $R^3$ and $R^9$ and the carbon atoms to which they are attached form a 5- to 7-membered ring;
or $R^5$ and $R^7$ and the carbon atoms to which they are attached form a 5- to 7-membered ring;
or $R^7$ and $R^9$ and the carbon atoms to which they are attached form a 5- to 7-membered ring;

$R^2$ is selected from the group consisting of
hydrogen,
$C_{1-8}$ alkyl,
$C_{2-6}$ alkenyl,
$(CH_2)_n$-aryl,
$(CH_2)_n C_{3-6}$ cycloalkyl,
$(CH_2)_n$-heteroaryl,
$(CH_2)_n$-heterocyclyl,
$(CH_2)_{1-2}OR^{12}$,
$(CH_2)_{1-2}CO_2R^{12}$,
$(CH_2)_{1-2}CONR^{12}R^{12}$,
$CH_2C\equiv CH$, and
$CH_2CHF_2$;

in which aryl and heteroaryl are unsubstituted or substituted with one to three groups independently selected from $R^{11}$; and alkyl, cycloalkyl, and heterocyclyl are unsubstituted or substituted with one to three groups independently selected from $R^{11}$ and oxo;

or $R^2$ and $R^3$ and the carbon atoms to which they are attached form a 5- to 7-membered ring;
or $R^3$ and $R^4$ and the carbon atom to which they are attached form a 3- to 6-membered spirocyclic ring;

$R^{11}$ is selected from the group consisting of
hydrogen,
$C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_n C_{3-7}$ cycloalkyl,
halogen,
$OR^{12}$,
$(CH_2)_n N(R^{12})_2$,
$(CH_2)_n C\equiv N$,
$(CH_2)_n CO_2R^{12}$,
$NO_2$,
$(CH_2)_n NR^{12}SO_2R^{12}$,
$(CH_2)_n SO_2N(R^{12})_2$,
$(CH_2)_n S(O)_p R^{12}$,
$(CH_2)_n NR^{12}C(O)N(R^{12})_2$,
$(CH_2)_n C(O)N(R^{12})_2$,
$(CH_2)_n NR^{12}C(O)R^{12}$,
$(CH_2)_n NR^{12}CO_2R^{12}$,
$O(CH_2)_n C(O)N(R^{12})_2$,
$CF_3$,
$CH_2CF_3$,
$OCF_3$, and
$OCH_2CF_3$;

wherein phenyl, naphthyl, heteroaryl, cycloalkyl, and heterocyclyl are unsubstituted or substituted with one to three substituents independently selected from halogen, hydroxy, $C_{1-4}$ alkyl, trifluoromethyl, and $C_{1-4}$ alkoxy; and wherein any methylene ($CH_2$) carbon atom in $R^{11}$ is unsubstituted or substituted with one to two groups independently selected from halogen, hydroxy, and $C_{1-4}$ alkyl; or two substituents when on the same methylene ($CH_2$) carbon atom are taken together with the carbon atom to which they are attached to form a cyclopropyl group;

each $R^{12}$ is independently selected from the group consisting of
hydrogen,
$C_{1-8}$ alkyl,
$(CH_2)_n$-phenyl,
$(CH_2)_n$-naphthyl,
$(CH_2)_n$-heteroaryl, and
$(CH_2)_n C_{3-7}$ cycloalkyl;

wherein any methylene ($CH_2$) carbon atom in $R^{12}$ is unsubstituted or substituted with one to two groups independently selected from halogen, hydroxy, and $C_{1-4}$ alkyl; or two $R^{12}$ groups together with the atom to which they are attached form a 5- to 8-membered mono- or bicyclic ring system optionally containing an additional heteroatom selected from O, S, and $NC_{1-4}$ alkyl;

each $R^{13}$ is independently selected from the group consisting of
hydrogen,
$C_{1-8}$ alkyl,
$(CH_2)_n$-aryl,
$(CH_2)_n$-heteroaryl,
$(CH_2)_n$-heterocyclyl, and
$(CH_2)_n C_{3-7}$ cycloalkyl;

wherein alkyl, aryl, heteroaryl, heterocyclyl, and cycloalkyl are unsubstituted or substituted with one to three groups independently selected from halogen, hydroxy, $C_{1-3}$ alkoxy, $C_{1-3}$ alkylthio, carboxy, $C_{1-4}$ alkyloxycarbonyl, amino, $C_{1-4}$ alkylamino, and di($C_{1-4}$ alkylamino);

or two $R^{13}$ groups together with the atoms to which they are attached form a 5- to 8-membered mono- or bi-cyclic ring system optionally containing an additional heteroatom selected from O, S, $NR^{12}$, NBoc, and NCbz;

X is selected from the group consisting of
$C_{1-8}$ alkyl,
$(CH_2)_n C_{3-8}$ cycloalkyl,
$(CH_2)_n$-phenyl,
$(CH_2)_n$-naphthyl,
$(CH_2)_n$-heteroaryl,
$(CH_2)_n$-heterocyclyl,
$(CH_2)_n C\equiv N$,
$(CH_2)_n CON(R^{13}R^{13})$,
$(CH_2)_n CO_2R^{13}$,
$(CH_2)_n COR^{13}$,
$(CH_2)_n NR^{13}C(O)R^{13}$,
$(CH_2)_n NR^{13}CO_2R^{13}$,
$(CH_2)_n NR^{13}C(O)N(R^{13})_2$,
$(CH_2)_n NR^{13}SO_2R^{13}$,
$(CH_2)_n S(O)_p R^{13}$, $(CH_2)_nSO_2N(R^{13})(R^{13})$,
$(CH_2)_nOR^{13}$,
$(CH_2)_nOC(O)R^{13}$,
$(CH_2)_nOC(O)OR^{13}$,
$(CH_2)_nOC(O)N(R^{13})_2$,
$(CH_2)_nN(R^{13})(R^{13})$, and
$(CH_2)_nNR^{13}SO_2N(R^{13})(R^{13})$;

wherein phenyl, naphthyl, and heteroaryl are unsubstituted or substituted with one to three groups independently selected from $R^{11}$; alkyl, cycloalkyl, and heterocyclyl are unsubstituted or substituted with one to three groups independently selected from $R^{11}$ and oxo; and wherein any methylene ($CH_2$) carbon atom in X is unsubstituted or substituted with one to two groups independently selected from halogen, hydroxy, and $C_{1-4}$ alkyl; and Y is selected from the group consisting of hydrogen,
$C_{1-8}$ alkyl,
$C_{2-6}$ alkenyl,
$(CH_2)_nC_{3-8}$ cycloalkyl,
$(CH_2)_n$-phenyl,
$(CH_2)_n$-naphthyl,
$(CH_2)_n$-heteroaryl, and
$(CH_2)_n$-heterocyclyl;

wherein phenyl, naphthyl, and heteroaryl are unsubstituted or substituted with one to three groups independently selected from $R^{11}$; alkyl, cycloalkyl, and heterocyclyl are unsubstituted or substituted with one to three groups independently selected from $R^{11}$ and oxo; and wherein any methylene ($CH_2$) carbon atom in Y is unsubstituted or substituted with one to two groups independently selected from halogen, hydroxy, and $C_{1-4}$ alkyl.

In one embodiment of the compounds of structural formula I, $R^1$ is $CHR^{12}$-aryl, $CHR^{12}OCHR^{12}$-aryl, or $CHR^{12}$-heteroaryl wherein aryl and heteroaryl are unsubstituted or substituted with one to two groups independently selected from $R^{11}$. In a class of this embodiment, $R^1$ is benzyl optionally substituted with one or two groups independently selected from halogen, $C_{1-4}$ alkyl, $C_{1-4}$ alkoxy, CN, $CF_3$, and $OCF_3$. In a subclass of this class, $R^1$ is 4-chlorobenzyl; 4-fluorobenzyl; 3,4-difluorobenzyl; 3,5-difluorobenzyl; 2-cyano-4-fluorobenzyl; or 4-methoxybenzyl.

In a second embodiment of compounds of formula I, $R^2$ is selected from the group consisting of
hydrogen,
$C_{1-8}$ alkyl,
$CH_2$-aryl,
$CH_2$-heteroaryl,
$CH_2$-heterocyclyl,
$CH_2C_{3-6}$ cycloalkyl,
$CH_2CO_2R^{12}$,
$CH_2CONR^{12}R^{12}$,
$CH_2OR^{12}$,
$CH_2C\equiv CH$, and
$CH_2CHF_2$;

wherein aryl and heteroaryl are unsubstituted or substituted with one to three groups independently selected from $R_{11}$; and alkyl, cycloalkyl, and heterocyclyl are unsubstituted or substituted with one to three groups independently selected from $R^{11}$ and oxo. In a class of this embodiment, $R^2$ is hydrogen or $C_{1-4}$ alkyl. In a subclass of this class, $R^2$ is hydrogen.

In a third embodiment of the compounds of structural formula I, X is selected from the group consisting of $C_{1-6}$ alkyl, $(CH_2)_n$-phenyl, $(CH_2)_n$-naphthyl, $(CH_2)_n$-heteroaryl, $(CH_2)_n$-heterocyclyl, $(CH_2)_nC(O)N(R^{13})(R^{13})$, $(CH_2)_nCO_2R^{13}$, $(CH_2)_nS(O)_pR^{13}$, $(CH_2)_nOR^{13}$, $(CH_2)_nNR^{13}C(O)R^{13}$, and $(CH_2)_nNR^{13}SO_2R^{13}$; wherein phenyl, naphthyl, and heteroaryl are unsubstituted or substituted with one to three groups independently selected from $R^{11}$; alkyl and heterocyclyl are unsubstituted or substituted with one to three groups independently selected from $R^{11}$ and oxo; and the $(CH_2)_n$ group is unsubstituted or substituted with one to three groups independently selected from $R^{12}$, halogen, $S(O)_pR^{12}$, $N(R^{12})_2$, and $OR^{12}$.

In a class of this third embodiment, X is selected from the group consisting of $C_{1-6}$ alkyl, $(CH_2)_{0-1}$-phenyl, $(CH_2)_{0-1}$-heteroaryl, $(CH_2)_{0-1}$-heterocyclyl, $(CH_2)_{0-1}NHC(O)R^{13}$, $(CH_2)_{0-1}CO_2R^{13}$, and $(CH_2)_{0-1}C(O)N(R^{13})(R^{13})$; wherein phenyl and heteroaryl are unsubstituted or substituted with one to three groups independently selected from $R^{11}$; and alkyl and heterocyclyl are unsubstituted or substituted with one to three groups independently selected from $R^{11}$ and oxo. In a subclass of this class, heteroaryl is selected from the group consisting of pyridyl, pyrazinyl, pyrimidinyl, triazolyl, tetrazolyl, thiadiazolyl, oxadiazolyl, pyrazolyl, and imidazolyl.

In a fourth embodiment of the compounds of structural formula I, Y is $C_{1-8}$ alkyl, $(CH_2)_nC_{3-7}$ cycloallyl, $(CH_2)_n$-aryl, $(CH_2)_n$-heterocyclyl, or $(CH_2)_n$-heteroaryl; wherein aryl and heteroaryl are unsubstituted or substituted with one to three groups independently selected from $R^{11}$; and $(CH_2)_n$, alkyl, cycloalkyl, and heterocyclyl are unsubstituted or substituted with one to three groups independently selected from $R^{11}$ and oxo. In a class of this embodiment, Y is $C_{3-6}$ cycloalkyl or $C_{1-6}$ alkyl, wherein alkyl and cycloallyl are unsubstituted or substituted with one to three groups independently selected from $R^{11}$ and oxo. In a subclass of this class, Y is cyclohexyl or $C_{1-6}$ alkyl, wherein the cyclohexyl and alkyl groups are unsubstituted or substituted with one to three groups independently selected from $R^{11}$ and oxo.

In a fifth embodiment of the compounds of structural formula I, m is 1.

In a sixth embodiment of the compounds of structural formula I, $R^3$, $R^4$, $R^5$, $R^6$, $R^7$, $R^8$, $R^9$, and $R^{10}$ are each independently hydrogen or $C_{1-4}$ alkyl; or $R^3$ and $R^5$ and the carbon atoms to which they are attached form a 5- to 7-membered ring; or $R^3$ and $R^9$ and the carbon atoms to which they are attached form a 5- to 7-membered ring. In a class of this embodiment, $R^3$, $R^4$, $R^5$, and $R^6$ are each independently hydrogen or $C_{1-4}$ alkyl, and $R^7$, $R^8$, $R^9$, and $R^{10}$ are hydrogen. In a subclass of this class, $R^3$ and $R^5$ are each independently hydrogen or $C_{1-4}$ alkyl, and $R^4$ and $R^6$ hydrogen.

In a seventh embodiment of the compounds of structural formula I, at least one of $R^3$, $R^4$, $R^5$, $R^6$, $R^7$, $R^8$, $R^9$ and $R^{10}$ is $C_{1-4}$ alkyl.

In yet a further embodiment of the present invention, there are provided compounds of structural formula II:

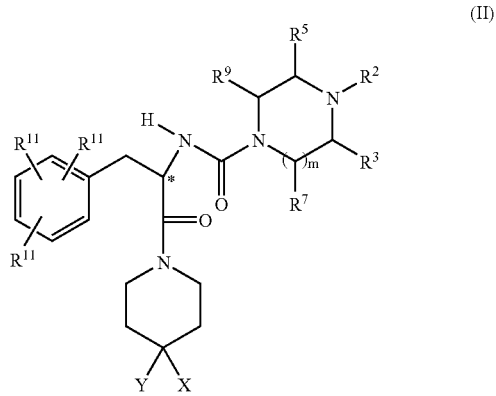

(II)

wherein m is 1 or 2;
each $R^{11}$ is independently selected from the group consisting of
hydrogen,
halogen,
cyano,
$C_{1-4}$ alkyl,
$C_{1-4}$ alkoxy,
$C_{1-4}$ alkylthio,
trifluoromethyl, and
trifluoromethoxy;
$R^2$ is hydrogen or $C_{1-4}$ alkyl, unsubstituted or substituted with one to three groups independently selected from $R^{11}$ and oxo;
$R^3$, $R^5$, $R^7$, and $R^9$ are each independently hydrogen or $C_{1-4}$ alkyl; or $R^3$ and $R^5$ and the carbon atoms to which they are attached form a 5- to 7-membered ring; or $R^3$ and $R^9$ and the carbon atoms to which they are attached form a 5- to 7-membered ring;
Y is $C_{5-7}$ cycloalkyl or $C_{1-6}$ alkyl, wherein alkyl and cycloalkyl are unsubstituted or substituted with one to three groups independently selected from $R^{11}$ and oxo; and
X is selected from the group consisting of

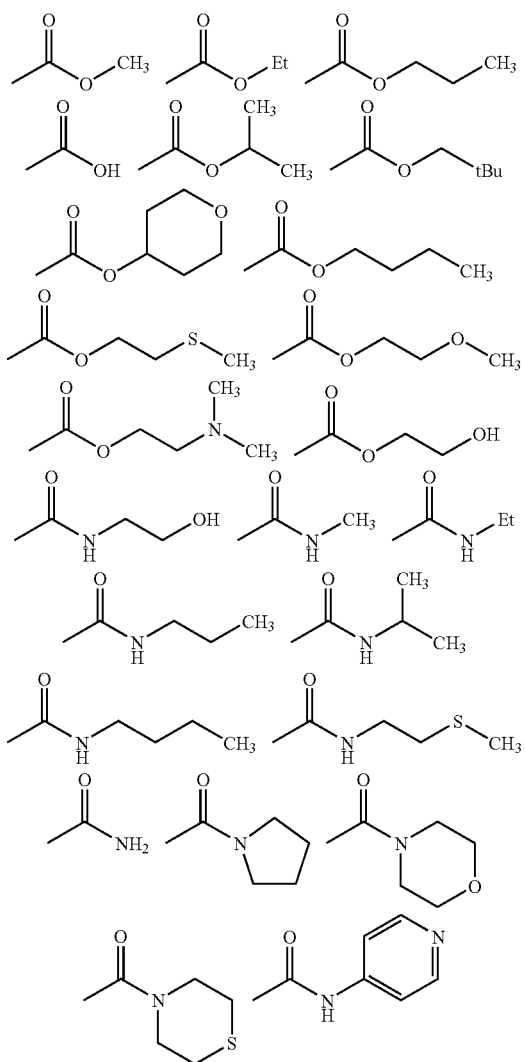

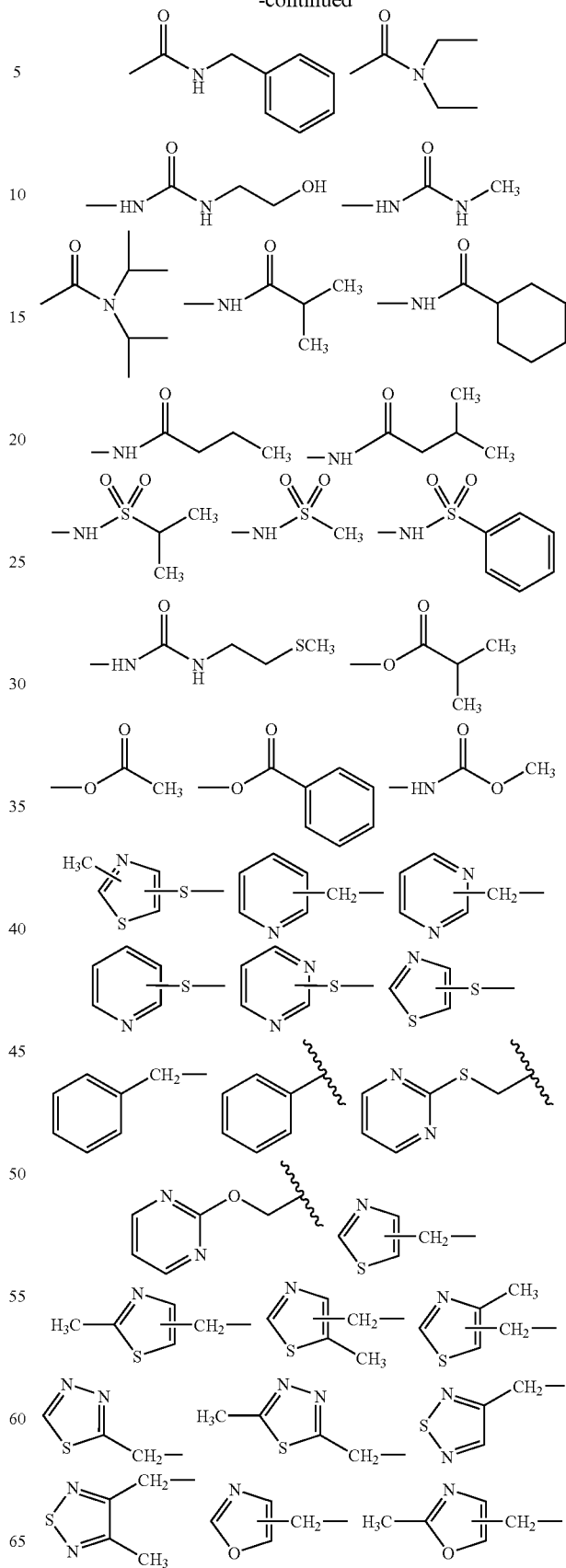

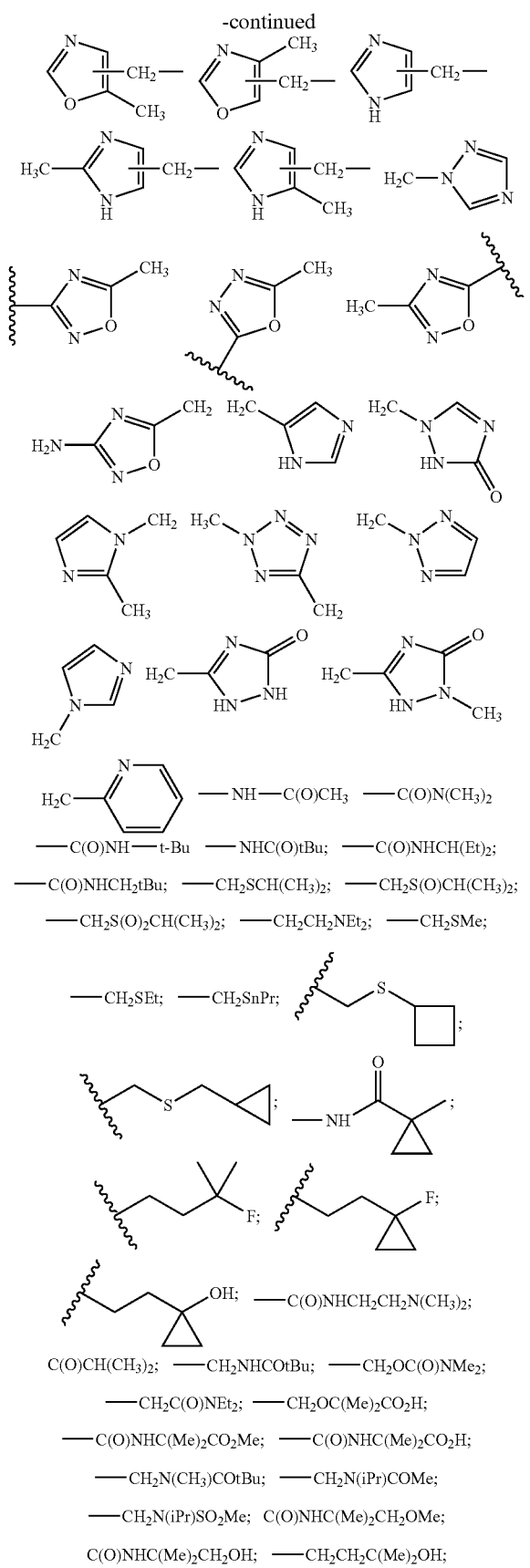
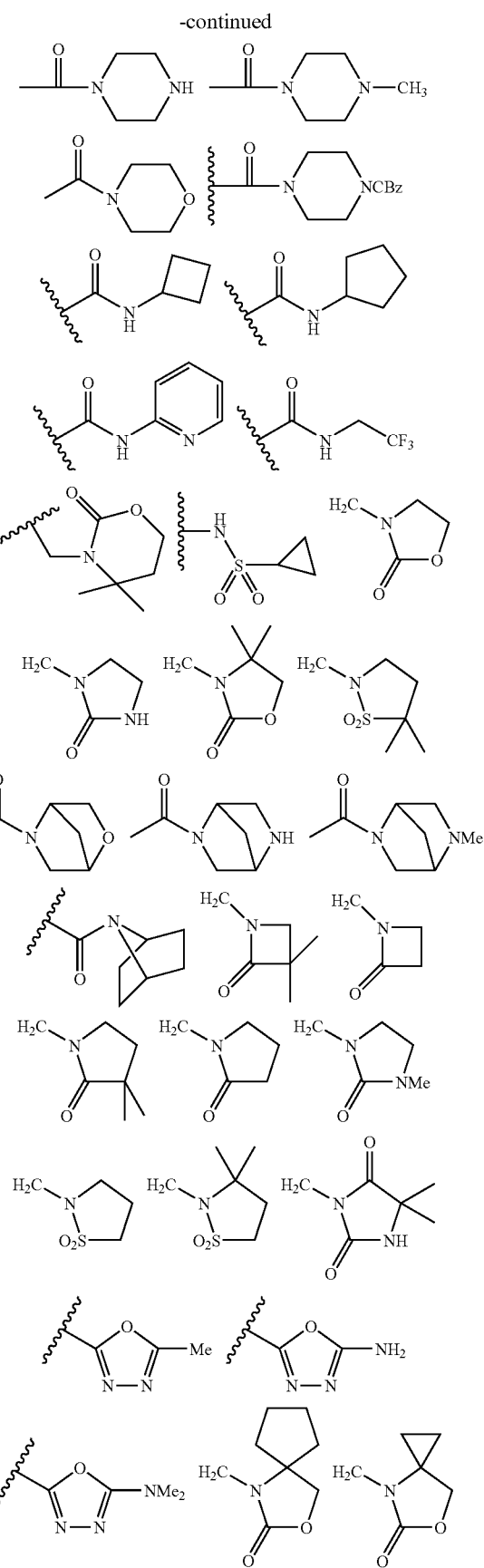

-continued

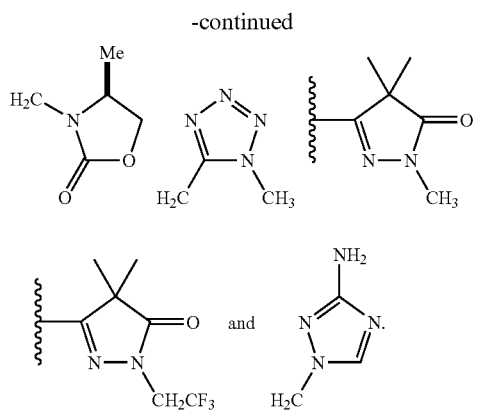

In a class of this embodiment of the compounds of structural formula II, the carbon atom marked with * has the R configuration.

In a second class of this embodiment of the compounds of structural formula II, m is 1.

In a third class of this embodiment of the compounds of structural formula II, $R^3$ and $R^5$ are each independently hydrogen or $C_{1-4}$ alkyl, and $R^7$ and $R^9$ are hydrogen.

In a fourth class of this embodiment of the compounds of structural formula II, at least one of $R^3$, $R^5$, $R^7$, and $R^9$ is $C_{1-4}$ alkyl.

Illustrative, but nonlimiting, examples of compounds of the present invention that are useful as melanocortin-4 receptor agonists are compounds of the formula III:

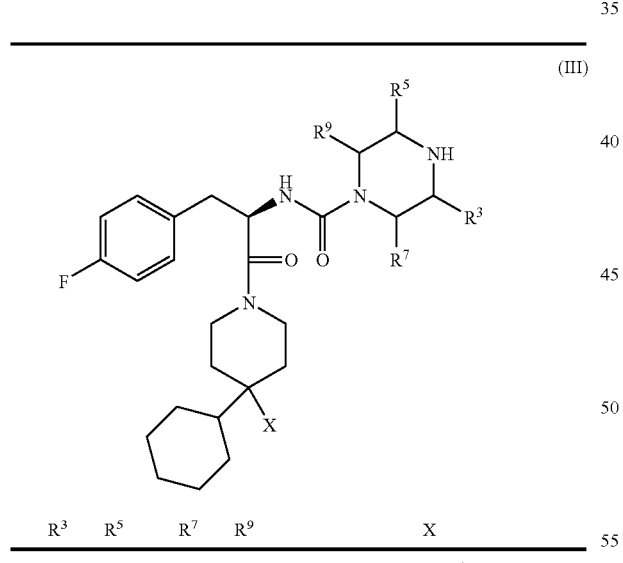

(III)

| $R^3$ | $R^5$ | $R^7$ | $R^9$ | X |
|---|---|---|---|---|
| Me | Me | H | H | 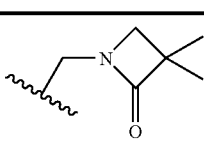 |
| Me | Me | H | H | |

-continued

(III)

| $R^3$ | $R^5$ | $R^7$ | $R^9$ | X |
|---|---|---|---|---|
| Me | Me | H | H | |
| Me | Me | H | H | 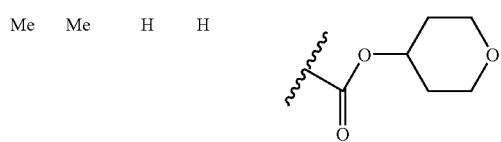 |
| Me | Me | H | H | 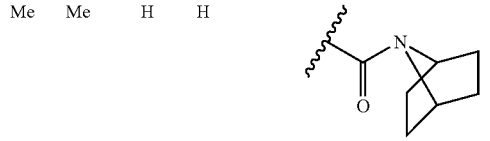 |
| Me | Me | H | H | 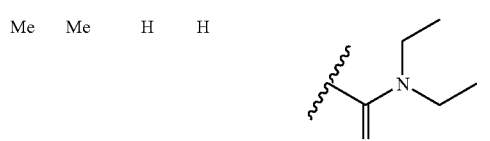 |
| Et | Et | H | H | 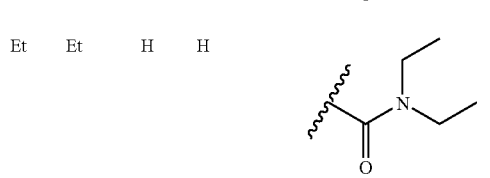 |
| Et | Et | H | H | 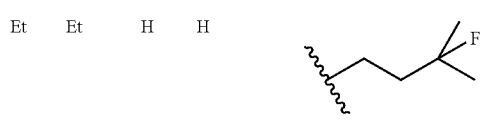 |
| Et | Et | H | H | 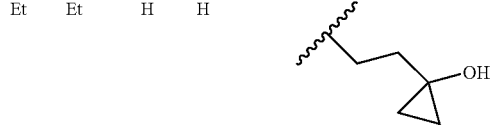 |

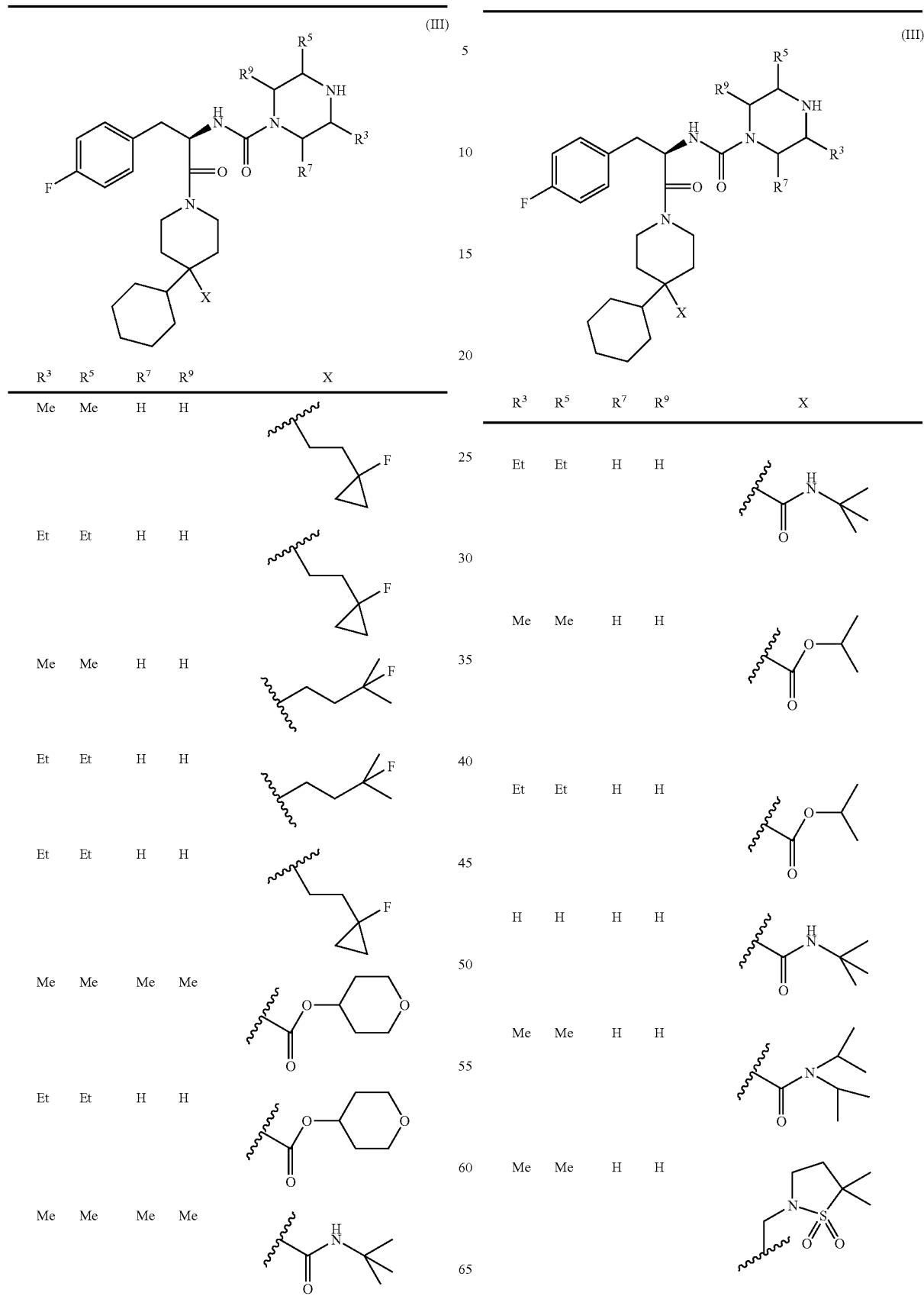

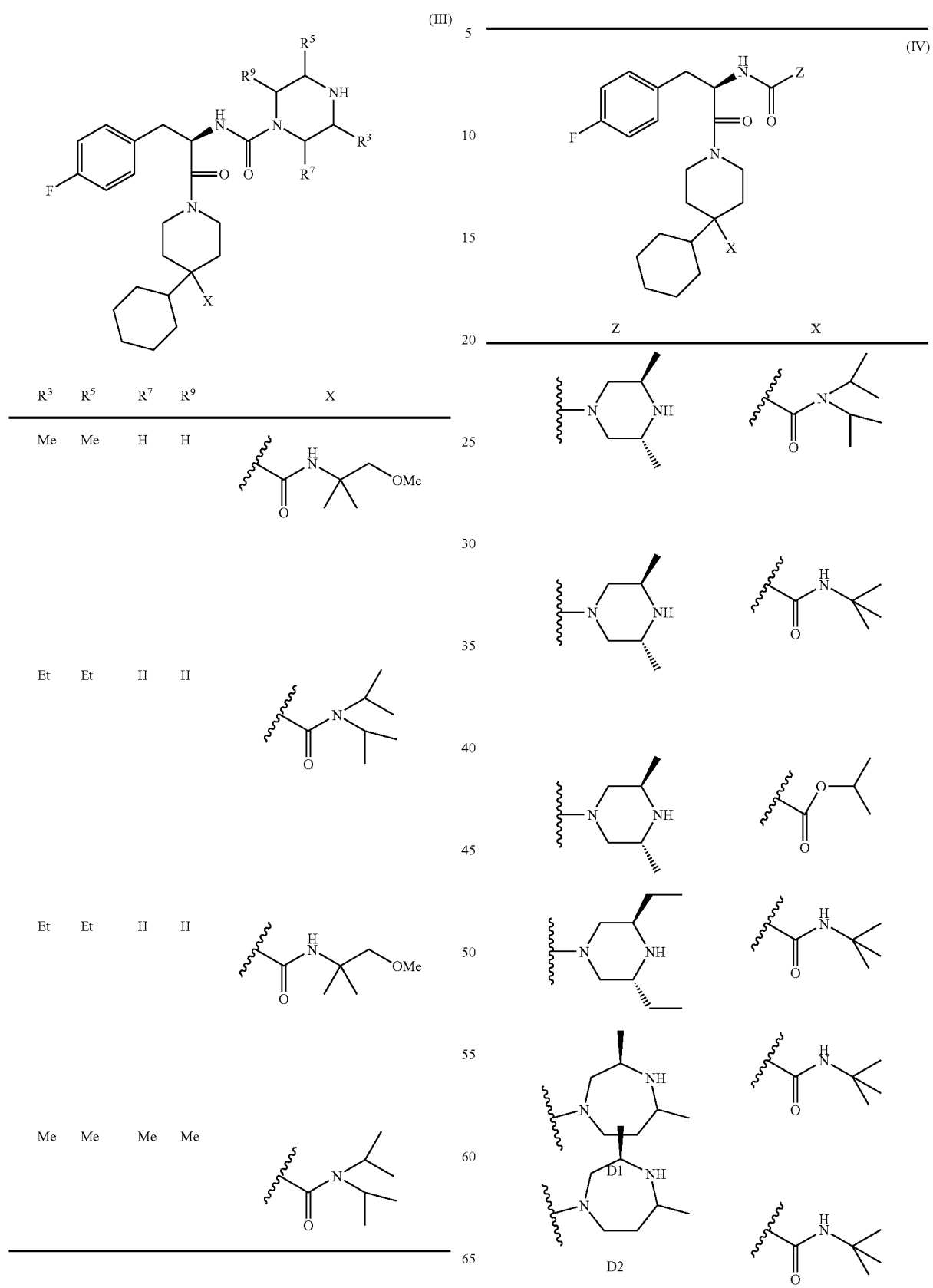

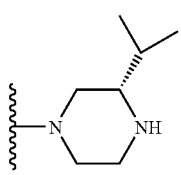 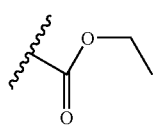
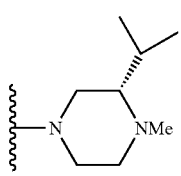 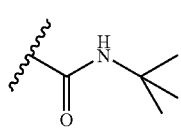
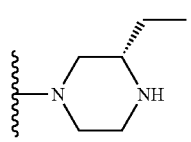 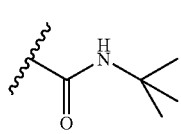
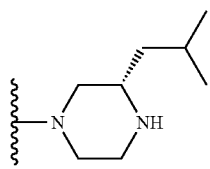 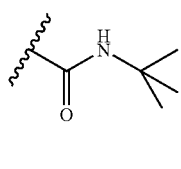
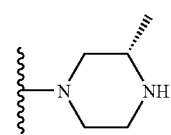 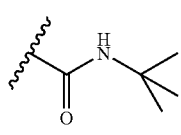
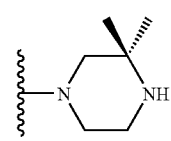 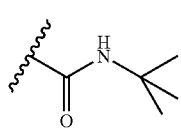
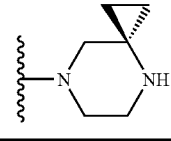 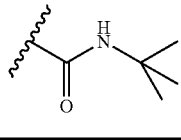
or a pharmaceutically acceptable salt thereof.
Further examples of compounds of the present invention that are useful as melanocortin-4 receptor agonists are compounds of the formula V:
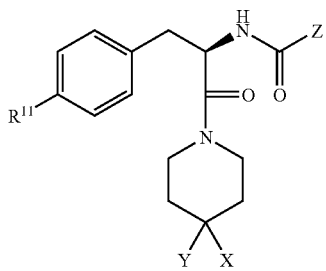

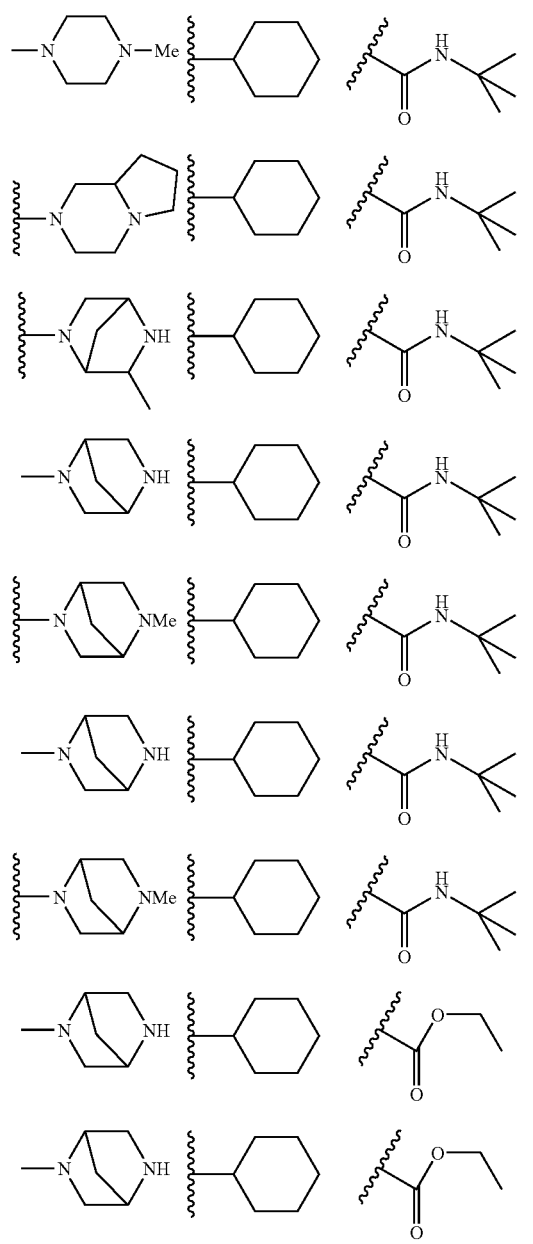

The compounds of structural formula I are effective as melanocortin-4 receptor agonists and are particularly effective as receptor-subtype selective partial agonists of MC-4R. They are useful for the treatment, control, or prevention of disorders responsive to the activation of MC-4R, such as obesity and diabetes.

Another aspect of the present invention provides a method for the treatment, control, or prevention of obesity or diabetes in a subject in need thereof which comprises administering to said subject a therapeutically or prophylactically effective amount of a compound of structural formula I.

Another aspect of the present invention provides a pharmaceutical composition comprising a compound of structural formula I and a pharmaceutically acceptable carrier.

Yet another aspect of the present invention provides a method for the treatment, control, or prevention of obesity which comprises administering to a subject in need of such treatment or prevention a therapeutically or prophylactically effective amount of a compound of structural formula I in combination with a therapeutically effective amount of another agent known to be useful for the treatment of this condition.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "alkenyl" refers to carbon chains which contain at least one carbon-carbon double bond, and which may be linear or branched or combinations thereof, unless the carbon chain is defined otherwise. Examples of alkenyl include vinyl, allyl, isopropenyl, pentenyl, hexenyl, heptenyl, 1-propenyl, 2-butenyl, 2-methyl-2-butenyl, and the like. Where the specifice number of carbon atoms permits, e.g., from $C_{5-10}$, the term alkenyl also includes cycloalkenyl groups, and combinations of linear, branched and cyclic structures. When no number of carbon atoms is specified, $C_{2-6}$ is intended.

The term "cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "halogen" is intended to include the halogen atoms fluorine, chlorine, bromine and iodine.

The term "aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

The term "heteroaryl" includes mono- and bicyclic aromatic rings containing from 1 to 4 heteroatoms selected from nitrogen, oxygen and sulfur. "5- or 6-Membered heteroaryl" represents a monocyclic heteroaromatic ring; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "heterocycle" or "hetercyclyl" refers to a saturated or unsaturated non-aromatic ring or ring system containing at least one heteroatom selected from O, S and N, further including the oxidized forms of sulfur, SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, teterhydropyran, dihydropyran, oxathiolane, dithiolane, 1,3-dioxane, 1,3-dithiane, oxathiane, thiomorpholine, and the like.

Certain of the above defined terms may occur more than once in the above formula and upon such occurrence each term shall be defined independently of the other; thus for example, $NR^{12}R^{12}$ may represent $NH_2$, $NHCH_3$, $N(CH_3)CH_2CH_3$, and the like.

An embodiment of the term "mammal in need thereof" is a "human in need thereof," said human being either male or female.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect. By "full agonist" is meant a drug that, at a maximally effective concentration, will induce maximal activation of a receptor population, that is, will drive the receptor "completely" to the active state. By "partial agonist" is meant an agonist which is unable to induce maximal activation of a receptor population, regardless of the amount of drug applied. Reference is made Goodman and Gilman, "The Pharmacological Basis of Therapeutics," $8^{th}$ Ed., Pergamon Press, Section I, pages 43-48 (1990), for a detailed discussion of quantitative aspects of drug-receptor interactions, which is incorporated by reference herein in its entirety.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I and II may be obtained by stereospecific synthesis using optically pure starting materials or reagents of known absolute configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Structural formula I are meant to also include the pharmaceutically acceptable salts.

Utility

Compounds of structural formula I are melanocortin-4 receptor agonists and as such are useful in the treatment, control or prevention of diseases, disorders or conditions responsive to the activation of the melanocortin-4 receptor. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, fever, inflammation, immunemodulation, rheumatoid arthritis, skin tanning, acne and other skin disorders, neuroprotective and cognitive and memory enhancement including the treatment of Alzheimer's disease. Some of the compounds encompassed by formula I are highly selective agonists of the melanocortin-4 receptor relative to MC-1R, MC-2R, MC-3R, and MC-5R, which makes them especially useful in the treatment, control, or prevention of obesity and diabetes. They are also useful in delaying or preventing the onset of type 2 (insulin-independent) diabetes in obese patients at risk of developing the disease. Some of the compounds encompassed by structural formula I are highly selective "partial agonists" of the melanocortin-4 receptor, which makes them especially useful in the prevention and treatment of obesity and diabetes, but with diminished erectogenic properties of "full agonists" of MC-4R.

The compositions of the present invention are also useful for the treatment or prevention of obesity-related disorders. The obesity herein may be due to any cause, whether genetic or environmental.

The obesity-related disorders herein are associated with, caused by, or result from obesity. Examples of obesity-related disorders include overeating, binge eating, and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compositions of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type 1 diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering IDL cholesterol in a subject with high IDL cholesterol levels. Another outcome of treatment may be increasing HDL cholesterol in a subject with low HDL cholesterol levels. Another outcome may be decreasing the JDLJHDL ratio in a subject in need thereof. Another outcome of treatment may be increasing insulin sensivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreading triglycerides in a subject with elevated triglycerides. Yet another outcome may be improving LDL cholestrol, non-HDL cholesterol, triglyceride, HDL cholesterol or other lipid analyte profiles.

Prevention of diabetes mellitus refers to the administration of a compound or combination of the present invention to prevent the onset of diabetes in a mammal at risk thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis.

The administration of the compounds of the present invention in order to practice the present methods of therapy is carried out by administering a therapeutically or prophylactically effective amount of the compound to a subject in need of such treatment or prophylaxis. The need for a prophylactic administration according to the methods of the present invention is determined via the use of known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art.

The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder.

The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Structural formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of structural formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

When treating an obesity-related disorder, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750, 1000, 1250 or 1500 milligrams of the active ingredient for the symptomatic adjustment of the dosage to the patient to be treated.

For use where a composition for intravenous administration is employed, a suitable dosage range is from about 0.001 mg to about 100 mg, preferably from 0.01 mg to about 50 mg, more preferably 0.1 mg to 10 mg, of a compound of Formula I per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of Formula I in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Combination Therapy

Compounds of structural formula I may be used in combination with other drugs that are used in the treatment/prevention/suppression or amelioration of the diseases or conditions for which compounds of structural formula I are useful. Such other drugs may be administered, by a route and in an amount commonly used therefor, contemporaneously or sequentially with a compound of structural formula I. When a compound of structural formula I is used contemporaneously with one or more other drugs, a pharmaceutical composition containing such other drugs in addition to the compound of structural formula I is preferred. When a composition of the present invention is used contemporaneously with one or more other drugs, a pharmaceutical composition in unit dosage form containing such other drugs and the composition of the present invention is preferred. However, the combination therapy also includes therapies in which the composition of the present invention and one or more other drugs are administered on different overlapping schedules. It is also contemplated that when used in combination with one or more other active ingredients, the composition of the present invention and the other active ingredients may be used in lower doses than when each is used singly. Accordingly, the pharmaceutical compositions of the present invention include those that also contain one or more other active ingredients, in addition to a compound of structural formula I.

Examples of other active ingredients that may be combined with a compound of structural formula I for the treatment or prevention of obesity and/or diabetes, either administered separately or in the same pharmaceutical compositions, include, but are not limited to:

(a) insulin sensitizers including (i) PPARγ agonists such as the glitazones (e.g. ciglitazone; darglitazone; troglitazone, pioglitazone, englitazone, isaglitazone (MCC-555), BRL49653, rosiglitazone; CLX-0921; 5-BTZD), GW-0207, LG-100641, and LY-300512, and the like), and compounds disclosed in WO97/10813, WO97/27857, 97/28115, 97/28137 and 97/27847;

ii) biguanides such as metformin (Glucophage®), buformin, and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)—NH$_2$);

(c) sulfonylureas, such as tolbutamide and glipizide, acetohexamide; chlorpropamide; diabinese; glibenclamide; glyburide; glimepiride; gliclazide; glipentide; gliquidone; glisolamide; and tolazamide;

(d) α-glucosidase inhibitors (such as acarbose, adiposine; camiglibose; emiglitate; miglitol; voglibose; pradimicin-Q; salbostatin; CKD-711; MDL-25,637; MDL-73,945; and MOR 14, and the like);

(e) cholesterol lowering agents such as (i) HMG-CoA reductase inhibitors (lovastatin, simvastatin, pravastatin, fluvastatin, atorvastatin, itavastatin, rivastatin, rosuvastatin, ZD-4522, and other statins), (ii) sequestrants (cholestyramine, colestipol and a dialkylaminoalkyl derivatives of a cross-linked dextran, colesevelum, Colestid®; LoCholest®, and the like, (ii) nicotinyl alcohol nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption for example beta-sitosterol, stanol esters, sterol glycosides such as tiqueside; and azetidinones such as ezetimibe, efucimibe, KY 505, SMP797, and the like, and (acyl CoA:cholesterol acyltransferase) inhibitors for example melinamide, and avasirnibe, (v) anti-oxidants such as probucol, (vi) vitamin E, and (vii) thyroniimetics;

(f) PPARδ agonists, such as those disclosed in WO97/28149, and such as GW 501516, and GW 590735, and the like;

(g) anti-obesity serotonergic agents, such as fenfluramine, dexfenfluramine, phentermine, and sibutramine;

(h) β3-adrenoreceptor agonists, such as AD9677/TAK677 (Dainippon/Takeda), CL-316,243, SB 418790, BRL-37344, I-796568, BMS-196085, BRL-35135A, CGP12177A, GW 427353, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897;

(i) pancreatic lipase inhibitors, such as orlistat (Xenical®), Triton WR1339, RHC80267, lipstatin, tetrahydrolipstatin, teasaponin, diethyl-umbelliferyl phosphate, FL-386, WAY-121898, Bay-N-3176, valilactone, esteracin, ebelactone A, ebelactone B, and RHC 80267, and those disclosed in PCT Application No. WO 01/77094, and U.S. Pat. Nos. 4,598,089, 4,452,813, 5,512,565, 5,391,571, 5,602,151, 4,405,644, 4,189,438, and 4,242,453;

(j) feeding behavior modifying agents, such as neuropeptide Y Y1 and Y5 antagonists, such as those disclosed in WO 97/19682, WO 97/20820, WO 97/20821, WO 97/20822, WO 97/20823, WO 01/14376, and U.S. Pat. No. 6,191,160; neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; and neuropeptide Y5 antagonists, such as 152,804, GW-569180A, GW-594884A, GW-587081X, GW-548118X, FR235,208, FR226928, FR 240662, FR252384, 1229U91, GI-264879A, CGP71683A, LY-377897, LY-366377, PD-160170, SR-120562A, SR-120819A, JCF-104, and H409/22; and those disclosed in U.S. Pat. Nos. 6,140,354, 6,191,160, 6,258,837, 6,313,298, 6,337,332, 6,329,395, 6,326,375, 6,335,345, and 6,340,683, European Patent Nos. EP-01010691, and EP-01044970, and PCT Patent Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648 and WO 02/094789; and Norman et al., J. Med. Chem. 43:4288-4312 (2000);

(k) orexin-1 receptor antagonists, such as SB-334867-A, and those disclosed in PCT Patent Application Nos. WO 01/96302, WO 01/68609, WO 02/51232, WO 02/51838, and WO 03/023561;

(l) PPARα agonists such as described in WO 97/36579 by Glaxo, and PPARα agonists such as beclofibrate, benzafibrate, ciprofibrate, clofibrate, etofibrate, fenofibrate, gemcabene, gemfibrozil, GW 7647, BM 170744, and LY518674; and other fibric acid derivatives, such as Atromid®, Lopid® and Tricor®, and the like;

(m) PPARγ antagonists as described in WO97/10813;

(n) serotonin reuptake inhibitors such as fluoxetine, paroxetine, and sertraline;

(O) growth hormone secretagogues, such as MK-0677, and growth hormone secretagogue receptor agonists/antagonists, such as $NN_7O_3$, hexarelin, SM-130686, CP-424,391, L-692,429 and L-163,255, and such as those disclosed in U.S. Pat. Nos. 5,536,716, and 6,358, 951, U.S. Patent Application Nos. 2002/049196 and 2002/022637, and PCT Application Nos. WO 01/56592 and WO 02/32888;

(p) cannabinoid receptor ligands, such as cannabinoid $CB_1$ receptor antagonists or inverse agonists, such as rimonabant (Sanofi-Synthelabo), and SR-147778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/ 076949, WO 03/0060007, and WO 03/007887; and EPO Application No. EP-658546, EP-656354, EP-576357;

(q) protein tyrosine phosphatase-1B (PTP-1B) inhibitors; and (r) anti-obesity agents, such as (1) melanin-concentrating hormone MCH) receptor antagonists, such as those disclosed in WO 01/21577 and WO 01/21169; (2) melanin-concentrating hormone 1 receptor (MCH1R) antagonists; such as T-226296 (Takeda), SNP-7941, and those disclosed in PCT Patent Application Nos. WO 01/82925, WO 01/87834, WO 02/051809, WO 02/06245, WO 02/04433, WO 02/076929, WO 02/076947, WO 02/51809, WO 02/083134, WO 02/094799, and WO 03/004027, and Japanese Patent Application No. JP 13226269; (3) melanin-concentrating hormone 2 receptor ($MCH_2R$) agonist/antagonists; (4) serotonin reuptake inhibitors such as fluoxetine, paroxetine and sertraline, and those disclosed in U.S. Pat. No. 6,365,633, and PCT Patent Application Nos. WO 01/27060 and WO 01/162341; (5) melanocortin agonists, such as Melanotan II or those described in WO 99/64002 and WO 00/74679; (6) other Mc4r (melanocortin 4 receptor) agonists, such as CHIR86036 (Chiron), ME-10142, and ME-10145 (Melacure), and those disclosed in PCT Application Nos. WO 01/991752, WO 01/74844, WO 02/12166, WO 02/11715, and WO 02/12178; (7) 5HT-2 agonists; (8) 5HT2C (serotonin receptor 2C) agonists, such as BVT933, DPCA37215, WAY161503, R-1065, IK264, and PNU 22394, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (9) galanin antagonists; (10) CCK agonists; (11) CCK-A (cholecystokinin-A) agonists, such as AR-R 15849, GI 181771, JMV-180, A-71378, A-71623 and SR146131, and those discribed in U.S. Pat. No. 5,739,106; (12) GLP-1 (glucagon like peptide 1 agonists; (13) corticotropin-releasing hormone agonists; (14) histamine receptor-3 ($H_3$) modulators; (15) histamine receptor-3 ($H_3$) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), A 331440, and those described and disclosed in PCT Application No. WO 02/15905, and O-[3-(1H-imidazol-4-yl) propanol]-carbamates (Kiec-Kononowicz, K. et al., Pharmazie, 55:349-55 (2000)), piperidine-containing histamine $H_3$-receptor antagonists Lazewska, D. et al., Pharmazie, 56:927-32 (2001), benzophenone derivatives and related compounds (Sasse, A. et al., Arch. Pharm. (Weinheim) 334: 45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (16) 11β-hydroxy steroid dehydrogenase-1 inhibitors (11β-HSD-1), such as BVT 3498, BVT 2733, and those compounds disclosed in WO 01/90091, WO 01/90090, WO 01/90092; (17) PDE (phosphodiesterase) inhibitors, such as theophylline, pentoxifylline, zaprinast, sildenafil, amrinone, milrinone, cilostamide, rolipram, and cilomilast; (18) phosphodiesterase-3B (PDE3B) inhibitors; (19) NE (norepinephrine) transport inhibitors, such as GW 320659, despiramine, talsupram, and nomifensine; (20) ghrelin receptor antagonists, such as those disclosed in PCT Application Nos. WO 01/87335, and WO 02/08250; (21) leptin, including recombinant human leptin (PEG-OB, Hoffman La Roche) and recombinant methionyl human leptin (Amgen); (22) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (23) BRS3 (bombesin receptor subtype 3) agonists; (24) CNTF (Ciliary neurotrophic factors), such as GI-181771 (Glaxo-SmithKiine), SR146131 (Sanofi Synthelabo), butabindide, PD170,292, and PD 149164 (Pfizer); (25) CNTF derivatives, such as axokine (Regeneron), and those disclosed in PCT Application Nos. WO 94/09134, WO 98/22128, and WO 99/43813; (26) monoamine reuptake inhibitors, such as sibutramine (Meridia ®/Reductil®), and those disclosed in U.S. Pat. Nos. 4,746, 680, 4,806,570, and 5,436,272, and U.S. Patent Publication No. 2002/0006964, WO 01/27068, and WO 01/62341; (27) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (28) thyroid hormone β agonists, such as KB-2611 (KaroBioBMS), and those disclosed in PCT Application No. WO 02/15845, and Japanese Patent Application No. JP 2000256190; (29) FAS (fatty acid synthase) inhibitors, such as Cerulenin and C75; (30) DGAT1 (diacylglycerol acyltransferase 1) inhibitors; (31) DGAT2 (diacylglycerol acyltransferase 2) inhibitors; (32) ACC2 (acetyl-CoA carboxylase-2) inhibitors; (33) glucocorticoid antagonists; (34) acyl-estrogens, such as oleoyl-estrone, disclosed in del Mar-Grasa, M. et al., Obesity Research, 9:202-9 (2001); (35) dipeptidyl peptidase IV (DP-IV) inhibitors, such as isoleucine thiazolidide; NVP-DPP728; P32/98; LAF 237, TSL 225, valine pyrrolidide, TMC-2A/2B/2C, CD-26 inhibitors, FE 999011, P9310/K364, VIP 0177, DPP4, SDZ 274-444; and the compounds disclosed in WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (36) fatty acid transporter inhibitors; (37) dicarboxylate transporter inhibitors; (38) glucose transporter inhibitors; (39) phosphate transporter inhibitors; (40) Topiramate (Topimax®); (41) 5T (serotonin) transporter inhibitors, such as paroxetine, fluoxetine, fluvoxamine, sertraline, and imipramine; (42) opioid antagonists, such as nalmefene (Revex®), 3-methoxynaltrexone, naloxone, and naltrexone; and those disclosed in WO 00/21509; (43) Mc3r (melanocortin 3 receptor) agonists; (44) phytopharm compound 57 (CP 644,673); (45) FAS (fatty acid synthase) inhibitors, such as Cerulenin and C75; (46) SCD-1 (stearoyl-CoA desaturase-1) inhibitors; and the like; (47) a minorex; (48) amphechloral; (49) amphetamine; (50) benzphetamine; (51) chlorphentermine; (52) clobenzorex; (53) cloforex; (54) clominorex; (55) clortermine; (56) cyclexedrine; (57) dextroamphetamine; (58) diethylpropion; (59) diphemethoxidine, (60) N-ethylamphetamine; (61) fenbutrazate; (62) fenisorex; (63) fenproporex; (64) fludorex; (65) fluminorex; (66) furfurylmethylamphetamine; (67) levamfetamine; (68) levophacetoperane;

(69) mazindol; (70) mefenorex; (71) metamfepramone; (72) methamphetamine; (norpseudoephedrine; (73) pentorex; (74) phendimetrazine; (75) phemnetrazine; (76) phenylpropanolamine; (77) picilorex; and (78) zonisamide, and the like;

(s) lipid lowering agents such as (1) CETP inhibitors such as JTT 705, torcetrapib, CP 532,632, BAY63-2149, SC 591, SC 795, and the like; (2) squalene synthetase inhibitors; (3) FXR receptor modulators such as GW 4064, SR 103912, and the like; (4) LXR receptor such as GW 3965, T9013137, and XTCO179628, and the like; (5) lipoprotein synthesis inhibitors such as niacin; (6) renin angiotensin system inhibitors; (7) PPAR δ partial agonists; (8) bile acid reabsorption inhibitors, such as BARI 1453, SC435, PHA384640, S8921, AZD7706, and the like; (9) triglyceride synthesis inhibitors; (10) microsomal triglyceride transport (MFIP) inhibitors, such as inplitapide, LAB687, and CP346086, and the like; (11) transcription modulators; (12) squalene epoxidase inhibitors; (13) low density lipoprotein (LDL) receptor inducers; (14) platelet aggregation inhibitors; (15) 5-LO or FLAP inhibitors; and (16) niacin receptor agonists;

(t) anti-diabetic agents such as (1) meglitinides such as repaglinide, and nateglinide, and the like; (2) alpha-amylase inhibitors such as tendamistat, trestatin, and Al-3688, and the like; (3) insulin secreatagogues such as linogliride; and A-4166, and the like; (4) fatty acid oxidation inhibitors, such as clomoxir, and etomoxir, and the like; (5) A2 antagonists, such as midaglizole; isaglidole; deriglidole; idazoxan; earoxan; and fluparoxan, and the like; (6) non-thiazolidinediones such as JT-501, and farglitazar (GW-2570/GI-262579), and the like; (7) PPARα/γ dual agonists such as CLX-0940, GW-1536, GW1929, GW-2433, KRP-297, L-796449, LR-90, SB 219994, and MK-767, and the like; (8) other insulin sensitizing drugs; and (9) VPAC2 receptor agonists; and (u) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetamide, ethacrynic acid, furosernide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XENO10, and the like; (11) alpha 2 agonists such as lofexidine, tiamenidine, moxonidine, rilmenidine and guanobenz, and the like; and (12) aldosterone inhibitors, and the like.

Examples of anti-obesity agents that can be employed in combination with a compound of structural formula I are disclosed in "Patent focus on new anti-obesity agents," *Exp. Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Pin. Ther. Patents,* 11: 1677-1692 (2001). The role of neuropeptide Y in obesity is discussed in *Exp. Opin. Invest. Drugs,* 9: 1327-1346 (2000). Cannabinoid receptor ligands are discussed in *Exp. Opin. Invest. Drugs,* 9: 1553-1571 (2000). Various pharmacological approaches for the treatment of obesity is discussed in J-A Fernandez-Lopez, *Drugs:* 62: 915-944 (2002) and in H. Bays, et al., "Anti-obesity drug development," *Exp. Opin. Invest. Drugs,* 11: 1189-1204 (2002), and in D. Spanswick, et al., "emerging Anti-obesity Drugs," *Exp. Opin. Emerging Drugs,* 8 (1): 217-237 (2003).

The instant invention also includes administration of a single pharmaceutical dosage formulation which contains both the MC-4R agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly.

Administration in these various ways are suitable for the present compositions as long as the beneficial pharmaceutical effect of the combination of the MC-4R agonist and the second active ingredient is realized by the patient at substantially the same time. Such beneficial effect is preferably achieved when the target blood level concentrations of each active ingredient are maintained at substantially the same time. It is preferred that the combination of the MC-4R agonist and the second active ingredient be co-administered concurrently on a once-a-day dosing schedule; however, varying dosing schedules, such as the MC-4R agonist once a day and the second active ingredient once, twice or more times per day, is also encompassed herein. A single oral dosage formulation comprised of both a MC-4R agonist and a second active ingredient is preferred. A single dosage formulation will provide convenience for the patient, which is an important consideration especially for patients with diabetes or obese patients who may be in need of multiple medications.

The above combinations include combinations of a composition of the present invention not only with one other active compound, but also with two or more other active compounds. Non-limiting examples include combinations of the compositions of the present invention with one, two or more active compounds selected from lipid-lowering agents, and anti-hypertensive agents. Combinations of the compositions of the present invention with one, two or more active compounds selected from lipid lowering agents, and anti-diabetic agents are useful to treat, control or prevent metabolic syndrome. In particular, compositions comprising an anti-obesity agent, such as a melanocortin-4 receptor agonist, an anti-hypertensive agent, in addition to an anti-diabetic agent and/or a lipid lowering agent will be useful to synergistically treat, control or prevent metabolic syndrome.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the melanocortin-4 receptor agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form.

In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Pharmaceutical Compositions

Another aspect of the present invention provides pharmaceutical compositions which comprises a compound of structural formula I and a pharmaceutically acceptable carrier. The pharmaceutical compositions of the present invention comprise a compound of structural formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I of the present invention can be prepared according to the procedures of the following Schemes and Examples, using appropriate materials and are further exemplified by the following specific examples. Moreover, by utilizing the procedures described in detail in U.S. Pat. No. 6,294,534 (25 Sep. 2001) and U.S. Pat. No. 6,350,760 (26 Feb. 2002), which are incorporated by reference herein in their entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation; The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as methylene chloride in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention:

| | |
|---|---|
| BOC (boc) | t-butyloxycarbonyl |
| BOP | benzotriazol-1-yloxytris(dimethylamino)phosphonium hexafluorophosphate |
| Bn | benzyl |
| Bu | butyl |
| calc. | calculated |
| Celite | tradename for diatomaceous earth |
| CBZ (Cbz) | benzyloxycarbonyl |
| $CH_2Cl_2$ | methylene chloride |
| c-hex | cyclohexyl |
| c-pen | cyclopentyl |
| c-pro | cyclopropyl |
| DEAD | diethyl azodicarboxylate |
| DIEA | diisopropylethylamine |
| DMAP | 4-dimethylaminopyridine |
| DMF | N,N-dimethylformamide |
| DMSO | dimethylsulfoxide |
| [DPPP]$NiCl_2$ | [1,3-Bis(diphenylphosphino)propane]dichloronickel(II) |
| EDC | 1-(3-dimethylaminopropyl)3-ethylcarbodiimide HCl |
| eq. | equivalent(s) |
| ES-MS | electron spray ion-mass spectroscopy |
| Et | ethyl |
| $Et_2O$ | diethyl ether |
| EtOAc | ethyl acetate |
| HATU | N-[(dimethylamino)-1H-1,2,3-triazolo[4,5-b] pyridin-1-ylmethylene]-N-methylmethanaminium hexafluorophosphate N-oxide |
| HOAt | 1-hydroxy-7-azabenzotriazole |
| HOBt | 1-hydroxybenzotriazole hydrate |
| HPLC | high performance liquid chromatography |
| LAH | lithium aluminum hydride |
| LDA | lithium diisopropylamide |
| MC-xR | melanocortin receptor (x being a number) |
| Me | methyl |
| $MgSO_4$ | magnesium sulfate |
| MF | molecular formula |
| MS | mass spectrum |
| Ms | methanesulfonyl |
| MTBE | tert-butyl methyl ether |
| $Na_2SO_4$ | sodium sulfate |

-continued

| | |
|---|---|
| NEM | N-ethylmaleimide |
| NMM | N-methylmorpholine |
| NMP | 1-methyl-2-pyrrolidinone |
| Ph | phenyl |
| Phe | phenylalanine |
| Pr | propyl |
| prep. | prepared |
| PyBrop | bromo-tris-pyrrolidino-phosphonium hexafluorophosphate |
| OTf | trifluoromethanesulfonyloxy |
| r.t. | room temperature |
| TFA | trifluoroacetic acid |
| THF | tetrahydrofuran |
| TLC | thin-layer chromatography |
| TPAP | tetrapropylammonium perruthenate |
| TsOH | toluene sulfonic acid |

Reaction Schemes A and B illustrate the methods employed in the synthesis of the compounds of the present invention of structural formula I. All substituents are as defined above unless indicated otherwise.

Reaction Scheme A illustrates the key steps in the synthesis of the novel compounds of structural formula I of the present invention. As shown in reaction Scheme A, the reaction of a 4-substituted piperidine of general formula 1 with an amino acid derivative of general formula 2 followed by removal of the amine protecting group Q affords an intermediate amine of general formula 3. The amine of formula 3 is then converted into the desired unsymmetrical urea of structural formula I. Construction of the urea linkage is accomplished by conversion of the primary amine of formula 3 into an isocyanate by using phosgene in the presence of a tertiary amine [J. Nowick, et al., *J. Org. Chem.*, 57: 7364-7366 (1992)]. The generated isocyanate intermediate is then reacted with an optionally protected piperazine of general formula 4 followed by removal of the optional protecting group Q' to afford the desired compound of structural formula (I) ($R^2$=H). A preferred method for the preparation of the isocyanate involves reaction of primary amine 3 with triphosgene in the presence of aqueous sodium bicarbonate [J. Tsai, et al., *Org. Syn.*, 78: 220-224 (2000)]. Alternative methods for preparation of unsymmetrical ureas utilize carbonic acid-based reagents. N,N'-Disuccinimidylcarbonate (DSC) (Y. Konda et al., *Tetrahedron*, 57: 4311-4321 (2001)] is the most commonly used carbonic acid-based reagent. Unsymmetrical ureas are obtained by sequential reaction of amines with DSC. Other less frequently used carbonic acid-based reagents for the elaboration of a ureido linkage are 4-nitrophenyl chloroformate [J. Gante, *Chem. Ber.*, 98: 3334 (1965) and J. Izdiebski et al., *Synthesis*, 423 (1989)] and 1,1-carbonyldiimidazole [H. A. Staab, *Ann. Chem.*, 609: 75 (1957)].

The amide bond coupling reaction illustrated in reaction Scheme A is conducted in an appropriate inert solvent such as dimethylformamide (DMF), methylene chloride or the like and may be performed with a variety of reagents suitable for amide coupling reactions, such as O-(7-azabenzotriazol-1-yl)-1,1,3,3-tetramethyluronium hexafluorophosphate (HATU), 1-(3-dimethylaminopropyl)-3-ethylcarbodiimide hydrochloride (EDC) or benzotriazol-1-yloxytripyrrolidine-phosphonium hexafluorophosphate (PyBOP). Preferred conditions for the amide bond coupling reaction shown in reaction Scheme A are known to those skilled in organic synthesis. Such modifications may include, but are not limited to, the use of basic reagents such as triethylamine (TEA) or N-methylmorpholine (NMM), or the addition of an additive such as 1-hydroxy-7-azabenzotriazole (HOAt) or 1-hydroxybenzotriazole (HOBt). Alternatively, 4-substituted piperidines of formula 1 may be treated with an active ester or acid chloride derived from carboxylic acid 2 which also affords intermediates of formula 3. The amide bond coupling shown in reaction Scheme A is usually conducted at temperatures between 0° C. and room temperature, occasionally at elevated temperatures, and the coupling reaction is typically conducted for periods of 1 to 24 hours.

If it is desired to produce a compound of structural formula I wherein $R^2$ is a hydrogen, either an unprotected piperazine or a mono N-BOC or N-Cbz protected piperazine (Q'=H, BOC, or Cbz) may be used in the preparation of the compound of structural formula I and either Boc-deprotected under acidic conditions, for instance using trifluoroacetic acid in a solvent like methylene chloride or hydrogen chloride in a solvent such as ethyl acetate at room temperature, or Cbz-deprotected by catalytic hydrogenation.

When it is desired to prepare compounds of structural formula I wherein $R^2$ is not a hydrogen, the compounds of general formula I ($R^2$=H) may be further modified using the methodology described below in reaction Scheme B.

organic chemistry. For instance, compounds (I) ($R^2$=H) may be utilized in a reductive amination reaction with a suitable carbonyl containing partner of general formula 5. The reductive amination is achieved by initial formation of an imine between the amine of formula I ($R^2$=H) and either an aldehyde or ketone of formula 5. The intermediate imine is then treated with a reducing agent capable of reducing carbon-nitrogen double bonds such as sodium cyanoborohydride or sodium triacetoxyborohydride and an alkylated product of structural formula I is produced. Alternatively, a heterocyclic compound of structural formula (I) ($R^2$=H) may be directly alkylated using an alkylating agent such as 6 in a polar aprotic solvent such as DMF. In this reaction, the substituent Z of compound 6 is a good leaving group such as a halide, methanesulfonate (OMs), or trifluoromethanesulfonate (OTf), and the product is the compound of structural formula I bearing the $R^2$ substituent.

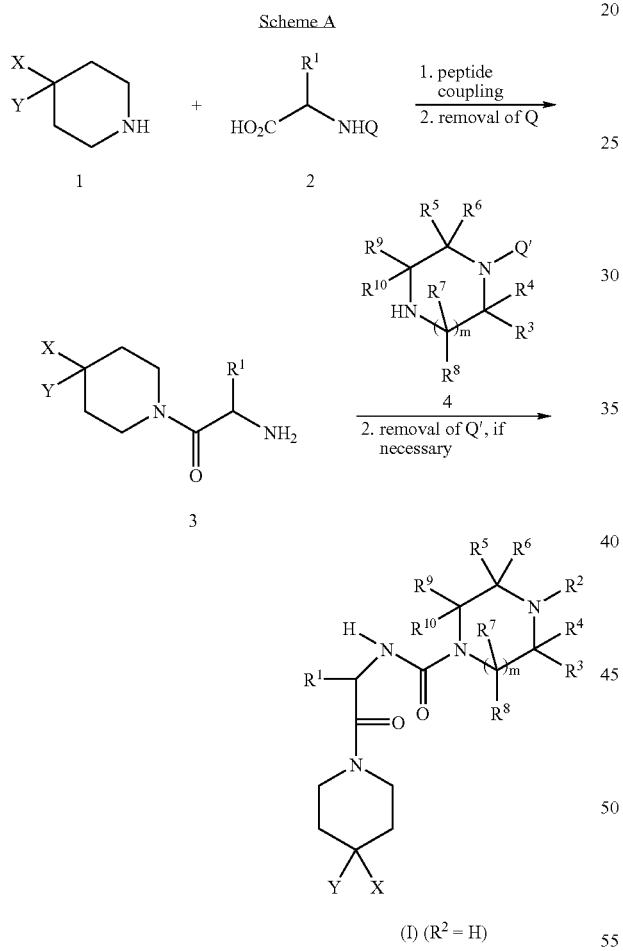

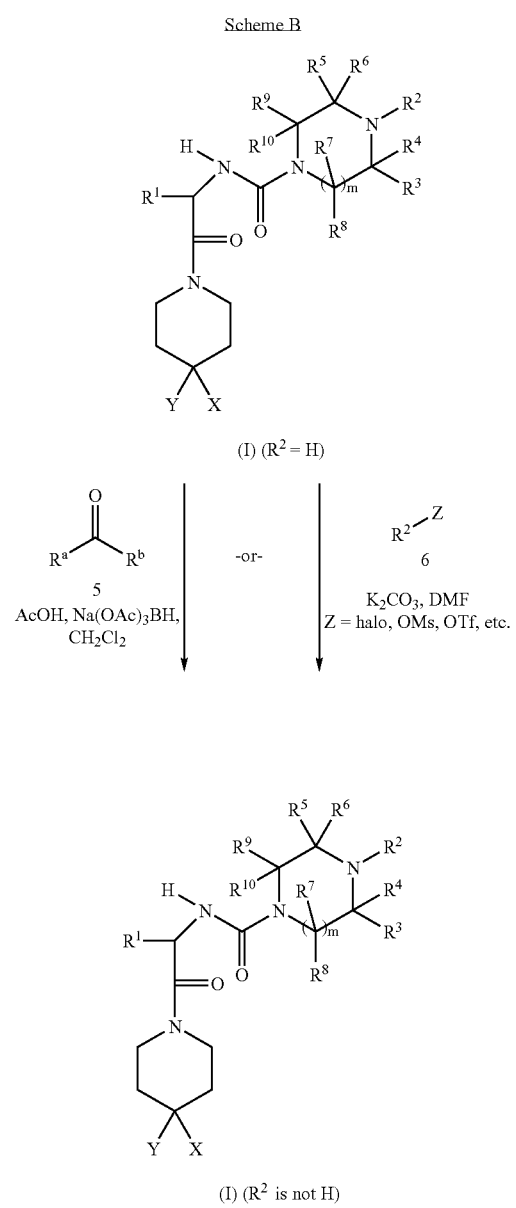

Reaction Scheme B illustrates general methods for the elaboration of an $R^2$ substituent following assembly of a compound of structural formula I (wherein $R^2$=BOC or Cbz) as described in reaction Scheme A. Either the N-BOC protected compound of structural formula I is first deprotected under acidic conditions for instance by treatment with hydrogen chloride in ethyl acetate or using trifluoroacetic acid in methylene chloride, or the N-Cbz protected compound is deprotected by catalytic hydrogenation. The resulting heterocyclic compound of structural formula I ($R^2$=H) may then be subjected to one of several alkylation strategies known in Preparation of 4-Substituted Piperidine Intermediates General Formula 1:

The preparation of 4-substituted piperidine intermediates of general structure 1 in Scheme A for coupling with the appropriate carboxylic acid intermediates of general structure 2 in Scheme A is disclosed in U.S. Pat. Nos. 6,350,760 and 6,458,790, which are incorporated by reference herein in their entirety. The synthesis of additional 4-substituted piperidine intermediates needed to prepare the compounds of the present invention is provided below.

Piperidine Intermediate 1:

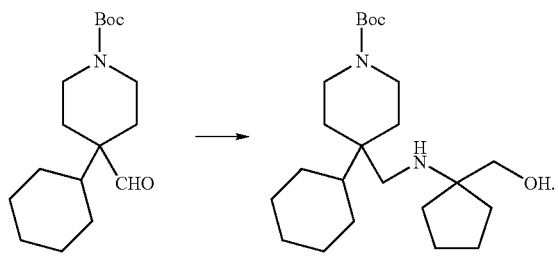

To a solution of 4-cyclohexyl 4-formyl-N-(tertbutyloxycarbonyl)-piperidine (2.56 g, 8.68 mmol) in toluene (100 mL) was added acetic acid (2 mL) and 1-amino-1-cyclopentanemethanol (1.0 g, 8.68 mmol). After refluxing by using a Dean-Stark apparatus for 11 h, the reaction mixture was concentrated. The residue was dissolved in acetic acid (70 mL) and hydrogenated overnight in the presence of platinum oxide (500 mg) under a balloon atmosphere of hydrogen gas. The catalyst was filtered off and solvent was removed to give a colorless oil, which was dissolved in methanol and made basic by addition of NaOH (5N, 4 mL) and concentrated. The residue was partitioned between water and $CH_2Cl_2$, the two layers separated, and the aqueous layer extracted with $CH_2Cl_2$. The combined organic extracts were washed with brine, dried over $MgSO_4$ and concentrated to give the title compound as a colorless oil (2.1 g).

MS: calc. for $C_{23}H_{42}N_2O_3$, 394.3. Found: 395 (M+1), 417 (M+Na).

Piperidine Intermediate 2:

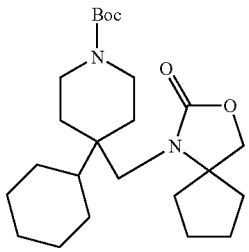

To a solution of Intermediate 1 (2.1 g, 5.33 mmol) in $CH_2Cl_2$ (70 mL) at 0° was added DMAP (0.65 g, 5.33 mmol), DIEA (3.76 mL, 21.3 mmol) followed by slow addition of phosgene (4.1 mL, 8.0 mmol). After stirring the reaction mixture for one hour at 0° C., the ice-water bath was removed and the reaction mixture was stirred at room temperature overnight. The mixture was diluted with $CH_2Cl_2$, washed with water and brine, dried over $MgSO_4$ and concentrated to give crude product, which was purified by column chromatography on silica gel (2% EtOAc/$CH_2Cl_2$ to 5% EtOAc/$CH_2Cl_2$) to give the title compound as a white solid (1.2 g).

MS: calc. for $C_{24}H_{40}N_2O_4$, 420.3. Found: (M+1), (M+Na).

Piperidine Intermediate 3:

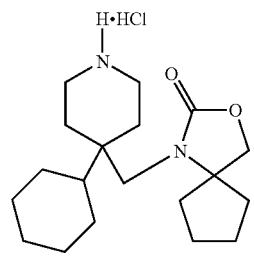

To the Intermediate 2 (1.2 g) was added hydrogen chloride (4.0 M in dioxane). The reaction mixture was stirred at room temperature for 30 min and the solvent was removed in vacuo to afford the title compound (1.2 g).

MS: calc. for $C_{19}H_{32}N_2O_2$: 320.3. Found: 321.1 (M+H).

Piperidine Intermediate 4:

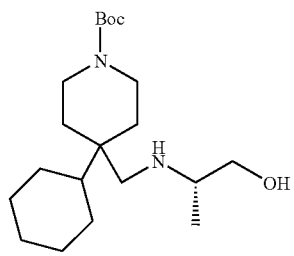

Intermediate 4 was prepared from (S)-(+)-2-amino-1-propanol in an analogous manner to the one described for the preparation of Intermediate 1.

MS: calc. for $C_{20}H_{38}N_2O_3$: 354. Found: 355 (M+H).

Piperidine Intermediate 5:

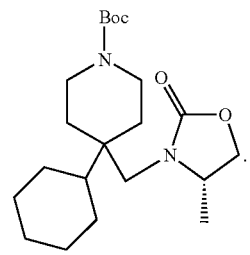

Intermediate 5 was prepared from Intermediate 4 in an analogous manner to the one described for the preparation of Intermediate 2.

MS: calc. for $C_{21}H_{36}N_2O_4$: 380.3. Found: 381 (M+H).

Piperidine Intermediate 6:

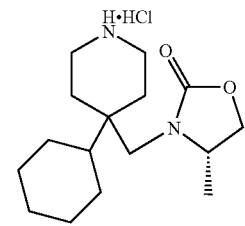

Intermediate 6 was prepared from Intermediate 5 in an analogous manner to the one described for the preparation of Intermediate 3.

MS: calc. for $C_{16}H_{28}N_2O_2$: 280.3. Found: 281 (M+H).

Piperidine Intermediate 7:

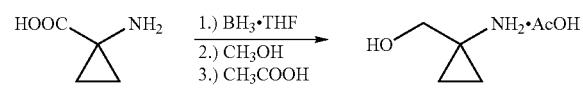

To a suspension of 1-aminocyclopropane-1-carboxylic acid (2.8 g, 27.7 mmol) in THF (20 mL) was added borane-tetrahydrofuran complex (100 mL, 100 mmol) slowly under nitrogen at room temperature. The reaction mixture was stirred at 70° C. overnight, then cooled to 0° C. After addition of methanol (12.2 mL, 300 mmol), the mixture was allowed to stir for 30 min. Then acetic acid (1.6 mL, 27.7 mmol) was added. The reaction mixture was concentrated to provide the title compound as a colorless oil (3.0 g).

Piperidine Intermediate 8:

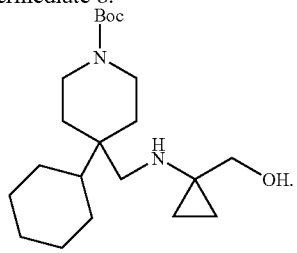

Intermediate 8 was prepared from Intermediate 7 in an analogous manner to the one described for the preparation of Intermediate 1.

MS: calc. for $C_{21}H_{38}N_2O_3$: 366.3. Found: 367 (M+H).

Piperidine Intermediate 9:

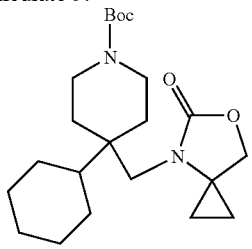

To a solution of Intermediate 8 (0.8 g, 2.18 mmol) in $CH_2Cl_2$ (40 mL) at 0° was added DMAP (0.266 g, 2.18 mmol), DIEA (1.52 mL, 8.74 mmol) and triphosgene (0.648 g, 2.18 mmol). After stirring the reaction mixture for one hour at 0° C., the ice-water bath was removed and the reaction mixture was allowed to stir at room temperature overnight. The mixture was diluted with $CH_2Cl_2$, washed with water and brine, dried over $MgSO_4$ and concentrated to give crude product, which was purified by column chromatography on silica gel (10% $CH_2Cl_2$/EtOAc) to give the title compound as a colorless oil (0.13 g).

ES-MS: calc. for $C_{22}H_{36}N_2O_4$: 392. Found: 393 (M+1).

Piperidine Intermediate 10:

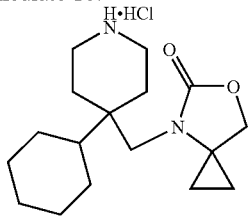

Intermediate 10 was prepared from Intermediate 9 in an analogous manner to the one described for the preparation of Intermediate 3.

MS: calc. for $C_{17}H_{28}N_2O_2$: 292.2. Found: 293 (M+H).

Piperidine Intermediate 11:

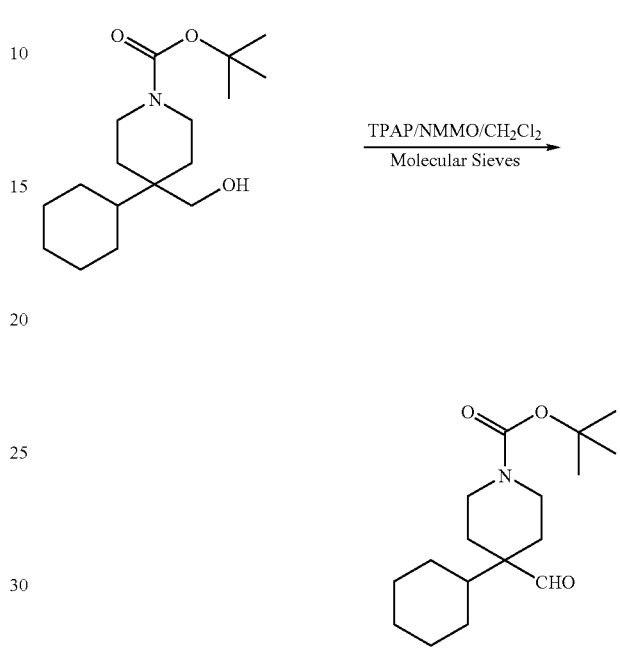

To a solution of the alcohol (9.41 g, 31.6 mmol) in $CH_2Cl_2$ (100 mL) at 0° C. containing molecular sieves (2 g) and 4-methylmorpholine N-oxide (NMMO) (4.449 g, 37.98 mmol) was added TPAP (1.12 g, 3.16 mmol). After stirring the reaction mixture at 0° C. for 0.5 h, the reaction mixture was warmed to room temperature and stirred for an additional 5 h. The reaction mixture was concentrated to half the volume, diluted with hexane (250 mL), filtered through a silica gel pad and concentrated to give pure title compound (9.4 g).

Piperidine Intermediate 12:

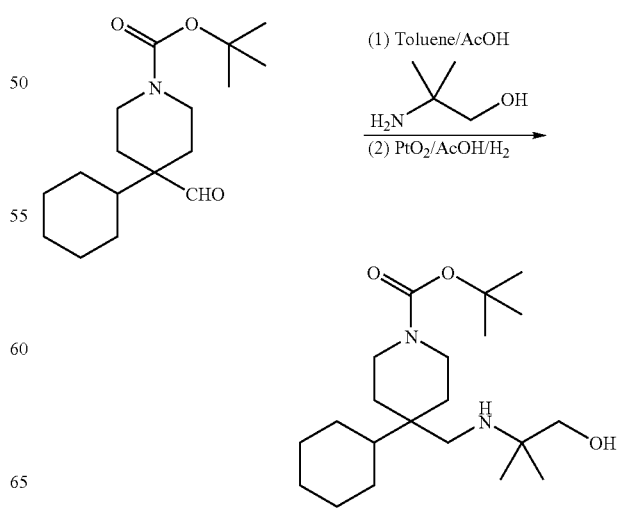

To a solution of the aldehyde (2 g, 6.7 mmol) in toluene (50 mL) was added acetic acid (500 μL) and the aminoalcohol (666 mg, 6.8 mmol). After stirring the reaction mixture at reflux temperature using Dean Stark apparatus for 8 h, the mixture was concentrated and dissolved in acetic acid (30 mL). To the mixture was added PtO$_2$ (500 mg) which was stirred under an atmosphere of H$_2$ overnight. The rection mixture was flushed with nitrogen, filtered and concentrated to give the title compound (2 g).

Piperidine Intermediate 13:

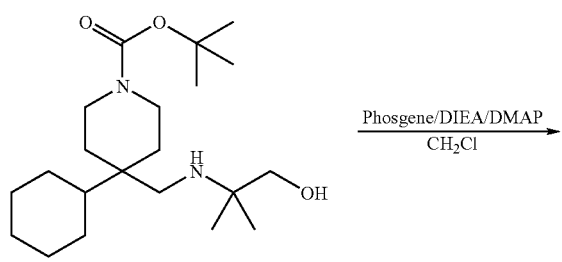

To a solution of the amino alcohol (4.96 g, 13.47 mmol) in CH$_2$Cl$_2$ at 0° C. containing DIEA (6.98 g, 53.9 nmol), DMAP (1.64 g, 13.47 mmol) was added slowly a toluene solution of phosgene (1.93M, 10.47 mL, 20.21 mmol). After stirring the reaction mixture for 1 h at 0° C., the temperature was raised to room temperature and stirred for an additional 2 h. The reaction mixture was diluted with CH$_2$Cl$_2$, washed with water, brine, dried and concentrated. The residue was purified by column chromatography over silica gel (5% EtOAc/CH$_2$Cl$_2$) to give pure product (3.95 g).

Piperidine Intermediate 14:

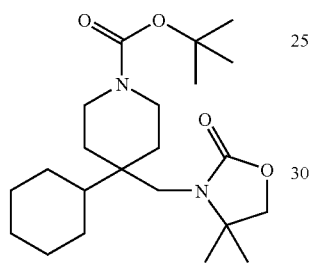

To a solution of Intermediate 13 (3.95 g) in CH$_2$Cl$_2$ was added 5 mL of a saturated HCl solution in EtOAc. After stirring the reaction mixture for 30 min at room temperature, the solvent was removed and the residue lyophilized from a benzene/methanol solution to afford the title compound (3.85 g).

Piperidine Intermediate 15:

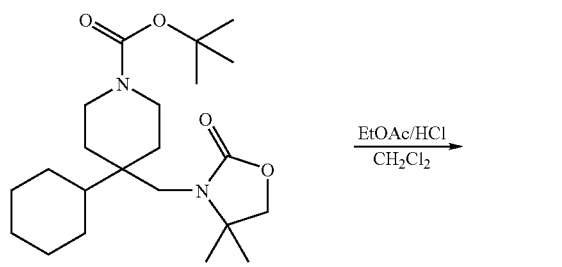

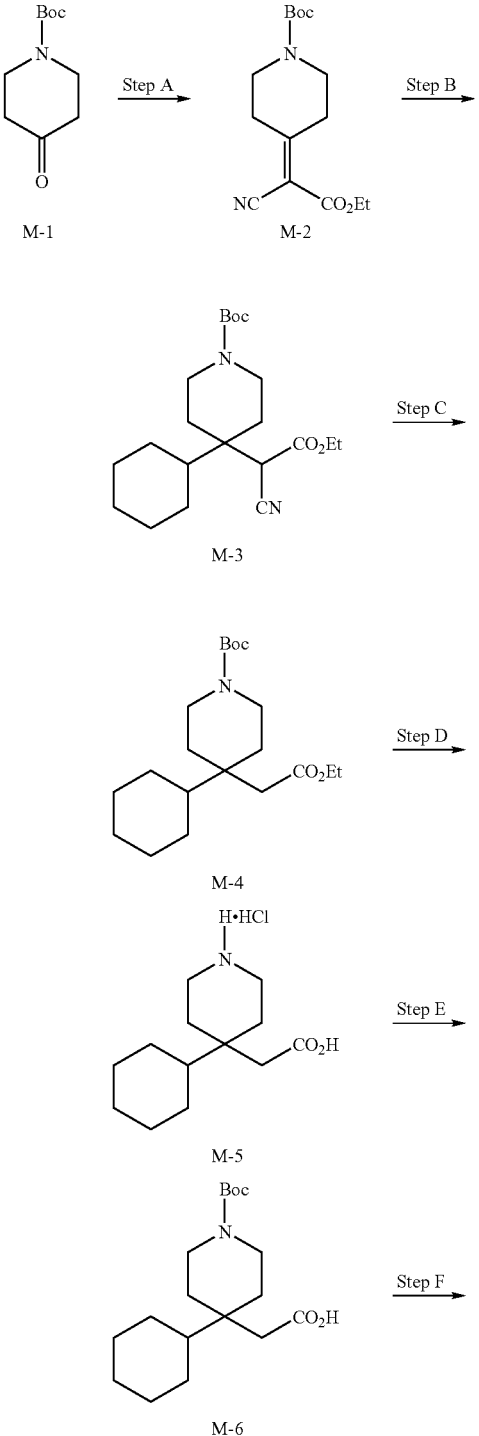

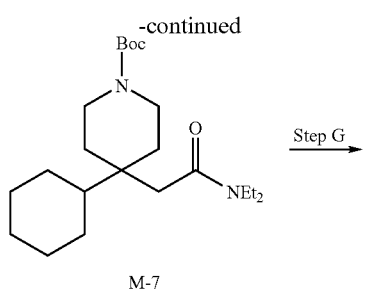

M-7

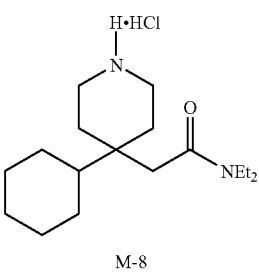

M-8

Step A:

To a 500-mL round-bottom flask equipped with a Dean Stark trap and magnetic stirrer was added 1-Boc-4-piperidone (M-1) (20.0 g, 100 mmol), cyanoacetic acid ethyl ester (10.6 mL, 100 mmol), $NH_4OAc$ (0.77 g, 10 mmol), HOAc (0.57 mL, 10 mmol), and benzene (200 mL). The mixture was stirred at reflux temperature overnight. After cooling to room temperature, the volatiles were removed under reduced pressure, and the residue was purified by flash column chromatography with 20% EtOAc in hexane as eluent to give M-2 as white solid (21.6 g).

ES-MS: Calcd. for $C_{15}H_{22}N_2O_4$: 294. Found: 317 ($M^+$+Na).

Step B:

To a suspension of CuCN (3.28 g, 36.3 mmol) in dry THF (100 mL) was added cyclohexylmagnesium chloride (36.6 mL, 73.2 mmol, 2.0 N in ether). The resulting suspension was stirred at −50° C. for 30 min and then warmed up to room temperature. After stirring for 1 h, a solution of compound M-1 (5.40 g, 18.3 mmol) in 50 mL of THF was cannulated into the mixture over 2 min. The mixture was stirred at −50° C. for 1 h and then kept at −25° C. overnight. The mixture was slowly warmed to −10° C. and quenched with saturated aqueous $NH_4Cl$ (50 mL) and water (50 mL), extracted with EtOAc (2×250 mL). The combined organic extracts were washed three times with water, 1 N HCl, saturated aqueous $NaHCO_3$, dried over $MgSO_4$, filtered, and evaporated to give compound M-3 as a colorless oil (7.12 g).

ES-MS: Calcd. for $C_{21}H_{34}N_2O_4$: 378. Found: 401 ($M^+$+Na).

Step C:

A mixture of M-3 (6.91 g, 18.3 mmol), LiCl (1.09 g, 25.6 mmol), water (1.40 mL), and DMSO (100 mL) was stirred at 160° C. for 1 h. After cooling to room temperature, the mixture was poured into water (800 mL) and extracted with $Et_2O$ (4×250 mL). The combined organic layers were washed with brine, dried over anhydrous $Na_2SO_4$, filtered, and concentrated. The residue was purified by flash column chromatography with 20% EtOAc in hexane as eluent to give compound M-4 as a colorless oil (2.83 g).

ES-MS: Calcd. for $C_{18}H_{30}N_2O_2$: 306. Found: 329 ($M^+$+Na).

Step D:

To a solution of 4.0 N HCl in dioxane (30 mL, 120 mmol) was added M-4 (2.60 g, 8.48 mmol). The mixture was stirred at room temperature for 1 h and the volatiles were removed under reduced pressure. The residue was dissolved in a concentrated HCl (100 mL). The mixture was stirred overnight at reflux temperature. After cooling to room temperature, the volatiles were removed under reduced pressure to give the compound M-5 as a yellow solid (2.42 g).

ES-MS: Calcd. for $C_{13}H_{23}NO_2$: 225. Found: 226 ($MF^+$+1)

Step E:

To a solution of compound M-5 (1.91 g, 8.48 mmol) in dioxane (50 mL) and water (50 mL, containing 5.0 mL 5.0 N NaOH, 25 mmol) was added di-tert-butyl dicarbonate (2.22 g, 10.2 mmol). The mixture was stirred at room temperature for 4 h and the volatiles were removed under reduced pressure. The residue was quenched with a mixture of EtOAc (200 mL) and 1 N HCl (50 mL). The layers were separated and the aqueous layer was extracted three times with EtOAc. The combined organic layers were dried over anhydrous $Na_2SO_4$, filtered, and evaporated to give M-6 as a white solid (2.97 g).

ES-MS: Calcd. for $C_{18}H_{31}NO_4$: 325. Found: 326 ($M^+$+1)

Step F:

Compound M-6 (1.0 g, 3.07 mmol) was dissolved in 30 mL of methylene chloride, and then diethylamine (0.38 mL, 3.68 mmol), DMAP (0.037 g, 0.307 mmol), EDC (1.18 g, 6.14 mmol) were added. The resulting mixture was stirred at room temperature overnight, and then diluted with 20 mL of $CH_2Cl_2$ and washed with 20 mL of 1N HCl solution, 20 mL of saturated $NaHCO_3$ solution, 20 mL of $H_2O$, and 20 mL of saturated NaCl solution. The organic phase was dried over $MgSO_4$, filtered, and evaporated to give M-7 (1.16 g).

ES-MS: Calcd. for $C_{22}H_{40}N_2O_3$: 380. Found: 381 ($M^+$+1).

Step G:

To a solution of 4.0 N HCl in dioxane (30 mL, 120 mmol) was added M-7 (1.16 g, 3.07 mmol). The mixture was stirred at room temperature for 1 h and the volatiles were removed under reduced pressure to give M-8 (0.99 g).

ES-MS: Calcd. for $C_{17}H_{32}N_2O$: 280. Found: 281 ($M^+$+1).

Piperidine Intermediate 16:

Scheme N

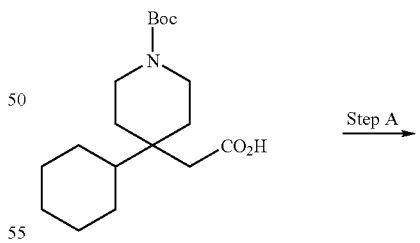

M-6

N-1

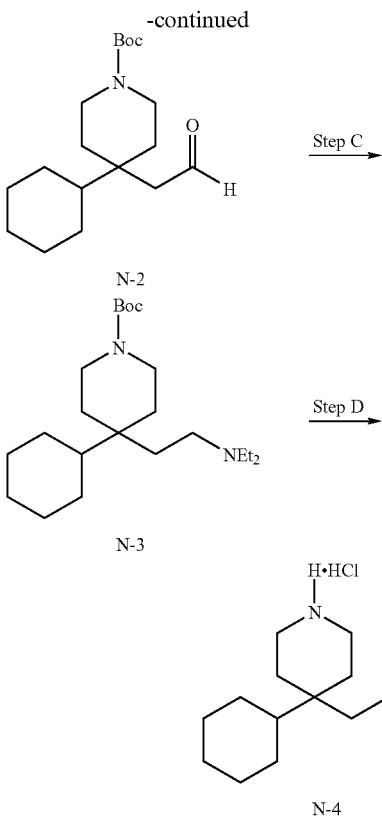

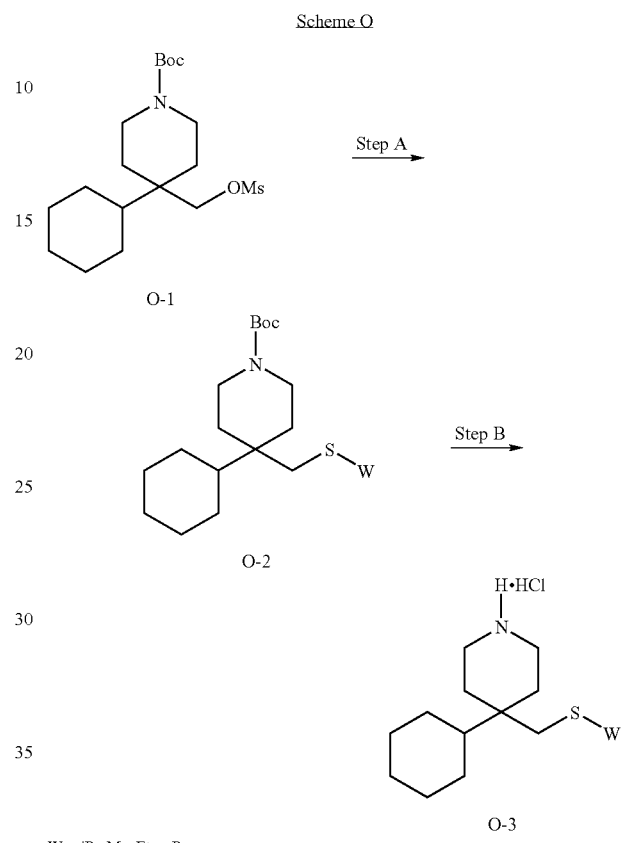

W = iPr, Me, Et, n-Pr, cyclopropylmethyl, or cyclobutyl ture was stirred at room temperature for 1 h and the volatiles were removed under reduced pressure to give N-4 (0.075 g).

ES-MS: Calcd. for $C_{17}H_{34}N_2$: 266. Found: 227 ($M^+$+1).

Piperidine Intermediates 17-21:

Step A:

To a solution of M-6 (0.18 g, 0.554 mmol) in 8.0 mL of dry THF was added borane-dimethyl sulfide complex (1.10 mL, 2.0 N in THF, 2.20 mmol). The mixture was stirred overnight and then quenched with MeOH. The volatiles were removed under reduced pressure to give N-1 (0.11 g).

ES-MS: Calcd. for $C_{18}H_{33}NO_3$, 311. Found: 334 ($M^+$+Na).

Step B:

To a suspension of N-1 (0.11 g, 0.347 mmol), 4-methylmorpholine N-oxide (0.049 mg, 0.416 mmol), and molecular sieve in dry methylene chloride (5.0 mL) was added TPAP (0.012 g, 0.035 mmol). After stirring for 30 min, the mixture was filtered through a pad of silica gel and washed with ether. The organic solution was evaporated to give compound N-2 as an oil (0.11 g).

ES-MS: Calcd. for $C_{18}H_{31}NO_3$, 309. Found: 332 ($M^+$+Na).

Step C:

To a solution of N-2 (0.11 g, 0.35 mmol) in 3.0 mL of methylene chloride was added diethylamine (0.072 mL, 0.70 mmol) and molecular sieves. After stirring for about 5 min, Na(OAc)$_3$BH (0.22 mg, 1.05 mmol) was added and the mixture was stirred for 6 h at room temperature. After filtration of molecular sieves, the mixture was diluted with methylene chloride, washed twice with saturated aqueous NaHCO$_3$ solution, dried over anhydrous Na$_2$SO$_4$, filtered, and evaporated to give N-3 (0.080 g).

ES-MS: Calcd. for $C_{22}H_{42}N_2O_2$: 366. Found: 367 ($M^+$+1).

Step D:

To a solution of 4.0 N HCl in dioxane (10 mL, 40 mmol) was added compound N-3 (0.080 g, 0.218 mmol). The mix- Step A:

To a stirred solution of tert-butyl 4-cyclohexyl-4-{[(methylsulfonyl)oxy]methyl}piperidine-1-carboxylate (O-1) (3 g, 8.0 mmol) in DMF (30 mL) at room temperature was added sodium 2-methyl-2-propanethiolate (0.78 g, 8.0 mmol). The resultant suspension was stirred at 60° C. for 18 h and then poured into water (150 mL) and extracted with diethyl ether (3×100 mL). The combined organic extracts were washed with brine, dried over Na$_2$SO$_4$ and concentrated. Flash chromatography over silica (5% EtOAc in hexane) yielded O-2 (W=iPr) as a clear colorless oil (2.4 g).

ES-MS: calcd for $C_{20}H_{37}NO_2S$, 355.25. Found: 378 ($M^+$+Na).

Step B:

To a stirred solution of O-2 (W=iPr) (2.4 g, 6.7 mmol) in methylene chloride (10 mL) at room temperature was added HCl (5N in dioxane) (50 mL). The resultant solution was stirred at room temperature for 1 h. Volatiles were removed in vacuo to furnish O-3 (W=iPr) as a clear colorless gum (1.9 g).

ES-MS: calcd for $C_{15}H_{29}NS$, 255.20. Found: 256 ($M^+$+1).

The piperidine intermediates O-3 (W=Me, Et, n-Pr, cyclopropylmethyl, and cyclobutyl) were prepared in an analogous manner to the one described for the preparation of 4-cyclohexyl-4-[(isopropylthio)methyl]piperidinium chloride (O-3, W=iPr).

O-3 (W=Et): ES-MS: calcd for $C_{14}H_{27}NS$: 241.19. Found: 242 ($M^++1$).

O-3 (W=Me): ES-MS: calcd for $C_{13}H_{25}NS$: 227.17. Found: 228 ($M^++1$).

O-3 (W=n-Pr): ES-MS: calcd for $C_{15}H_{29}NS$: 255.20. Found: 256 ($M^++1$).

O-3 (W=cyclopropylmethyl): ES-MS: calcd for $C_{16}H_{29}NS$: 267.20. Found: 268 ($M^++1$).

O-3 (W=cyclobutylthio): ES-MS: calcd for $C_{16}H_{29}NS$: 267.20. Found: 268 ($M^++1$).

Piperidine Intermediate 22:

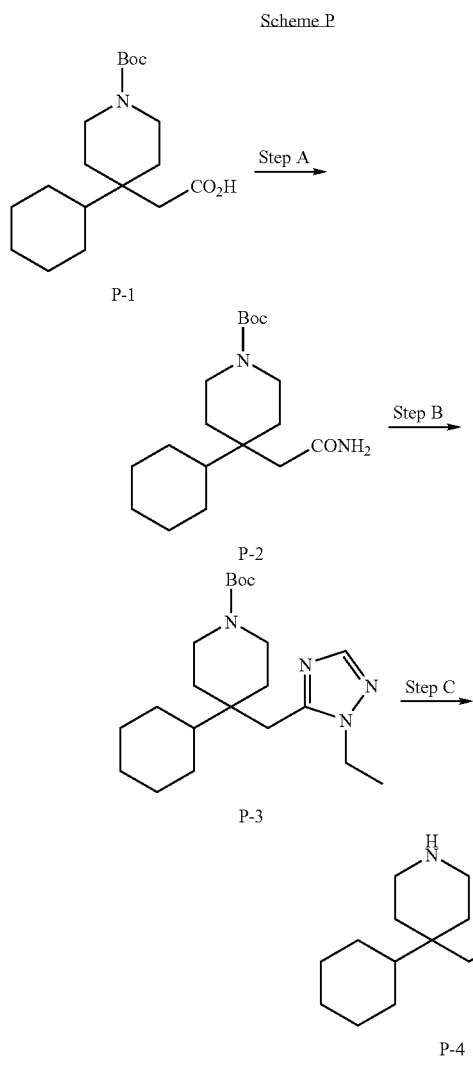

Step A:

To a solution of P-1 (0.745 g, 2.072 mmol) in methylene chloride (40 mL) at 0° C. was added DMF (1 mL) followed by the dropwise addition of oxalyl chloride (1.14 mL of 2M solution in methylene chloride, 2.28 mmol). The reaction was warmed to room temperature over one h, then re-cooled to 0° C. before transferring to a rapidly stirring saturated aqueous ammonium hydroxide solution (15 mL). The resulting mixture was then poured into methylene chloride (40 mL) and diluted with 1N NaOH (40 mL). The layers were separated and the aqueous phase was extracted three times with methylene chloride. The combined organics were then washed with water and brine, dried (sodium sulfate) and the volatiles removed in vacuo. Flash chromatography over silica (25% acetone/methylene chloride) yielded P-2 as a white foam (0.615 g).

ES-MS: calcd for $C_{21}H_{30}N_2O_3$: 358.23. Found 359 ($M^++1$).

Step B:

A solution of P-2 (0.150 g, 0.84 mmol) in N,N-dimethylformamide dimethyl acetal (1 mL) was refluxed at 120° C. for 2 h, then cooled to room temperature. The reaction was then concentrated and the residue was dissolved in acetic acid (1 mL). Ethyl hydrazine was then added and the reaction was heated at 95° C. for 3.5 h. The volatiles were then removed in vacuo and the reaction was partitioned between sodium bicarbonate and ethyl acetate. The organics were collected, washed with water and brine, dried (sodium sulfate), and the volatiles removed in vacuo. Purification by flash chromatography (0-15% acetone in methylene chloride) yielded P-3 as a pale yellow oil (79 mg).

ES-MS: calcd for $C_{24}H_{34}N_4O_2$: 410.27. Found 411 ($M^++1$).

Step C:

To a solution of P-3 (79 mg) in methylene chloride was added 30% HBr in acetic acid (5 mL) and the reaction was stirred for two h. The volatiles were removed, and the reaction was partitioned between 1N NaOH and methylene chloride. The organics were dried (sodium sulfate) and evaporated to afford P-4 as an oil (59 mg). ES-MS: calcd for $C_{16}H_{28}N_4$: 276.23; Found 277 ($M^++1$).

Piperidine Intermediate 23:

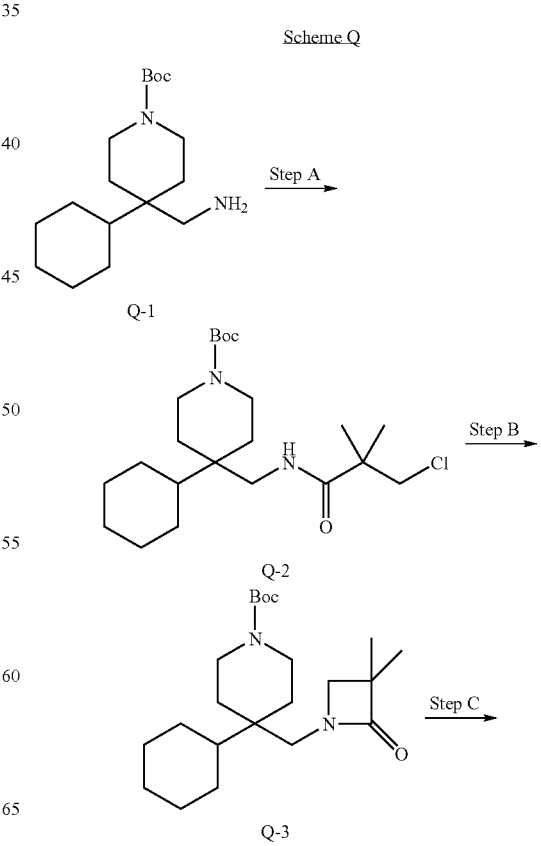

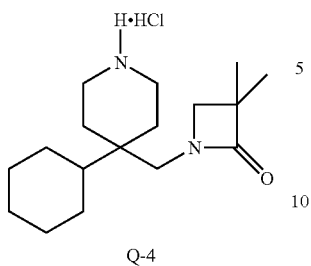

Q-4

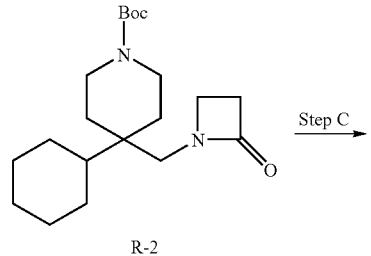

R-2

Step A:

To a stirred solution of Q-1 (1.33 g, 4.5 mmol) in methylene chloride (12 mL) was added DMAP (0.14 g, 1.1 mmol) and 3-chloropivaloyl chloride (0.87 g, 5.6 mmol). The mixture was stirred 1 h, diluted with methylene chloride, washed with 1N HCl, the organic layer dried over $MgSO_4$ and the solvent removed in vacuo to provide 2.1 g of Q-2 as an oil. ES-MS calc. for $C_{22}H_{39}ClN_2O_3$: 414. Found 415 (M+H).

Step B:

To a stirred solution of Q-1 (2.25 g, 5.42 mmol) in DMF (15 mL) was added NaH (0.52 g, 21.7 mmol) and heated to 70° C. for 16 h. The mixture was quenched with MeOH and then water. The mixture was concentrated, diluted with EtOAc, washed with 2N HCl, brine, dried over $MgSO_4$ and evaporated. The product was purified by preparative HPLC (C18, 20×100 mm, 50-100% acetonitrile) to provide 850 mg of Q-3 as a yellow solid. ES-MS calc. for $C_{22}H_{38}N_2O_3$: 378. Found 379 (M+H).

Step C:

Compound Q-3 (1.05 g, 1.92 mmol) was treated with HCl-EtOAc solution at room temperature for 30 min. The mixture was evaporated to provide 690 of Q-4 as a solid. ES-MS calc. for $C_{17}H_{30}N_2O$: 278. Found 279 (M+H).

Piperidine Intermediate 24:

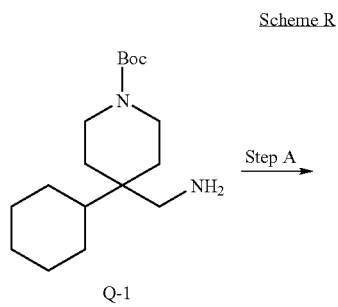

R-3

Step A:

Compound R-1 was synthesized in a manner similar as Q-2, but using 3-chloropropionyl chloride. ES-MS calc. for $C_{20}H_{35}ClN_2O_3$: 386. Found 387 (M+H).

Step B:

Compound R-2 was synthesized from R-1 in a manner similar as Q-3. ES-MS calc. for $C_{20}H_{34}N_2O_3$: 350. Found 351 (M+H).

Step C:

Compound R-3 was synthesized from R-2 in a manner similar as Q-4. ES-MS calc. for $C_{15}H_{26}N_2O$: 250. Found 251 (M+H).

Piperidine Intermediate 25:

Scheme R

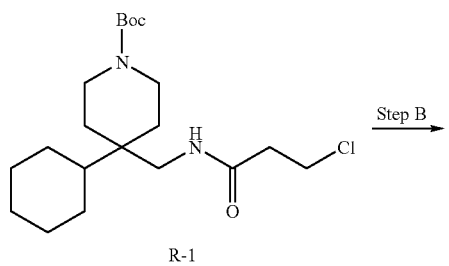

Scheme S

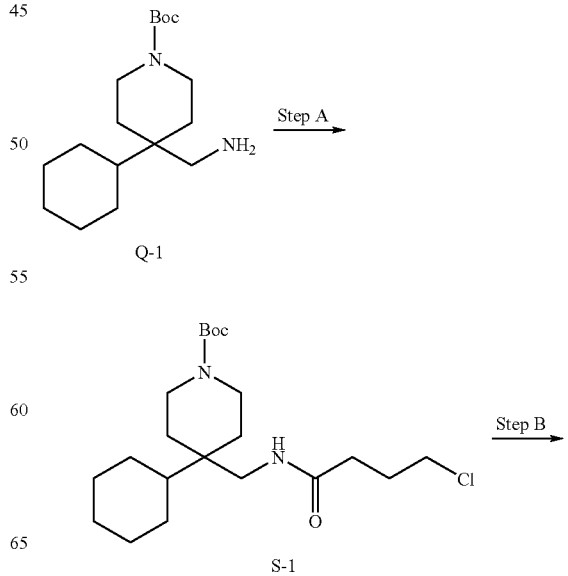

-continued

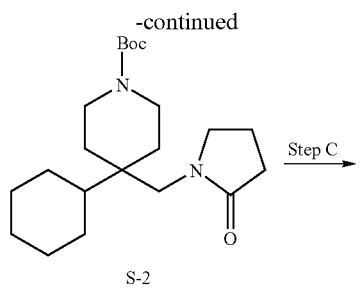

S-2

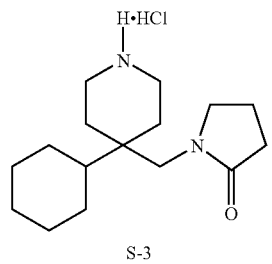

S-3

Step A:

Compound S-1 was synthesized in a manner similar as Q-2, but using 4-chlorobutyryl chloride. ES-MS calc. for $C_{21}H_{37}ClN_2O_3$: 400. Found 401 (M+H).

Step B:

Compound S-2 was synthesized from S-2 in a manner similar to Q-3. ES-MS calc. for $C_{21}H_{36}N_2O_3$: 364. Found 365 (M+H).

Step C:

Compound S-3 was synthesized from S-2 in a manner similar to Q4. ES-MS calc. for $C_{16}H_{28}N_2O$: 264. Found 265 (M+H).

Piperidine Intermediate 26:

Scheme T

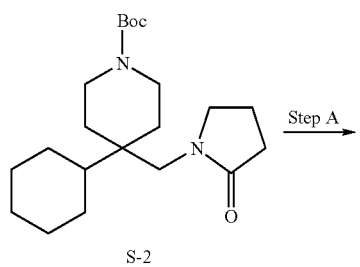

S-2

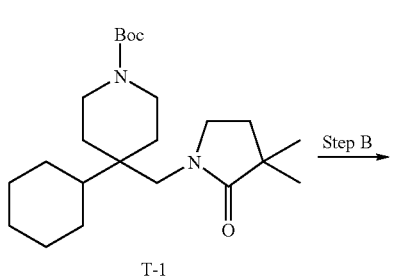

T-1

-continued

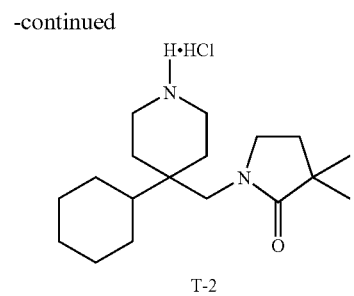

T-2

Step A:

To a stirred solution of S-2 (2.3 g, 6.3 mmol) in THF (20 mL) cooled to −78° C. was added lithium diisopropylamide (LDA) (2M solution in THF) (3 eq) slowly via syringe over 20 min and stirring was continued for 1 h. Iodomethane was added and the mixture was stirred for 1 h. The reaction mixture was warmed to room temperatur and stirring was continued an additional 30 min. Subsequently, the reaction mixture was cooled again to −45° C. and another 1.5 eq. of LDA added. The mixture was stirred 15 min, then an additional 1 eq. of iodomethane was introduced to the reaction mixture and the stirring continued 1 h. The reaction was quenched with water, concentrated and partitioned between EtOAc/2N HCl, washed with brine, dried over MgSO$_4$, filtered and concentrated. The residue was chromatographed (silica, 1:4 EtOAc/hexane) to provide 720 mg of T-1 as a white solid. ES-MS calc. for $C_{23}H_{40}N_2O_3$: 392. Found 393 (M+H).

Step B:

Compound T-2 was prepared from T-1 in a manner similar to Q-4. ES-MS calc. for $C_{18}H_{32}N_2O$: 292. Found 293 (M+H).

Piperidine Intermediate 27:

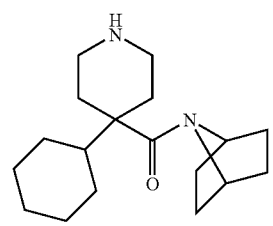

To a stirred solution of 4-cyclohexyl-piperidine-1,4-dicarboxylic acid 1-monobenzyl ester (682 mg, 1.98 mmol), 7-aza-bicyclo[2.2.1]heptane (220 mg, 1.65 mmol), PyBrop (1.53 g, 3.29 mmol) and DMAP (120 mg, 0.99 mmol) in methylene chloride (3.0 mL) was added DIEA (691 mg, 5.35 mmol). The solution was stirred 2 h, concentrated, partitioned between EtOAc and 2N HCl (2×10 mL). The organic layer was washed with brine, dried over MgSO$_4$, filtered and the solvent was removed in vacuo to provide the title compound. ES-MS calc. for $C_{26}H_{36}N_2O_3$: 424. Found: 425 (M+H). The benzyl carbamate protecting group was removed by catalytic hydrogenation.

Piperidine Intermediate 28:

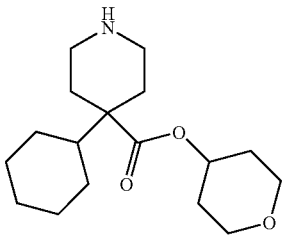

A stirred solution of 4-cyclohexyl-piperidine-1,4-dicarboxylic acid 1-monobenzyl ester (3.66 g, 10.6 mmol) and thionyl chloride was refluxed for 4 h. The reaction mixture was then concentrated in vacuo and diluted with methylene chloride (20 mL). DIEA (2.74 g, 21 mmol) and tetrahydropyranol (2.2 g, 21 mmol) were added and the mixture refluxed for 16 h. The reaction mixture was concentrated, partitioned between with EtOAc and 2N HCl, washed with brine, dried over MgSO$_4$ and the solvent removed in vacuo to provide the title compound. ES-MS calc. for $C_{25}H_{35}NO_5$: 429. Found: 430 (M+H). The benzyl carbamate protecting group was removed by catalytic hydrogenation.

Piperidine Intermediate 29:

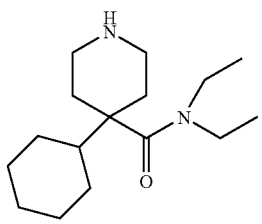

The title compound was synthesized in a manner similar to Intermediate 27 but using diethylamine in place of 7-azabicyclo[2.2.1]heptane.

ES-MS calc. for $C_{24}H_{36}N_2O_3$: 400. Found: 401 (M+H).

Piperidine Intermediates 30 and 31:

Intermediate 30:

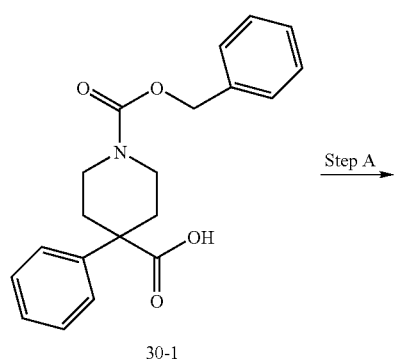

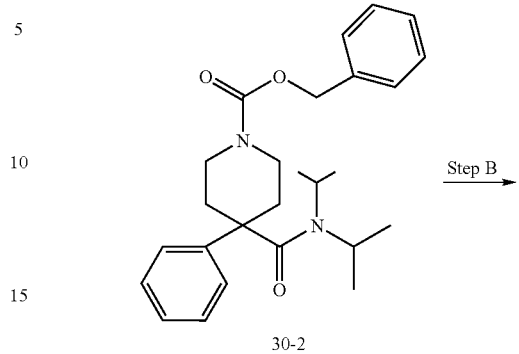

Step A:
To acid (30-1) (10 g, 29.5 mmole) was added thionyl chloride (30 ml). The reaction mixture was heated 90° C. for 7 hrs, followed by the removal of thionyl chloride by distillation. The resulting residue was dissolved in 1,2-dichloroethane (50 ml), cooled to 0° C., then diisopropylamine (20.7 ml, 147.5 mmole) and DIEA (10.3 ml, 59.0 mmole) were added. Then reaction mixture was warmed up to room temperature, and heated to 70° C. overnight. Reaction mixture was then concentrated, and the resulting residue was dissolved in CH$_2$Cl$_2$, washed with HCl (0.1 N), water and brine, dried over MgSO$_4$ and concentrated to give brown oil. The oil which was separated by column chromatograph (hexane: ethyl acetate=8:1) to give the Intermediate (30-2) as a brown oil. ESI-MS calc. for $C_{26}H_{34}N_2O_3$: 422.3. Found: 423.2 (M+H)

Step B:
To a solution of Intermediate (30-2) (3.8 g, 9.0 mmole) in EtOH (120 ml) was added HCl (4.5 ml, 18 mmole, 4.0M in dioxane), and Pd(OH)$_2$ (1.5 g). The mixture was hydrogenated at 45 psi in a Parr apparatus for 17 hrs. Then the catalyst was filtered off through celite, and the filtrate was concentrated to give Intermediate (30-3) as a brown solid. ESI-MS calc. for $C_{18}H_{28}N_2O$: 288.2. Found: 289(M+H)

Step C:
To a solution of Intermediate (30-3) (1.2 g, 3.7 mmole) in MeOH (100 ml) was added HCl (4.0 M in dioxane, 2.8 ml, 11.1 mmole), and Rh/Al$_2$O$_3$ (1.2 g). The mixture was hydrogenated at 100 psi at 70° C. in a Parr apparatus for 18 hrs. Then the catalyst was filtered off through celite, and the filtrate was concentrated to give Intermediate (30-4) as a white solid. ESI-MS calc. for C$_{18}$H$_{34}$N$_2$O: 294.3. Found: 295.2 (M+H)

Intermediate 31:

Route A:

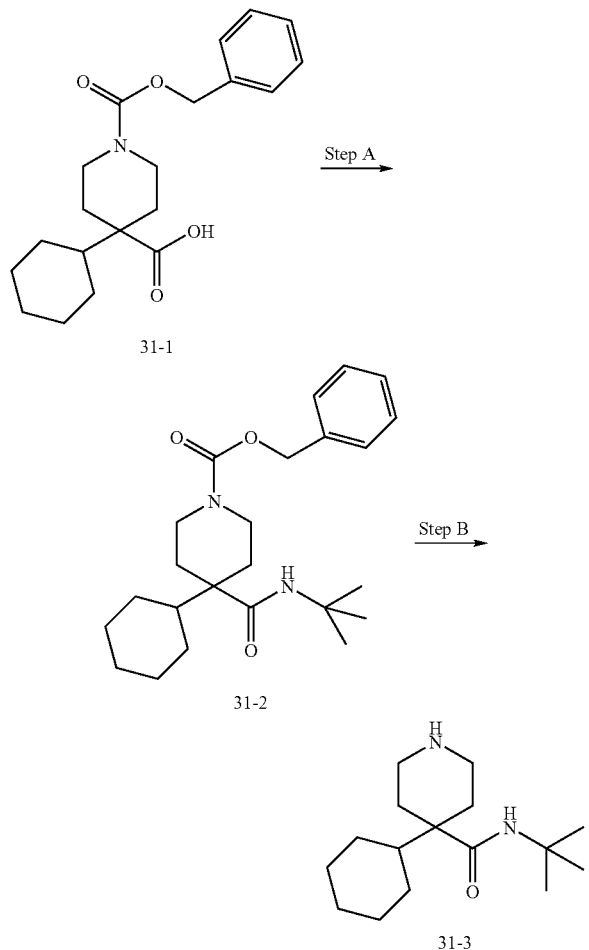

mmol) was added. The mixture was stirred at room temperature for 45 min (reaction monitored by TLC), and then diethyl ether was added. The resulting precipitate was filtered and washed with ether. The solid was dissolved in ethyl acetate and washed with 1N NaOH solution, and the aqueous layer was extracted with EtOAc. The combined organic phases were dried over K$_2$CO$_3$, filtered, and concentrated to give Intermediate 31-3 as a white solid. Mass spectrum: Calcd for C$_{16}$H$_{30}$N$_2$O: 266.24. Found: 267 (M$^+$+1).

Route B:

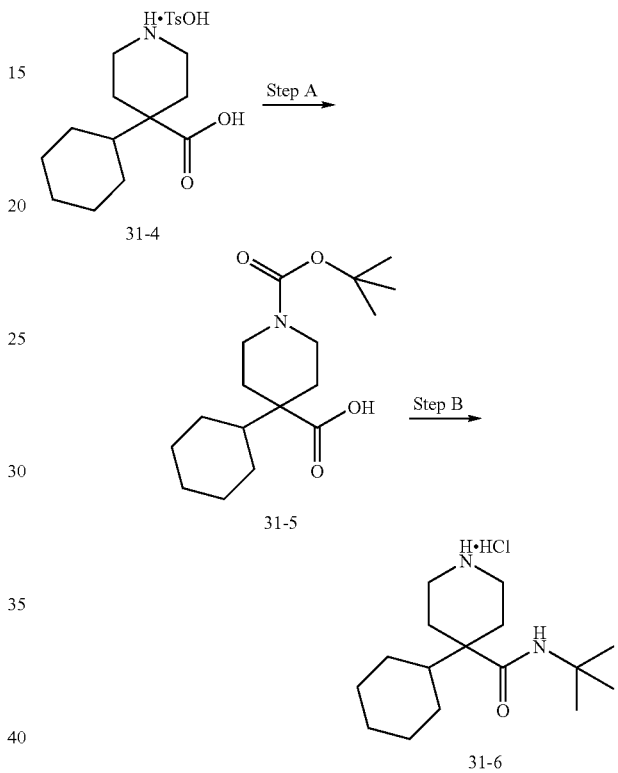

Step A:

N-(Benzyloxycarboyl)-4-cyclohexyl-piperidine-4-carboxylic acid 31-1 (2.5 g, 7.24 mmol) was dissolved in 36 mL of CH$_2$Cl$_2$ and cooled at 0° C. in an ice-H$_2$O bath. Oxalyl chloride (2.0 M solution in CH$_2$Cl$_2$, 3.98 mL, 7.96 mmol) was then added dropwise followed by the addition of 1-2 drops of DMF. This mixture was stirred at 0° C. for 2 h and then concentrated with toluene. The residue was dissolved in CH$_2$Cl$_2$ and cooled at 0° C. in an ice-H$_2$O bath, and then t-butylamine (2.28 mL, 21.72 mmol) was added dropwise. The reaction mixture was then stirred at 0° C. for 2 h, warmed to room temperature, and stirred at room temperature overnight. The resulting mixture was then diluted with CH$_2$Cl$_2$ and washed with brine, dried over MgSO$_4$, filtered, and concentrated to give Intermediate 31-2 as a solid. Mass spectrum: Calcd for C$_{24}$H$_{36}$N$_2$O$_3$: 400.27. Found: 401 (M$^+$+1).

Step B:

Intermediate 31-2 (7.24 mmol) was dissolved in 30 mL of CH$_2$Cl$_2$ and then 30% HBr in acetic acid (7.2 mL, 36.15

Step A:

A mixture of piperidine tosylate 31-4 (4 kilograms), THF (32 L), and 1N NaOH (24 L) was chilled to 10° C., then a solution of di-tert-butyl dicarbonate (2.55 kilograms) in THF (2 L) was slowly added, maintaining a temperature below 17° C. The di-tert-butyl dicarbonate solution was rinsed in with THF (100 mL), then 5N NaOH (4 L) was added, maintaining the temperature below 20° C., to achieve a pH of 12. The mixture was aged at ambient temperature overnight. The THF was removed via distillation, and the aqueous solution was acidified with 2N HCl (20 L), precipitating the product. The product was collected via filtration and was washed with cold water (15 L). The material was dried at 40° C. in vacuo with a nitrogen bleed (250 torr) to afford 31-5 as a solid.

Step B:

To a solution of intermediate 31-5 in MeOH (300 mL) was added 5% Rh/alumina (12.5 g, 25 weight %) followed by a MeOH rinse (100 mL). The mixture was hydrogenated at 70 psi and 70° C. for 8 h, then cooled to ambient temperature and the catalyst was removed by filtration. After a MeOH cake wash (100 mL), the supernatant was evaporated to a solid. The solid was slurried in MTBE (500 mL) and DMF was added (5 mL). The mixture was cooled to about 0° C. to 8° C., and oxalyl chloride (17.1 mL, 193 mmol) was added over 45 min. The resulting solution was stirred at r.t. until gas evolution ceased (18 h). The MTBE was evaporated, and the oil was flushed twice with toluene (100 mL). The acid chloride was added to a vigorously stirred mixture of t-butyl amine (84 mL, 805 mmol), potassium carbonate (44 g, 321 mmol, 2 eq), MTBE (500 mL), and water (250 mL). The acid chloride was washed in with MTBE (250 mL), and the mixture was allowed to stir for 4 h. The aqueous phase was remove; the organic layer was washed with 2N HCl (350 mL) and water (200 mL), and then evaporated and flushed with MeOH. The residue was dissolved in MeOH (500 mL), and concentrated HCL was added (50 mL), then the solution was heated to 40-45° C. for 4 h. The solution was evaporated and flushed with ethanol (2×250 mL) to remove residual acid, then THF (2×250 mL) to remove residual EtOH. After dissolving in THF (300 mL) and seeding, intermediate 31-6 crystallized as the HCl salt. After at least an 18 h age, MTBE was added (600 mL) as anti-solvent over 3 h, then the mixture was stirred for an additional 18 h. Intermediate 31-6 was collected with a 2:1 MTBE:THF wash (100 mL) and dried at 40° C. in vacuo to give a solid.

Scheme U

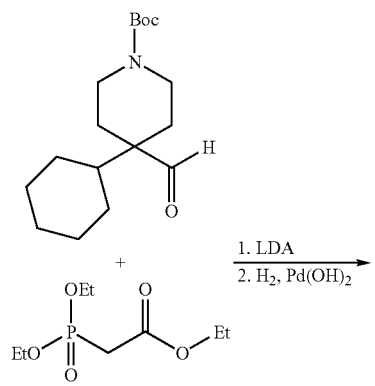

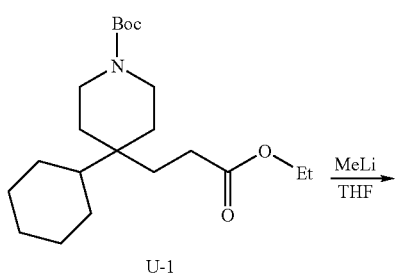

U-1

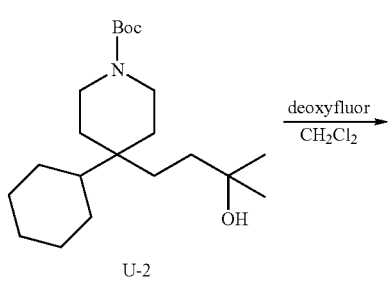

U-2

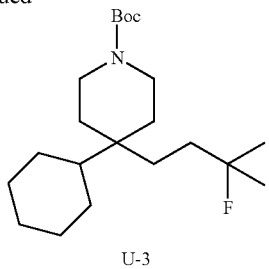

U-3

Step A:

A mixture of 4-cyclohexyl-4-formyl-N-(tertbutyloxycarbonyl)-piperidine (3.7 g, 14.3 mmol) and diethyl t-butylphosphonoacetate (3.2 g, 14.3 mmol) in 45 mL tetrahydrofuran was stirred at room temperature. 2M LDA (0.26 mL, 0.52 mmol) was slowly added via syringe and stirring continued for 4 h. The reaction mixture was quenched with saturated aqueous NH$_4$Cl, concentrated, extracted with EtOAc. The organic extract was washed with brine, dried over MgSO$_4$ and concentrated to afford an orange residue which was purified by flash chromatography on silica gel using hexane/EtOAc as eluent. The product (380 mg) and Pd-C (0.41 g) in 75 mL ethanol was stirred under a balloon of hydrogen gas for 4 h. The catalyst was removed by filtration, and the filtrate concentrated to provide U-1.

ES-MS calc. for $C_{21}H_{37}NO_4$: 367. Found: 368 (M+H).

Step B:

To a stirred mixture of U-1 (3.00 g, 8.2 mmol), in tetrahydrofuran (35 mL) at −45° C. was added methyllithium (3 eq. at 1.4M in THF) via syringe. The mixture was stirred an additional 30 min, quenched with aq. NH$_4$Cl and warmed to room temperature. The mixture was concentrated, diluted with EtOAc and washed with brine. The organic layer was dried over MgSO$_4$, filtered and evaporated to provide U-2. ES-MS calc. for $C_{21}H_{39}NO_3$: 353. Found: 354 (M+H).

Step C:

To a stirred mixture of bis-(2-methoxyethyl)-aminosulfur trifluoride (249.2 mg, 1.13 mmol) and methylene chloride (2 mL) at −78° C. was added a solution of U-2 (360 mg, 1.02 mmol) in methylene chloride (4 mL). Stirring was continued for 2 h, and the mixture was warmed to room temperature and stirred an additional hour. The reaction was quenched with saturated aqueous sodium hydrogencarbonate and extracted with methylene chloride. The organic layer was dried over Na$_2$SO$_4$, filtered and evaporated to afford the title compound. ES-MS calc. for $C_{21}H_{38}FNO_2$: 355. Found: 356 (M+H).

Scheme V

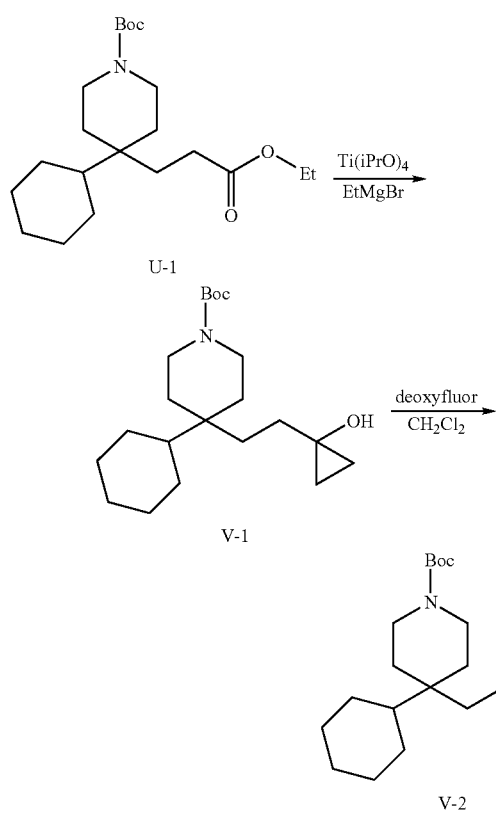

Step A:

To a mixture of U-1 (380 mg, 1.04 mmol) and titanium tetraisopropoxide (75.53 mg, 0.26 mmol) in anhydrous ethyl ether (5 mL) at room temperature was added ethylmagnesium bromide (2.1 eq at 1M in THF). The reaction mixture was stirred an additional 5 h and then quenched with 10% $H_2SO_4$. The organic layer was separated, dried over $MgSO_4$, filtered and evaporated to provide V-1. ES-MS calc. for $C_{21}H_{37}NO_3$: 351. Found: 352 (M+H).

Step B:

Compound V-2 was synthesized from V-1 in a manner similar to as U-3. ES-MS calc. for $C_{21}H_{36}FNO_2$: 353. Found: 354 (M+H).

Preparation of Piperidine Urea Intermediates

Intermediate 32:

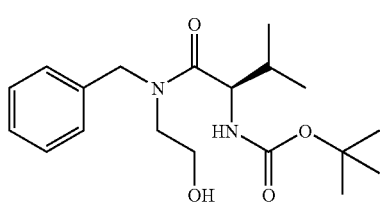

32

Boc-(D)-valine (2.0 g, 9.20 mmol) was dissolved in 42.0 mL of $CH_2Cl_2$, and then N-benzyl ethanolamine (1.27 g, 8.37 mmol), EDC (1.76 g, 9.20 mmol), HOBt (1.24 g, 9.20 mmol), and DIEA (5.83 mL, 33.50 mmol) were added. The resulting mixture was stirred at room temperature overnight, and then diluted with 100 mL of $CH_2Cl_2$ and washed with 50 mL of 1 N HCl, 50 mL of saturated $NaHCO_3$, 50 mL of saturated NaCl solution, dried over $MgSO_4$, filtered, and concentrated to give a yellow oil. The crude product was purified by column chromatography (30:1 to 3:1 methylene chloride-acetone) to give compound 32 as a clear oil.

Intermediates 32 a-g were prepared in a manner similar to intermediate 32.

|  | R | * | Parent ion (M + H) |
|---|---|---|---|
| 32a | i-Pr | R | 351 |
| 32b | i-Pr | S | 351 |
| 33c | i-Bu | S | 265 (M − Boc) |
| 34d | Et | S | 337 |
| 35e | Me | S | 323 |
| 35f | di-Me |  | 337 |
| 35g | cyclopropyl |  | 335 |

Intermediate 33:

33

Intermediates 33 a-b were prepared in a manner similar to intermediate 32.

|  | * | Parent ion (M + H) |
|---|---|---|
| 33a | R | 363 |
| 33b | S | 363 |

Intermediate 34:

34

Compound 33 (1.60 g, 4.56 mmol) was dissolved in 11.4 mL of $CH_2Cl_2$ and 11.4 mL of trifluoroacetic acid. This solution was stirred for 30 min at room temperature and then concentrated, washed with 20 mL of 1 N NaOH solution, dried over $K_2CO_3$, filtered and concentrated. This residue was dissolved in 46 mL of THF, and triphenyl phosphine (1.55 g, 5.93 mmol) and DEAD (0.93 mL, 3.93 mmol) were added.

This mixture was stirred at room temperature overnight. This mixture was concentrated and purified by column chromatography (8:1 to 4:1 EtOAc-MeOH) to give compound 34 as a clear oil.

Intermediates 34 a-g were prepared in a manner similar to intermediate 34.

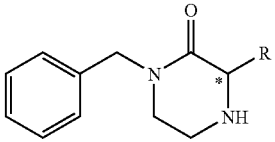

| | R | * | Parent ion (M + H) |
|---|---|---|---|
| 34a | i-Pr | R | 233 |
| 34b | i-Pr | S | 233 |
| 34c | i-Bu | S | 247 |
| 34d | Et | S | 219 |
| 34e | Me | S | 205 |
| 34f | di-Me | | 219 |
| 34g | cyclopropyl | | 217 |

Intermediate 35:

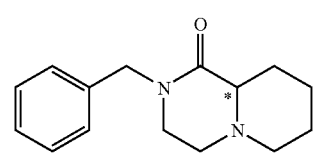

Intermediates 35 a-b were prepared in a manner similar to intermediate 34.

| | * | Parent ion (M + H) |
|---|---|---|
| 35a | R | 245 |
| 35b | S | 245 |

Intermediate 36:

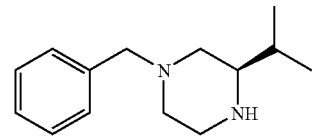

Compound 34 (1.03 g, 4.44 mmol) was dissolved in 10 mL of THF and 1.0 M LAH in THF solution (12.9 mL, 12.9 mmol) was added. This reaction mixture was refluxed overnight. After cooling to room temperature, the mixture was quenched slowly with H$_2$O (0.5 mL), 10% NaOH solution (0.75 mL), and H$_2$O (1.2 mL). The residue was diluted with 21 mL of ethyl ether and stirred for 1 h at room temperature. The solid was filtered and washed successively with ethyl ether, CH$_2$Cl$_2$, and ethyl ether. The combined filtrate was dried over K$_2$CO$_3$, filtered, and concentrated to give an oil. Purification by column chromatography (3% to 20% MeOH—CH$_2$Cl$_2$) prepared compound 36 as a clear oil.

Intermediates 36 a-f were prepared in a manner similar to intermediate 36.

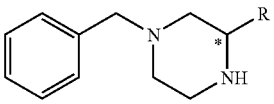

| | R | * | Parent ion (M + H) |
|---|---|---|---|
| 36a | i-Pr | R | 219 |
| 36b | i-Pr | S | 219 |
| 36c | i-Bu | S | 233 |
| 36d | Et | S | 205 |
| 36e | Me | S | 191 |
| 36f | di-Me | | 205 |

Intermediate 37:

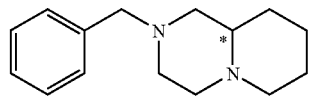

Intermediates 37 a-b were prepared in a manner similar to intermediate 36.

| | * | Parent ion (M + H) |
|---|---|---|
| 37a | R | 231 |
| 37b | S | 231 |

Intermediate 38:

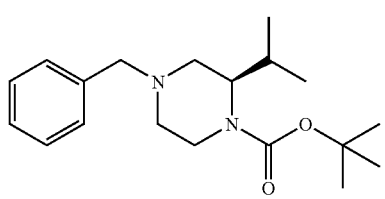

To a solution of compound 36 (0.41 g, 1.86 mmol) in 9.3 mL of CH$_2$Cl$_2$ was added Boc-anhydride (0.45 g, 2.05 mmol), and stirred at room temperature overnight. The mixture was concentrated and purified by column chromatography (10% EtOAc-hexane) to give compound 38 as a clear oil.

Intermediates 38 a-f were prepared in a manner similar to intermediate 38.

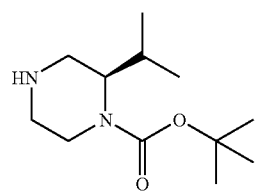

41

Compound 38 (0.40 g, 1.25 mmol) was dissolved in 6.3 mL of MeOH and 10% Pd/C (0.04 g) was added, and then stirred at room temperature under H$_2$ overnight. This mixture was filtered through Celite using CH$_2$Cl$_2$ and concentrated to give compound 41 as an oil.

Intermediates 41 a-g were prepared in a manner similar to intermediate 41.

39

|  | R | * | Parent ion (M + H) |
|---|---|---|---|
| 38a | i-Pr | R | 319 |
| 38b | i-Pr | S | 319 |
| 38c | i-Bu | S | 333 |
| 38d | Et | S | 305 |
| 38e | Me | S | 291 |
| 38f | di-Me |  | 305 |

Intermediate 39:

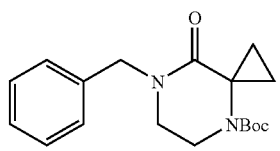

Compound 34 g (1.08 g, 5.00 mmol) was diluted with 25 mL of CH$_2$Cl$_2$ and then Boc-anhydride (1.20 g, 5.50 mmol) was added. The resulting mixture was stirred at room temperature overnight. The mixture was then concentrated and purified by column chromatography (10-25% EtOAc-hexane) to give compound 39 as a clear oil. ES-MS: Calcd. for C$_{18}$H$_{24}$N$_2$O$_3$: 316.39. Found: 217 (M–Boc+1).

Intermediate 40:

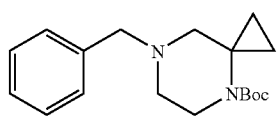

Compound 39 (1.20 g, 3.79 mmol) was dissolved in 30 mL of THF and then 2.0 M BH$_3$.Me$_2$S solution in THF (5.7 mL, 11.38 mmol) was added. This reaction mixture heated at 50° C. for 2 h. After cooling to room temperature, the mixture was quenched slowly with 6 mL of methanol. After the bubbling subsided, 20 mL of MeOH was added and the mixture was concentrated. The resulting oil was filtered through a plug of silica gel using 9:1 hexane-EtOAe. The filtrate was concentrated and purified by column chromatography (10-25% EtOAc-hexane) to give compound 40 as a thick clear oil. ES-MS: Calcd. for C$_{18}$H$_{26}$N$_2$O$_2$: 302.41. Found: 303 (M+1).

|  | R | * | Parent ion (M + H) |
|---|---|---|---|
| 41a | i-Pr | R | 229 |
| 41b | i-Pr | S | 229 |
| 41c | i-Bu | S | 243 |
| 41d | Et | S | 215 |
| 41e | Me | S | 201 |
| 41f | di-Me |  | 215 |
| 41g | cyclopropyl |  | 157 (M – tBu) |

Intermediate 42:

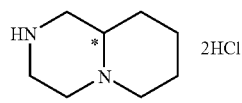

42

Compound 37 (0.71 g, 3.08 mmol) was dissolved in 15.4 mL of MeOH and 10% Pd/C (0.14 g) and 3 M HCl (2.5 mL, 7.39 mmol) added, and then stirred at room temperature under H$_2$ overnight. This mixture was filtered through Celite using MeOH and concentrated to give compound 42 as a white solid. ES-MS: Calcd. for C$_8$H$_{16}$N$_2$: 140.13. Found 141 (M+1); 5 h, ES-MS: Calcd. for C$_8$H$_{16}$N$_2$: 140.13. Found 141 (M+1).

Intermediates 42 a-b were prepared in a manner similar to intermediate 42.

|  | * | Parent ion (M + H) |
|---|---|---|
| 42a | R | 141 |
| 42b | S | 141 |

Preparation of Piperazine Intermediates:

Scheme 1

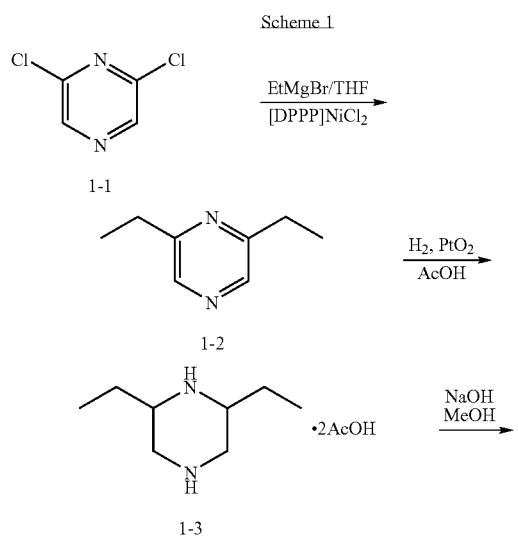

Scheme 2

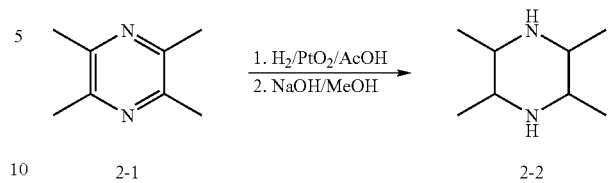

To a solution of 2-1 (5 g, 36.7 mmol) in acetic acid (75 mL) was added PtO$_2$ (450 mg). After stirring the reaction mixture under H$_2$ atmosphere overnight, the mixture was flushed with nitrogen, filtered and concentrated. To a solution of the bis-acetate salt (9.63 g, 36.7 mmol) in methanol (20 mL) was added 5N NaOH (40 mL, 200 mmol). Methanol was removed under vacuum, and the mixture was extracted with CH$_2$Cl$_2$. The organic layer was dried and concentrated to give 2-2 (4.26 g).

Scheme 3

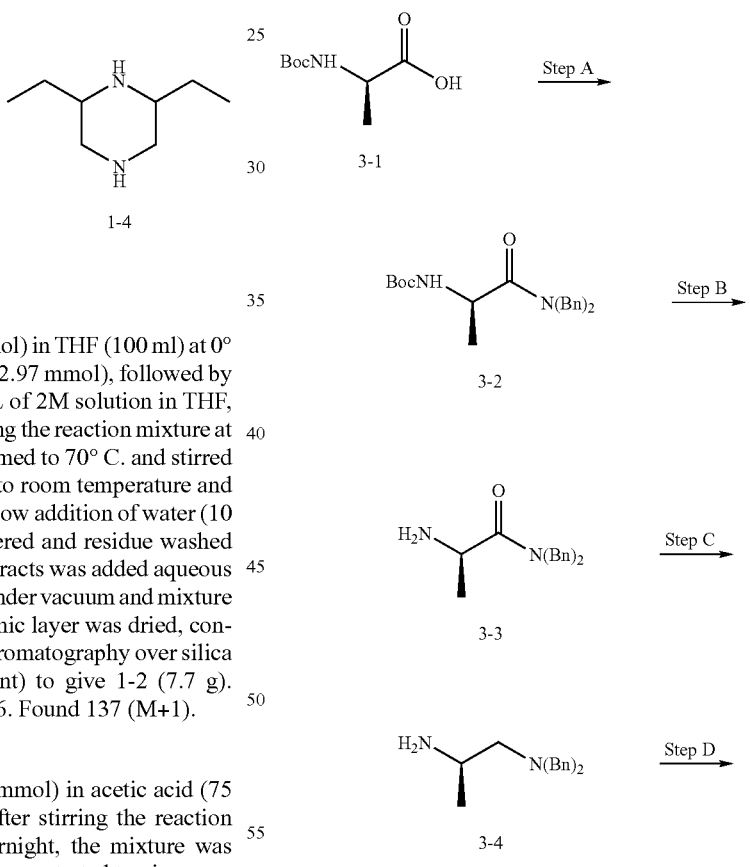

Step A:

To a solution 1-1 (8.85 g, 59.4 mmol) in THF (100 ml) at 0° C. was added [DPPP]NiCl$_2$ (1.61 g, 2.97 mmol), followed by slow addition of EtMgBr (65.34 mL of 2M solution in THF, 130.68 mmol) in 20 min. After stirring the reaction mixture at 0° C. for 0.5 h, the mixture was warmed to 70° C. and stirred overnight. The mixture was cooled to room temperature and excess of EtMgBr decomposed by slow addition of water (10 mL). The reaction mixture was filtered and residue washed with THF. To the combined THF extracts was added aqueous NaHCO$_3$ (100 mL), THF removed under vacuum and mixture extracted with ethyl ether. The organic layer was dried, concentrated and purified by column chromatography over silica gel (7% EtOAc in hexane as eluent) to give 1-2 (7.7 g). ES-MS calculated for C$_8$H$_{12}$N$_2$: 136. Found 137 (M+1).

Step B:

To a solution of 1-2 (7.7 g, 56.6 mmol) in acetic acid (75 mL) was added PtO$_2$ (600 mg). After stirring the reaction mixture under H$_2$ atmosphere overnight, the mixture was flushed with nitrogen, filtered and concentrated to give 1-3. ES-MS calculated for C$_8$H$_{18}$N$_2$: 142. Found 143 CM+1).

Step C:

To a solution of 1-2 (4.43 g, 17.3 mmol) in methanol (75 mL) was added 5N NaOH (10 mL, 50 mmol). Methanol was removed under vacuum, and the mixture was extracted with CH$_2$Cl$_2$. The organic layer was dried and concentrated to give 1-3 (2.15 g).

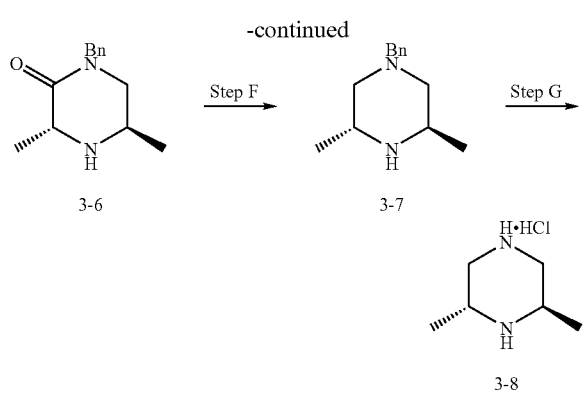

3-6          3-7

3-8

Step A:

To a solution of N-t-Boc-D-alanine (3-1) (10 g, 52.9 mmol) in methylene chloride (200 mL) was added N-methylmorpholine (8.7 mL, 79.2 mmol), 1-hydroxybenzotriazole hydrate (7.8 g, 58.2 mmol), EDC (15.2 g, 79.2 mmol) and dibenzylamine (11.2 mL, 58.2 mmol). The reaction mixture was stirred at room temperature for 18 h. The reaction mixture was concentrated under diminished pressure, and the residue was partitioned between water and ethyl acetate. The aqueous phase was extracted with ethyl acetate, and the combined organic extracts were washed with water and brine, dried over $MgSO_4$, filtered and concentrated to provide a white solid which was washed with hexane to remove residual dibenzylamine to give 3-2 as a white solid (16.0 g). ES-MS calc. for $C_{22}H_{28}N_2O_3$: 368.2. Found: 369 (M+1), 391 (M+Na).

Step B:

To a solution of 3-2 (7.6 g, 20.7 mmol) in methylene chloride (30 mL) was added TFA (30 mL) at 0° for 1 h. The reaction mixture was allowed to warm up to room temperature and stirred for 18 h. The reaction mixture was concentrated, and the residue was partitioned between methylene chloride and saturated aqueous sodium bicarbonate. The aqueous layer was extracted with methylene chloride, and the combined extracts were washed with water and brine, dried over $MgSO_4$ and solvent was removed in vacuo to provide 3-3 as an oil (4.9 g). ES-MS calc. for $C_{17}H_{20}N_2O$: 268. Found: 269 (M+H), 291 (M+Na).

Step C:

To a solution of 3-3 (4.89 g, 18.2 mmol) in THF (100 mL) was added $BH_3.THF$ (1.0 M, 128 mmol, 128 mL) slowly. The reaction mixture was stirred at room temperature for 48 h. After cooling to 0° C., the reaction mixture was quenched by slow addition of HCl (2.0M, 60 mL). The mixture was made basic with NaOH (5N, 20 mL), and KOH (38 g, 678.6 mmol) was added, and the mixture was heated at reflux for 24 h. The reaction mixture was cooled to room temperature, the two layers separated, and the aqueous layer extracted with ethyl acetate. The combined organic layers were washed with brine, dried over $MgSO_4$ and concentrated to provide 3-4 as a white semisolid (4.95 g). ES-MS calc. for $C_{17}H_{22}N_2$: 254. Found: 255 (M+H).

Step D:

To a solution of methyl (S)-lactate (1.7 mL, 17.9 mmol) in methylene chloride (85 mL) was added trifluoromethanesulfonic anhydride at 0° C. After stirring for 10 min, a solution of 2,6-lutidine (2.57 mL, 22.05 mmol) in methylene chloride (8.5 mL) was added. After an additional 10 min of stirring at 0° C., a solution of intermediate 3-4 (3.5 g, 13.8 mmol) in methylene chloride (4 mL) containing triethylamine (3.1 mL, 22.1 mmol) was added. The reaction mixture was stirred 2 h at 0° C. and 3 h at room temperature at which time the mixture was partitioned between $CH_2Cl_2$ and saturated aqueous $NaHCO_3$. The aqueous layer was extracted further with $CH_2Cl_2$, and the combined organic extracts were washed with water, brine, and dried over $MgSO_4$. The mixture was filtered and concentrated under reduced pressure to provide a brown oil which was purified by column chromatography to give 3-5 as a colorless oil (2.6 g). ES-MS calc. for $C_{21}H_{28}N_2O_2$: 340.2. Found: 341 (M+H).

Step E:

To a solution of 3-5 (2.5 g, 7.35 mmol) in ethanol (80 mL) was added $Pd(OH)_2$ (20% wt on carbon, 0.375 g) and HCl (4.0 M in dioxane, 3.68 mL, 14.7 mmol). The reaction mixture was evacuated and purged with nitrogen 3 times, and then hydrogenated under a balloon atmosphere of hydrogen gas for 18 h. The mixture was filtered through celite, and the solid was washed with MeOH and $CH_2Cl_2$. The combined filtrate and washings were concentrated. The residue was dissolved in ethanol (80 mL), p-toluenesulfonic acid (0.42 g, 2.21 mmol) was added and the mixture heated at reflux for 18 h. The reaction mixture was concentrated and partitioned between $CH_2Cl_2$ and saturated aqueous $NaHCO_3$. The aqueous layer was further extracted with $CH_2Cl_2$, and the combined organic extracts were dried ($MgSO_4$), filtered and concentrated to give 3-6 as a yellow oil (1.1 g).

ES-MS calc. for $C_{13}H_{18}N_2O$: 218.1. Found: 219 (M+H).

Step F:

To a solution of 3-6 (1.1 g, 5.1 mmol) in THF (40 mL) was added $BH_3.THF$ (1.0 M, 15.2 mL, 15.2 mmol) slowly. The reaction mixture was stirred at room temperature for 0.5 h, then heated at 65° C. for 18 h. The reaction mixture was cooled to room temperature and quenched with methanol (6.1 mL, 152 mmol) slowly. After stirring 0.5 h at room temperature, HCl (4.0 M in dioxane, 4.5 mL, 18.2 mmol) was added, and reaction mixture was refluxed for 0.5 h and then concentrated. The residue was dissolved in methanol (40 mL), HCl (4.0M in dioxane, 5 mL) added, and the mixture heated at reflux temperature for 3 h and concentrated. The residue was triturated with diethyl ether to give 3-7 as a solid (1.1 g). ES-MS calc. for $C_{13}H_{20}N_2$: 204.2. Found: 205 (M+H).

Step G:

To a solution of 3-7 (1.18 g, 5.78 mmol) in methanol (40 mL) was added $Pd(OH)_2$ (20% wt on carbon, 0.24 g) and HCl (4.0 M in dioxane 2.89 mL, 11.6 mmol). The reaction mixture was evacuated and purged with nitrogen 3 times, and then hydrogenated under a balloon atmosphere of hydrogen gas for 18 h. The catalyst was removed by filtration through celite, and the filtrate was concentrated. The residue was triturated with diethyl ether to afford 3-8 as a white solid (0.85 g). ES-MS calc. for $C_6H_{14}N_2$: 114. Found: 115 (M+H).

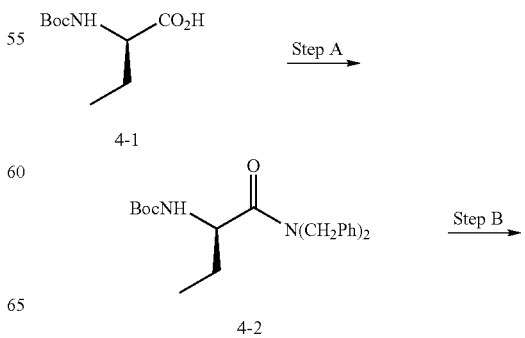

Scheme 4

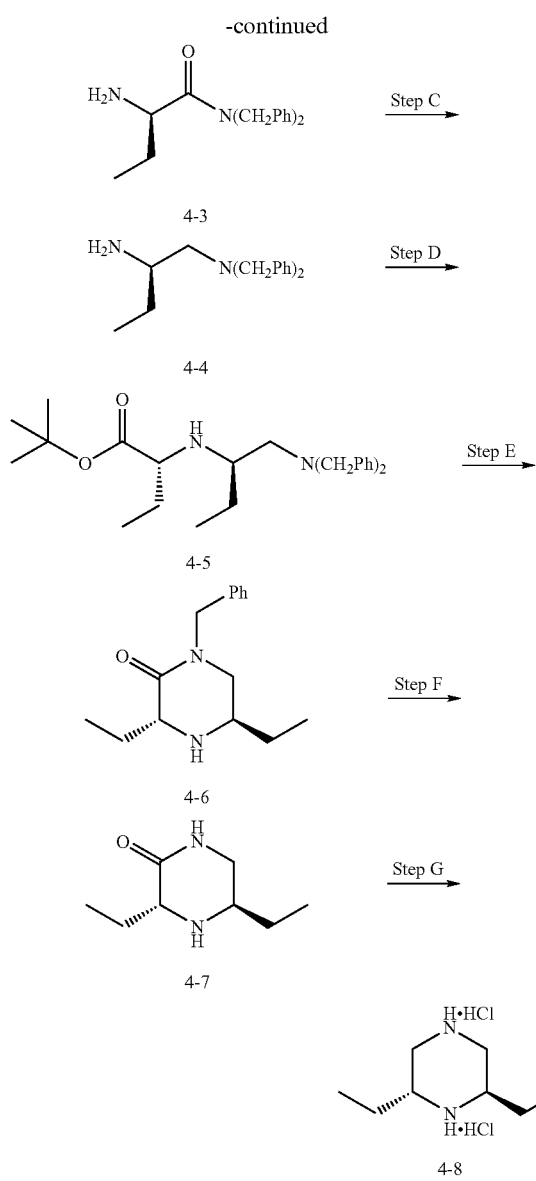

Step D:

Compound 4-5 was prepared from 4-4 and tert-butyl (S)(−)-2-hydroxybutyrate in an analogous manner to the one described for the preparation of 3-5. ES-MS calc. for $C_{26}H_{38}N_2O_2$: 410.3. Found: 411 (M+H).

Step E:

To a solution of 4-5 (1.0 g, 2.44 mmol) in ethanol (40 mL) was added Pd(OH)$_2$ (20% wt on carbon, 0.15 g) and HCl (4.0 M in dioxane, 1.22 mL, 4.88 mmol). The reaction mixture was evacuated and purged with nitrogen 3 times, and then hydrogenated under a balloon atmosphere of hydrogen gas for 18 h. The mixture was filtered through celite, and the solid was washed with MeOH and CH$_2$Cl$_2$. The combined filtrate and washings were concentrated. The residue was dissolved in toluene (40 mL), acetic acid (0.42 mL, 7.32 mmol) was added and the mixture heated at reflux temperature for 48 h. The reaction mixture was concentrated to give 4-6 as a brown oil (0.35 g).

ES-MS calc. for $C_{15}H_{22}N_2O$: 246.2. Found: 247 (M+H).

Step F:

Compound 4-7 was prepared from 4-6 in an analogous manner to the one described for the preparation of 3-7.

ES-MS calc. for $C_8H_{16}N_2O$: 156. Found: 157 (M+H).

Step G:

Compound 4-8 was prepared from 4-7 in an analogous manner to the one described for the preparation of 3-8.

ES-MS calc. for $C_8H_{18}N_2$: 142.2. Found: 143 (M+H).

Scheme 5

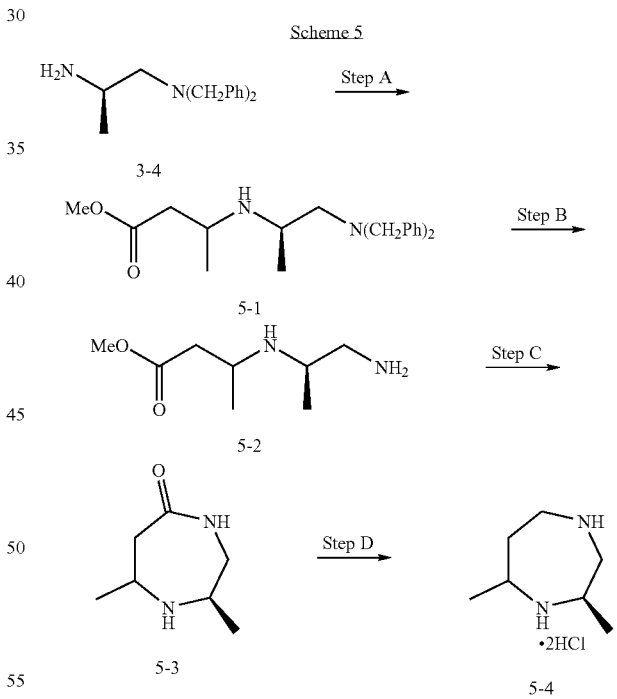

Step A:

Compound 4-2 was prepared from Boc-D-2-aminobutyric acid in an analogous manner to the one described for the preparation of compound 3-2.

ES-MS calc. for $C_{23}H_{30}N_2O_3$: 382.2. Found: 383 (M+H), 405 (M+Na).

Step B:

Compound 4-3 was prepared from 4-2 in an analogous manner to the one described for the preparation of compound 3-3.

ES-MS calc. for $C_{18}H_{22}N_2O$: 282.2. Found: 283 (M+H).

Step C:

Compound 4-4 was prepared from 4-3 in an analogous manner to the one described for the preparation of compound 3-4.

ES-MS calc. for $C_{18}H_{24}N_2$: 268.2. Found: 269 (M+H).

Step A:

To a solution of 3-4 (1.0 g, 3.94 mmol) in toluene (15 mL) was added methyl acetoacetate (0.47 mL, 4.33 mmol) and acetic acid (0.45 mL, 7.88 mmol). After stirring at 65° C. for 0.5 h, the reaction mixture was concentrated. The residue was dissolved in toluene (15 mL), stirred at 65° C. for another 0.5 h, and concentrated. The residue was dissolved in THF (15 mL), acetic acid (0.45 mL, 7.88 mmol) was added followed by sodium triacetoxyborohydride (2.5 g, 11.82 mmol) at 0° C., and then allowed to warm up to room temperature and stirred for 18 h. The reaction mixture was concentrated, and the residue was partitioned between CH$_2$Cl$_2$ and saturated aqueous Na$_2$CO$_3$. The aqueous layer was extracted with CH$_2$Cl$_2$, and the combined organic layers were washed with brine, dried over MgSO$_4$, and concentrated to give an oil, which was purified by flash silica gel chromatography (1:1 hexane/ethyl acetate) to give 5-1 as a white semisolid (0.65 g).

ES-MS calc. for C$_{22}$H$_{30}$N$_2$O$_2$: 354.2. Found: 355(M+H).

Step B:

To a solution of 5-1 (0.65 g, 1.84 mmol) in ethanol (80 mL) was added Pd(OH)$_2$ (20% wt on carbon, 0.98 g) and HCl (4.0 M in dioxane, 0.92 mL, 3.67 mmol). The reaction mixture was evacuated and purged with nitrogen 3 times, and then hydrogenated under a balloon atmosphere of hydrogen gas for 18 h. The mixture was filtered through celite, and the solid was washed with MeOH and CH$_2$Cl$_2$. The combined filtrates were concentrated to give 5-2 as a brown oil (0.31 g).

ES-MS calc. for C$_8$H$_{18}$N$_2$O$_2$: 174.2. Found: 175 (M+H).

Step C:

A sealed bottle was charged with a solution of 5-2 (0.17 g, 0.95 mmol) in methanol (15 mL), and sodium methoxide (25% wt in methanol, 0.98 mL, 4.29 mmol) was added. The bottle was sealed and heated at 85° C. for 2 h. The reaction mixture was cooled to room temperature, quenched with NaHCO$_3$ (0.36 g, 4.29 mmol), and concentrated. The resulting solid was dissolved in EtOAc-CH$_3$OH (15:1), then filtered through celite to remove the inorganic salts. The filtrate was concentrated to give 5-3 as a yellow oil (0.13 g).

ES-MS calc. for C$_7$H$_{14}$N$_2$O: 142.2. Found: 143 (M+H).

Step D:

Compound 5-4 was prepared from 5-3 in an analogous manner to the one described for the preparation of 3-7. ES-MS calc. for C$_7$H$_{16}$N$_2$: 128.1. Found: 129 (M+H).

Step A:

Compound 6-1 was prepared from intermediate 3-4 and ethyl propionylacetate in an analogous manner to the one described for the preparation of 5-1. ES-MS calc. for C$_{24}$H$_{34}$N$_2$O$_2$: 382.3. Found: 383 (M+H).

Step B:

Compound 6-2 was prepared from 6-1 in an analogous manner to the one described for the preparation of compound 5-2.

ES-MS calc. for C$_{10}$H$_{22}$N$_2$O$_2$: 202.2. Found: 203 (M+H).

Step C:

Compound 6-3 was prepared from 6-2 in an analogous manner to the one described for the preparation of compound 5-3.

ES-MS calc. for C$_8$H$_{16}$N$_2$O: 156.1. Found: 157 (M+H).

Step D:

Compound 6-4 was prepared from 6-3 in an analogous manner to the one described for the preparation of compound 5-4.

ES-MS calc. for C$_8$H$_{18}$N$_2$: 142.2. Found: 143 (M+H).

The following Examples are provided to illustrate the invention and are not to be construed as limiting the scope of the invention in any manner.

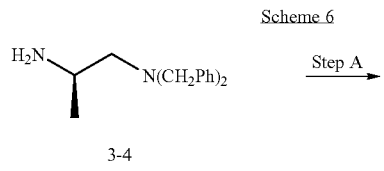

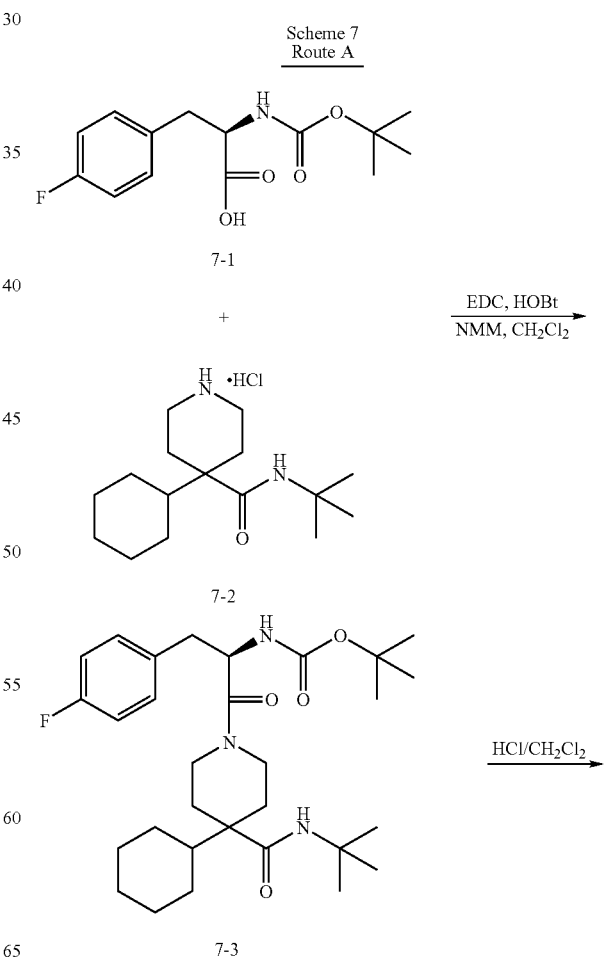

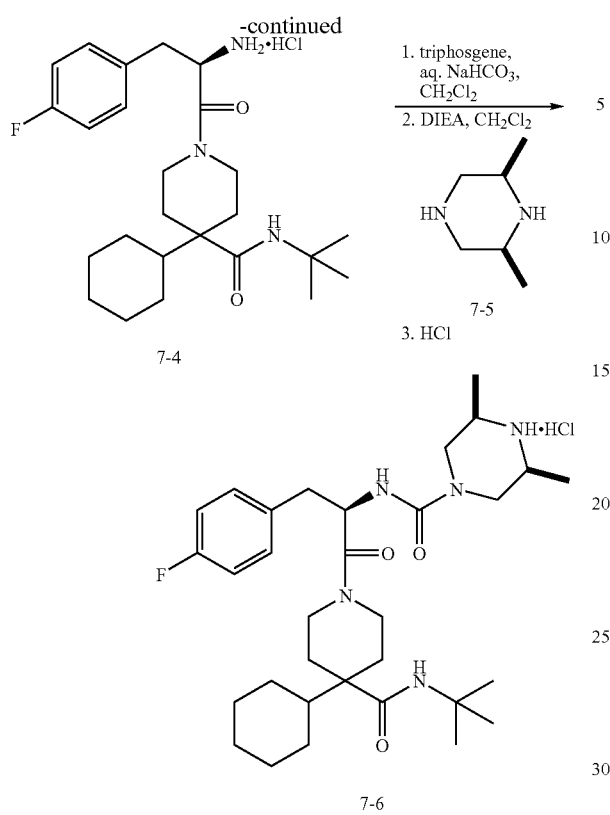

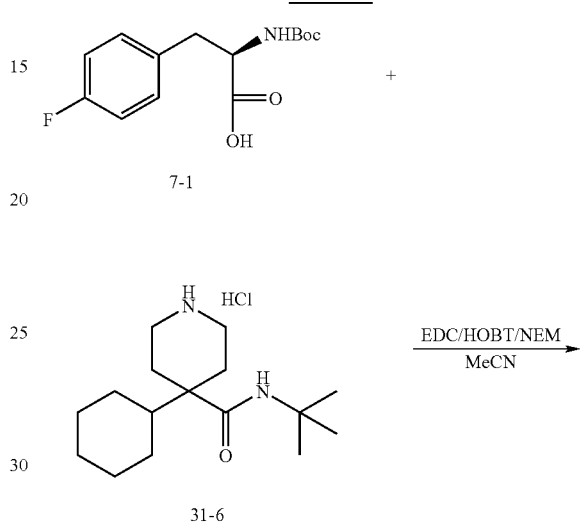

EXAMPLE 1

Route A:

Step A:

To a solution of 7-1 (3.74 g, 13.24 mmol) in CH$_2$Cl$_2$ (100 mL) at room temperature was added EDC (3.044 g, 15.88 mmol), HOBT (2.14 g, 15.88 mmol) and NMM (5.37 g, 52.96 mmol). After stirring the reaction mixture for 5 min, the piperidine intermediate 7-2 (4 g, 13.24 mmol) was added and mixture stirred overnight. The reaction mixture was diluted with CH$_2$Cl$_2$, washed with water, 0.5N HCl and saturated aqueous NaHCO$_3$. The organic layer was dried, concentrated and the residue was purified by column chromatography over silica gel using 10% EtOAc/CH$_2$Cl$_2$ as eluent to afford 7-3 (7 g).

ES-MS calculated for C$_{30}$H$_{46}$N$_3$O$_4$F: 531. Found: 532 (M+1).

Step B:

To a solution of 7-3 (7 g, 13.1 mmol) in CH$_2$Cl$_2$ (15 mL) at room temperature was added 5N HCl in isopropanol (15 mL, 75 mmol). After stirring for 2 h, the reaction mixture was concentrated to give 7-4 as the hydrochloride salt.

ES-MS calculated for C$_{25}$H$_{38}$N$_3$O$_4$F: 431. Found: 432 (M+1).

Step C:

To a solution of 7-4 (4 g, 8.56 mmol) in CH$_2$Cl$_2$ (65 mL) was added saturated aqueous NaHCO$_3$ (65 mL). After stirring the reaction mixture for 5 min, triphosgene (1.02 g, 3.43 mmol) was added. The reaction mixture was stirred for an additional 20 min. The organic layer was separated, dried, and filtered. To this solution was added DIEA (1.106 g, 8.56 mmol) and a solution of 2,6-dimethylpiperazine 7-5 (2.43 g, 21.4 mmol) in CH$_2$Cl$_2$. After stirring the reaction mixture for 1 h, the organic layer was washed with brine, dried, concentrated. The crude product was purified by reverse phase HPLC to give 4 g of the free base which was dissolved in 5% MeOH/benzene and treated with a solution of 5N HCl in isopropanol (4 mL). The mixture was cooled and lyophilized to give the hydrochloride salt 7-6.

ES-MS calculated for C$_{32}$H$_{50}$N$_5$O$_3$F: 571. Found: 572 (M+1).

Scheme 7
Route B

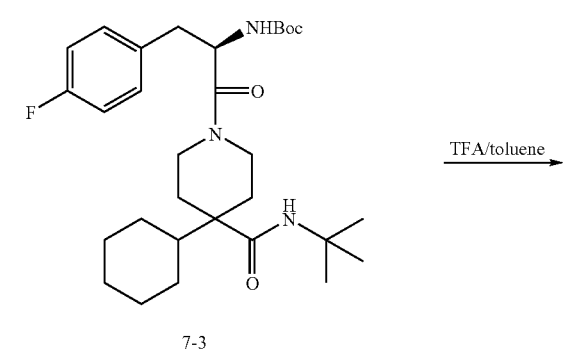

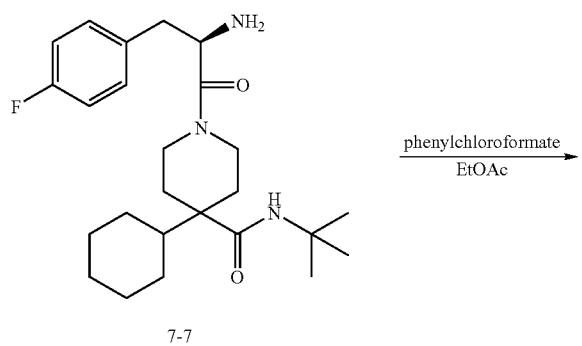

-continued

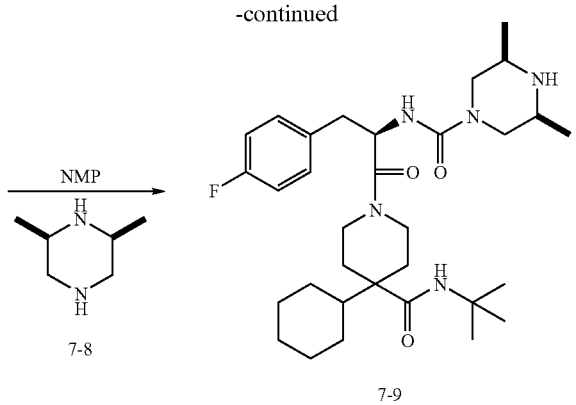

Route B:

Step A:

To acetonitrile (500 mL, 10 ml/g, all volumes relative to starting acid) was added 1-hydroxybenzotriazole (59.6 g, 440 mmol) followed by Boc-D-fluorophenylalanine 7-1 (50.0 g, 180 mmol), 1-(3-dimethylaminopropyl)-1-ethylcarbodiimide hydrochloride (41.4 g, 220 mmol) and N-ethylmorpholine (91.6 ml, 720 mmol) in that order. The resulting solution was stirred for 10 min, then piperidine-amide hydrochloride intermediate 31-6 (60.0 g, 200 mmol) was added. The reaction was aged at room temperature for 2.5 h, then quenched with water (1.0 L, 20 mL/g) and extracted into toluene (1.0 L, 20 ml/g). The phases were separated, and the toluene layer was washed twice with water (500 ml, 10 ml/g). The remaining solution was then azeotropically dried and concentrated to 500 ml via an atmospheric distillation, and the resulting toluene solution of compound 7-3 was used in Step B.

Step B:

To the toluene solution of compound 7-3, at room temperature, was charged TFA (277.3 ml, 3.6 mol). The reaction was aged at room temperature for approximately two hours to give intermediate 7-7. Upon completion of reaction the solution was concentrated under vacuum in order to remove excess TFA and solvent switched completely to ethyl acetate (2×500 ml EtOAc flushes). The resulting ethyl acetate solution (re-diluted to ~20 ml/g, 1.0 L) was then washed with saturated bicarbonate solution (2×500 ml), followed by a final water wash (500 ml). Post washes, the ethyl acetate solution was azeotropically dried under vacuum and then re-diluted to ~10 ml/g (500 ml). The ethyl acetate solution of 7-7 was used in Step C.

Step C:

Diisopropylethylamine (31.4 ml, 180 mmol) was charged at room temperature to the ethyl acetate solution of intermediate 7-7, and the resulting solution was cooled to ~5° C. via an ice bath. Phenyl chloroformate (23.9 ml, 190 mmol) was then incrementally added via an addition funnel maintaining the temperature below 20° C. The reaction was aged for 30 minutes at room temperature, and then quenched with an equal volume of water (500 ml). The EtOAc layer was then washed with saturated ammonium chloride (500 ml) and water (500 ml). The resulting EtOAc solution was solvent switched to NMP (~5 ml/g, 250 ml) and cis-2,6-dimethylpiperazine 7-8 (26.7 g, 230 mmol) was added. The reaction was aged at room temperature for ~16 hours, then the reaction was quenched with water (500 ml) and extracted into ethyl acetate (500 ml). The ethyl acetate layer was then washed with equal volumes of 1N NaOH solution (2×500 ml) and water wash (250 ml) to give a crude ethyl acetate solution of 7-9. To the crude ethyl acetate solution of 7-9 (75 g assay, 130 mmol) was added benzene sulfonic acid (27 g, 171 mmol), then the mixture was seeded with 7-9 besylate monohydrate. The resulting slurry was aged 18 h, or until equilibrium was reached. The product was isolated via filtration, and the cake was washed with 150 mL of EtOAc. The material was dried in vacuo with a nitrogen purge at 60° C. to give the crude besylate monohydrate of 7-9. 10 g of the crude besylate monohydrate of 7-9 were dissolved in 3% aq THF (130 mL, 13 volumes) of at 60° C. The solution was filtered, and the pot was rinsed with THF (10 mL, 1 volume). The solution was cooled and seeded (100 mg) at 35° C. The mixture was aged 18 h, then EtOAc (140 mL, 14 volumes) was added over 2 h. The mixture was aged until equilibrium was reached at a supernatant concentration of 2.4 mg/ml (about 48 h). The product was isolated via filtration, with a 20 mL 3% aqueous THF/EtOAc wash. The material was dried in vacuo with a nitrogen purge at 60° C. to afford compound 7-9 as the besylate salt monohydrate.

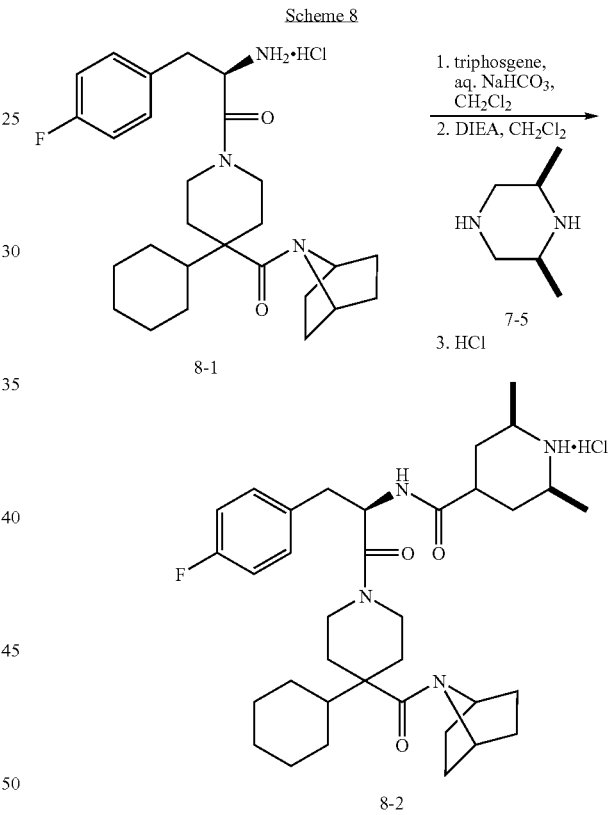

EXAMPLE 2

To a stirred solution of 8-1 (54 mg, 0.11 mmol) in methylene chloride (3 mL) and saturated aqueous sodium bicarbonate (3 mL), cooled to 0° C. was added triphosgene (13 mg, 0.044 mmol). The reaction mixture was stirred for 20 min. The organic phase was separated, dried over MgSO$_4$ and filtered. To the resulting solution was added triethylamine (13.3 mg, 0.14 mmol) followed by 2,6-dimethylpiperazine (7-5) (15.7 mg, 0.14 mmol). The reaction mixture was stirred for 1 h. It was then concentrated, taken up in the minimal volume of methanol and subjected to preparative HPLC (C18, 30% acetonitrile/water-80% acetonitrile/water) to provide the desired product as the free base which was dissolved in 5% MeOH/benzene and treated with a solution of 5N HCl in isopropanol. The mixture was cooled and lyophilized to give the hydrochloride salt 8-2.

ES-MS calc. for $C_{34}H_{50}FN_5O_3$: 595. Found: 596 (M+H).

Following procedures similar to that described above for Examples 1 and 2, the following compounds of structural formula III were prepared as their hydrochloride salts:

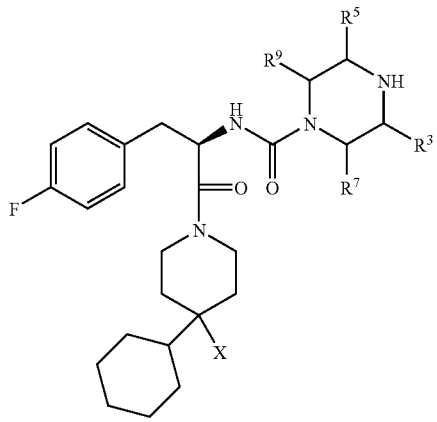

(III)

| Ex. # | $R^3$ | $R^5$ | $R^7$ | $R^9$ | X | Parent Ion m/z (M + H) |
|---|---|---|---|---|---|---|
| 3 | Me | Me | H | H | | 584 |
| 4 | Me | Me | H | H | | 598 |
| 5 | Me | Me | H | H | | 587 |
| 6 | Me | Me | H | H | | 596 |
| 7 | Me | Me | H | H | | 572 |
| 8 | Et | Et | H | H | | 600 |
| 9 | Et | Et | H | H | | 587 |
| 10 | Et | Et | H | H | | 585 |
| 11 | Me | Me | H | H | | 559 |
| 12 | Et | Et | H | H | | 587 |
| 13 | Me | Me | H | H | | 561 |
| 14 | Et | Et | H | H | | 589 |
| 15 | Et | Et | H | H | | 629 |

(III)

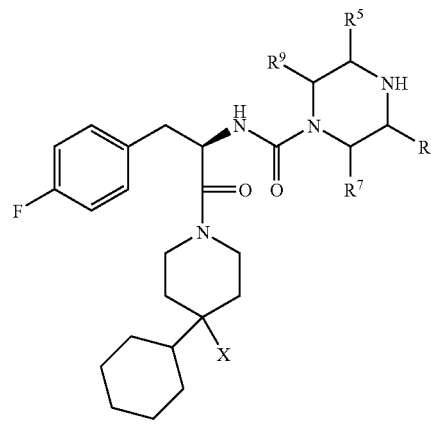

| Ex. # | R³ | R⁵ | R⁷ | R⁹ | X | Parent Ion m/z (M + H) |
|---|---|---|---|---|---|---|
| 16 | Me | Me | Me | Me | 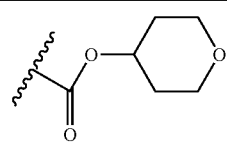 | 601 |
| 17 | Et | Et | H | H | 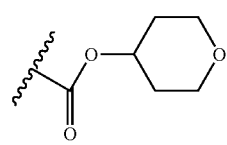 | 601 |
| 18 | Me | Me | Me | Me | 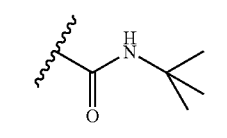 | 600 |
| 19 | Et | Et | H | H | 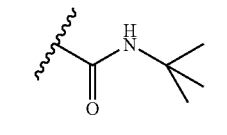 | 600 |
| 20 | Me | Me | H | H | 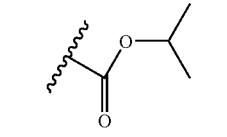 | 559 |
| 21 | Et | Et | H | H | 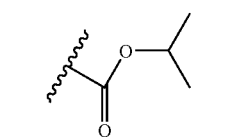 | 587 |
| 22 | H | H | H | H | 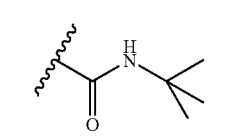 | 544 |

(III)

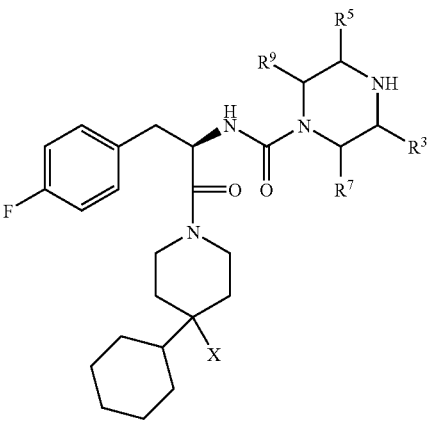

| Ex. # | R³ | R⁵ | R⁷ | R⁹ | X | Parent Ion m/z (M + H) |
|---|---|---|---|---|---|---|
| 23 | Me | Me | H | H | 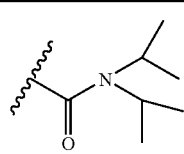 | 600 |
| 24 | Me | Me | H | H | 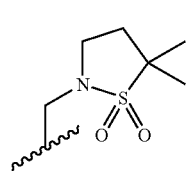 | 635 |
| 25 | Me | Me | H | H | 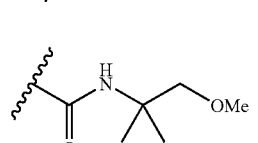 | 602 |
| 26 | Et | Et | H | H | 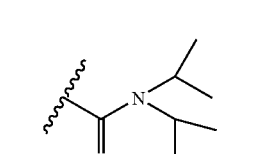 | 628 |
| 27 | Et | Et | H | H | 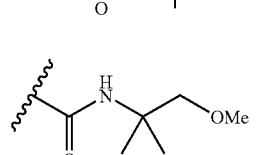 | 630 |
| 28 | Me | Me | Me | Me | 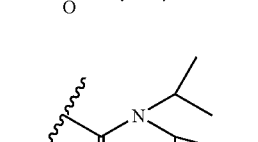 | 628 |

The following compounds of structural formula IV, as their hydrochloride salts, were also prepared in a similar manner as Examples 1 and 2, employing the appropriate piperidine and piperazine intermediates:

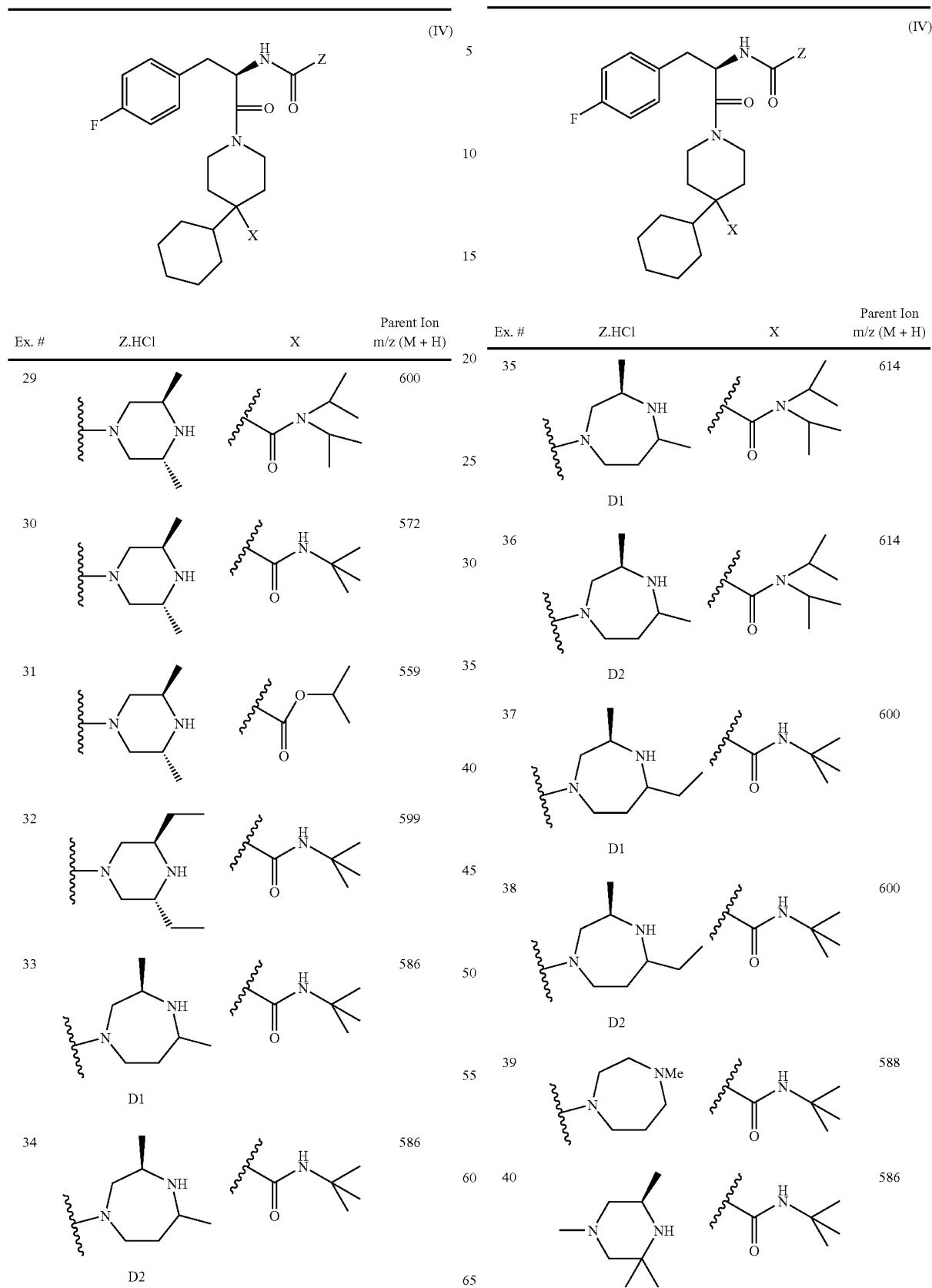

-continued (IV)

| Ex. # | Z·HCl | X | Parent Ion m/z (M + H) |
|---|---|---|---|
| 41 | piperazine, 3,3-dimethyl, (R)-methyl | –C(O)NH-tBu | 586 |
| 42 | piperazine, (S)-isopropyl | –C(O)NH-tBu | 586 |
| 43 | piperazine, (S)-isopropyl | –C(O)OEt | 559 |
| 44 | piperazine, isopropyl | –C(O)NH-tBu | 586 |
| 45 | piperazine, isopropyl | –C(O)OEt | 559 |
| 46 | piperazine, ethyl | –C(O)NH-tBu | 572 |
| 47 | piperazine, isobutyl | –C(O)NH-tBu | 600 |
| 48 | piperazine, (R)-methyl | –C(O)NH-tBu | 558 |
| 49 | piperazine, 2,2-dimethyl | –C(O)NH-tBu | 572 |
| 50 | piperazine, (R)-isopropyl | –C(O)NH-tBu | 586 |
| 51 | piperazine, (R)-isopropyl | –C(O)OEt | 559 |
| 52 | piperazine, (S)-isopropyl | –C(O)NH-tBu | 586 |
| 53 | piperazine, (S)-isopropyl | –C(O)OEt | 559 |

-continued (IV)

| Ex. # | Z.HCl | X | Parent Ion m/z (M + H) |
|---|---|---|---|
| 54 | N-piperazine with isopropyl and NMe | tert-butyl amide | 600 |
| 55 | N-piperazine with ethyl, NH | tert-butyl amide | 572 |
| 56 | N-piperazine with isobutyl, NH | tert-butyl amide | 600 |
| 57 | N-piperazine with methyl, NH | tert-butyl amide | 558 |
| 58 | N-piperazine with gem-dimethyl, NH | tert-butyl amide | 572 |
| 59 | N-piperazine with spirocyclopropyl, NH | tert-butyl amide | 570 |

The following compounds of structural formula V, as their hydrochloride salts, were also prepared in a similar manner as Examples 1 and 2, employing the appropriate piperidine and piperazine intermediates:

(V)

| Ex. # | Z.HCl | Y | X | R[11] | Parent Ion m/z (M + H) |
|---|---|---|---|---|---|
| 60 | N-methyl-2,6-dimethylpiperazine | isopropyl | tetrahydropyranyl ester | F | 589 |

-continued (V)

| Ex. # | Z.HCl | Y | X | R[11] | Parent Ion m/z (M + H) |
|---|---|---|---|---|---|
| 61 | N-methyl-2,6-dimethylpiperazine | phenyl | -C(O)N(iPr)₂ | F | 594 |
| 62 | N-methyl-2,6-dimethylpiperazine | cyclohexyl | -C(O)NH-tBu | Cl | 588 |
| 63 | N-methyl-2,6-dimethylpiperazine | cyclohexyl | -C(O)O-iPr | Cl | 575 |
| 64 | (2R,6S)-2,6-dimethylpiperazine | 3-pentyl | -C(O)O-iPr | F | 547 |
| 65 | N-methyl-2,6-diethylpiperazine | 3-pentyl | -C(O)O-iPr | F | 575 |
| 66 | N,N'-dimethylpiperazine | cyclohexyl | -C(O)NH-tBu | F | 558 |
| 67 | octahydropyrrolo[1,2-a]pyrazine | cyclohexyl | -C(O)NH-tBu | F | 584 |

-continued (V)

| Ex. # | Z·HCl | Y | X | $R^{11}$ | Parent Ion m/z (M + H) |
|---|---|---|---|---|---|
| 68 | 2,5-diazabicyclo with methyl | cyclohexyl | C(O)NH-tBu | F | 570 |
| 69 | N-Me-2,5-diazabicyclo, NH | cyclohexyl | C(O)NH-tBu | F | 556 |
| 70 | 2,5-diazabicyclo, NMe | cyclohexyl | C(O)NH-tBu | F | 570 |
| 71 | N-Me-2,5-diazabicyclo, NH | cyclohexyl | C(O)NH-tBu | Cl | 572 |
| 72 | 2,5-diazabicyclo, NMe | cyclohexyl | C(O)NH-tBu | Cl | 586 |
| 73 | N-Me-2,5-diazabicyclo, NH | cyclohexyl | C(O)OEt | F | 529 |
| 74 | N-Me-2,5-diazabicyclo, NH | cyclohexyl | C(O)OEt | Cl | 545 |

EXAMPLE 75

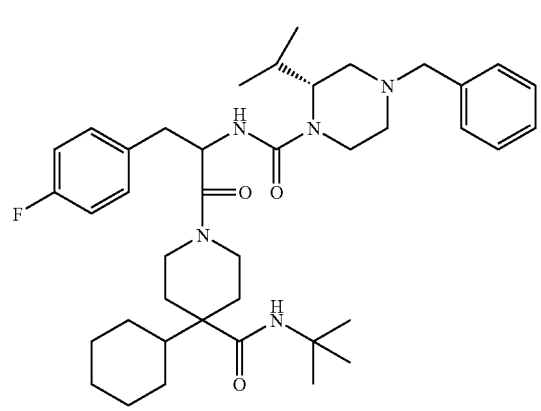

To a solution of fluoro (D)-Phe, t-butyl amide dipeptide intermediate 7-4 (0.30 g, 0.69 mmol) in 3.5 mL of $CH_2Cl_2$ was added DIEA (0.49 mL, 2.82 mmol) and then the flask was cooled to at 0° C. 4-Nitrophenyl chlorofomate (0.14 g, 0.69 mmol) was added and the yellow mixture was stirred at 0° C. for 0.5 h. Compound 3 (0.15 g, 0.69 mmol) was added and stirred at 0° C. for another 0.5 h, warmed to room temperature and stirred for 2 h. The mixture was diluted with $CH_2Cl_2$, washed with water, 1N NaOH, and brine, dried over $MgSO_4$, filtered and, concentrated to give a yellow oil. Purification by column chromatography (9:1 to 3:1 $CH_2Cl_2$-acetone) gave compound 5 as a white foamy-solid.

The following compounds of structural formula VI, as their hydrochloride salts, were also prepared in a similar manner as Example 75, employing the appropriate piperidine and piperazine intermediates:

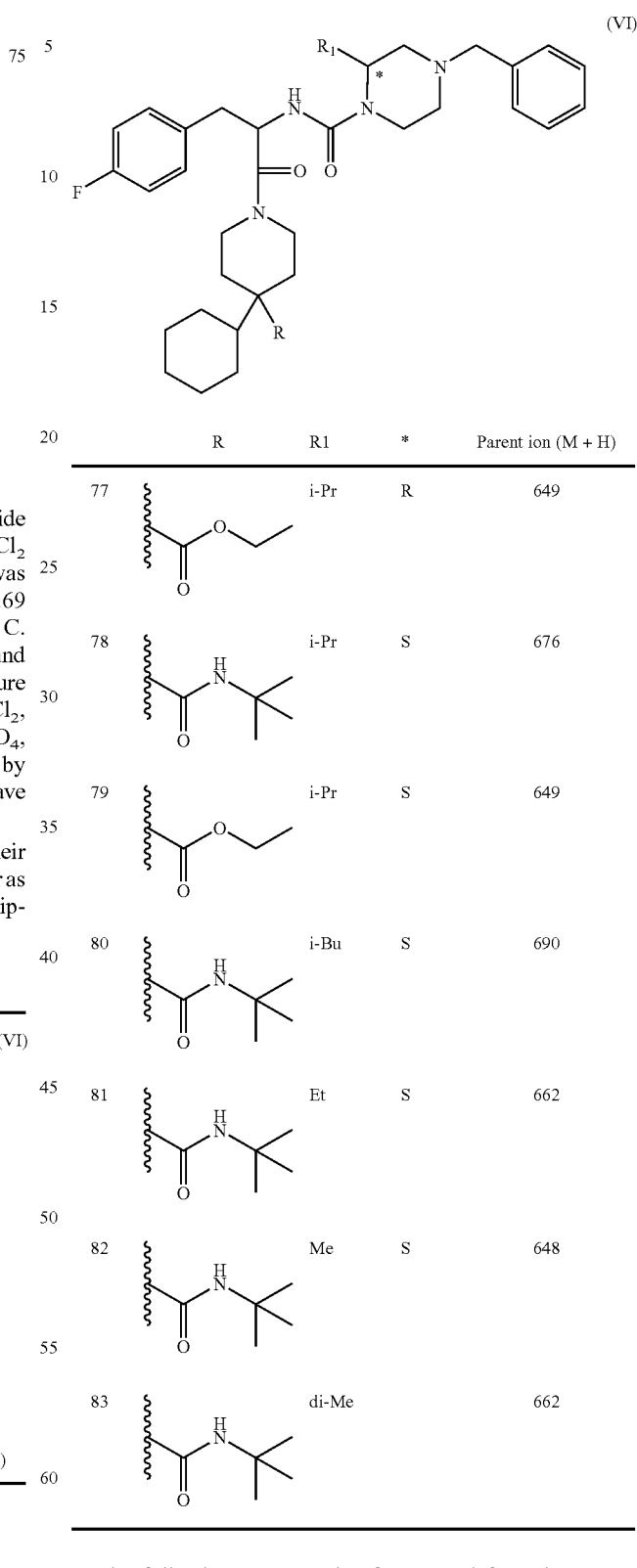

| | R | R1 | * | Parent ion (M + H) |
|---|---|---|---|---|
| 76 | ⸺C(O)NH-tBu | i-Pr | R | 676 |
| 77 | ⸺C(O)O-Et | i-Pr | R | 649 |
| 78 | ⸺C(O)NH-tBu | i-Pr | S | 676 |
| 79 | ⸺C(O)O-Et | i-Pr | S | 649 |
| 80 | ⸺C(O)NH-tBu | i-Bu | S | 690 |
| 81 | ⸺C(O)NH-tBu | Et | S | 662 |
| 82 | ⸺C(O)NH-tBu | Me | S | 648 |
| 83 | ⸺C(O)NH-tBu | di-Me | | 662 |

The following compounds of structural formula VII, as their hydrochloride salts, were also prepared in a similar manner as Example 75, employing the appropriate piperidine and piperazine intermediates:

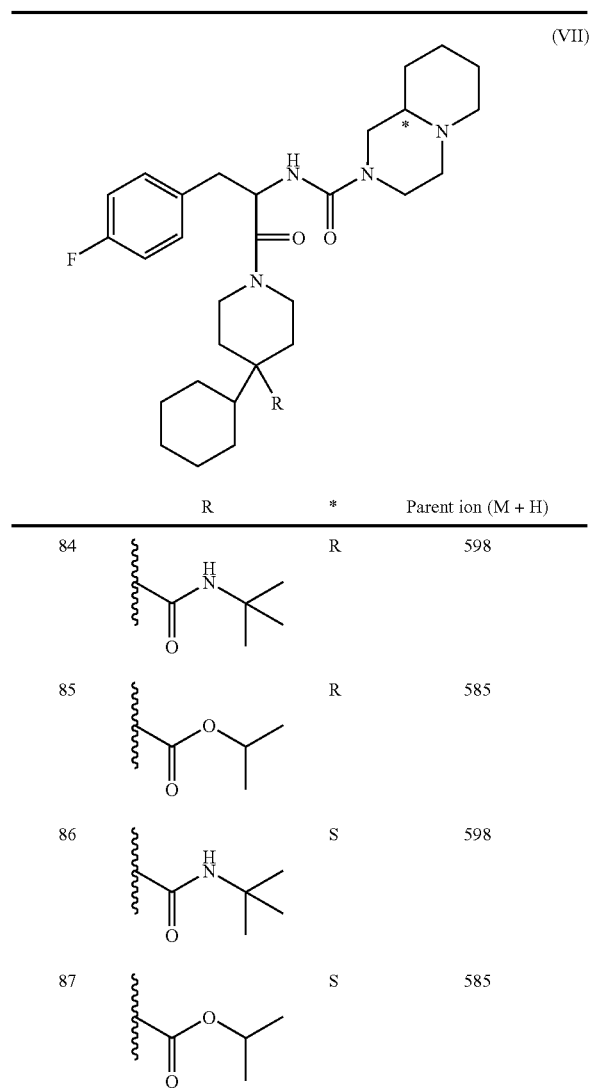

| | R | * | Parent ion (M + H) |
|---|---|---|---|
| 84 | -C(O)NH-tBu | R | 598 |
| 85 | -C(O)O-iPr | R | 585 |
| 86 | -C(O)NH-tBu | S | 598 |
| 87 | -C(O)O-iPr | S | 585 |

EXAMPLE 88

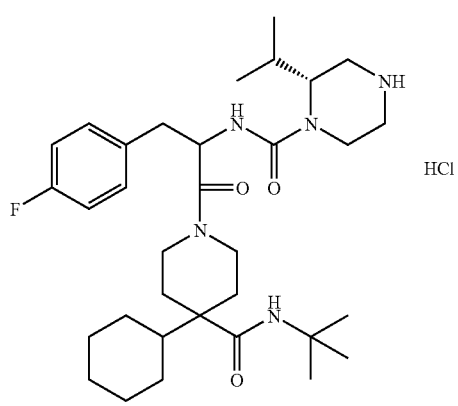

The compound of Example 75 (0.19 g, 0.28 mmol) was dissolved in 1.5 mL of MeOH and 10% Pd/C (0.02 g) and 2 M HCl solution (0.28 mL, 0.54 mmol) were added. The mixture was then stirred at room temperature under $H_2$ for 4 h. This mixture was filtered through Celite using MeOH, and concentrated to give compound 88 as a white solid.

The following compounds of structural formula VIII, as their hydrochloride salts, were also prepared in a similar manner as Example 75, employing the appropriate piperidine and piperazine intermediates:

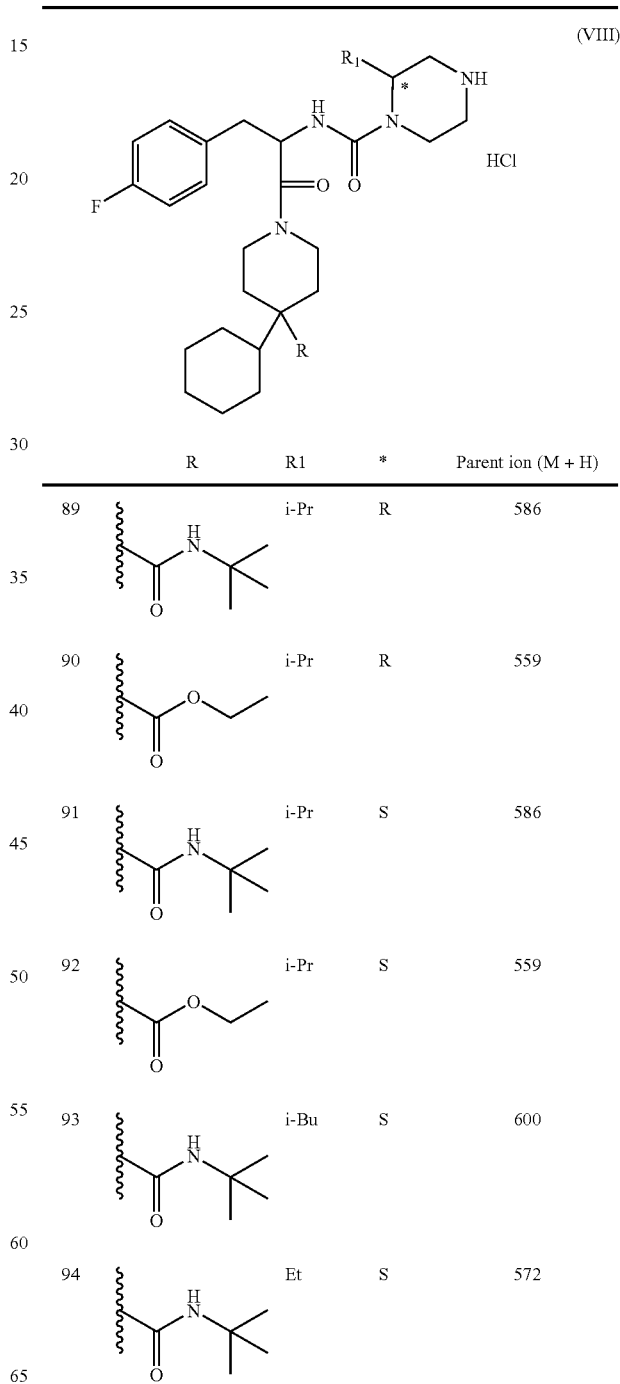

| | R | R1 | * | Parent ion (M + H) |
|---|---|---|---|---|
| 89 | -C(O)NH-tBu | i-Pr | R | 586 |
| 90 | -C(O)O-Et | i-Pr | R | 559 |
| 91 | -C(O)NH-tBu | i-Pr | S | 586 |
| 92 | -C(O)O-Et | i-Pr | S | 559 |
| 93 | -C(O)NH-tBu | i-Bu | S | 600 |
| 94 | -C(O)NH-tBu | Et | S | 572 |

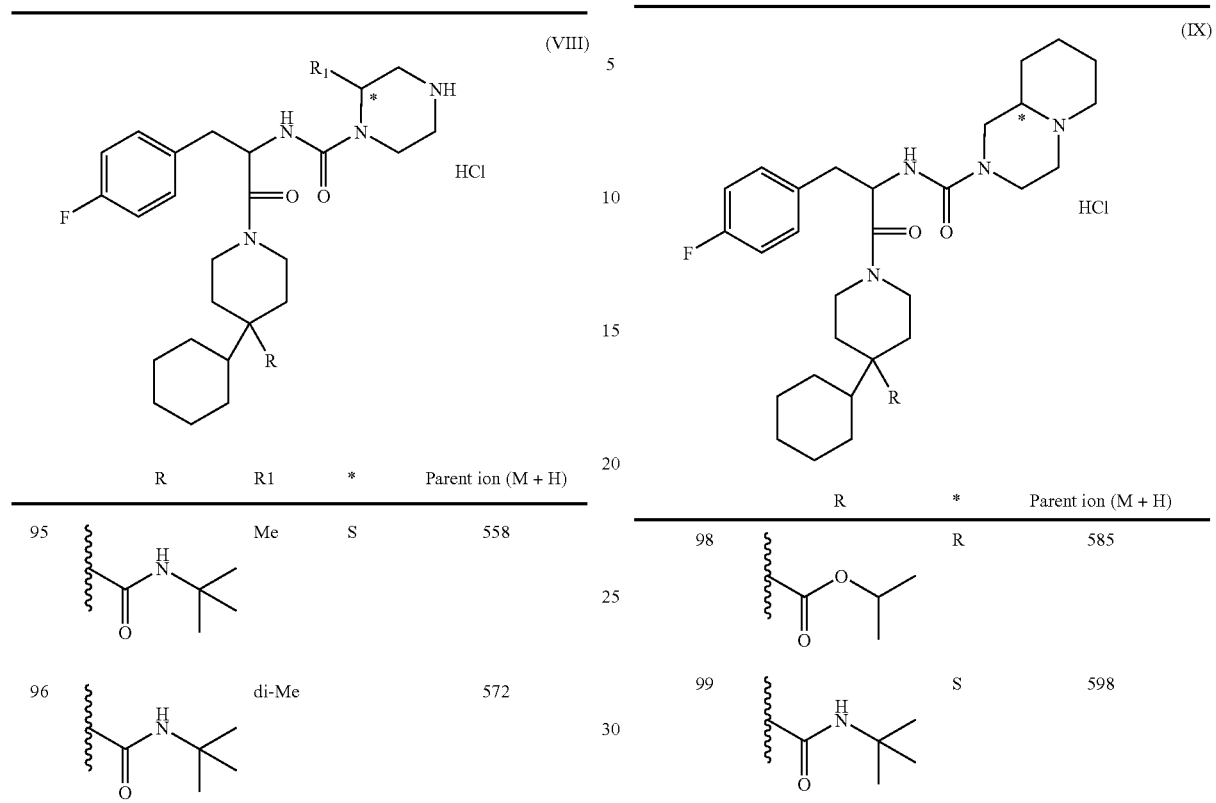

| | R | R1 | * | Parent ion (M + H) |
|---|---|---|---|---|
| 95 | —C(O)NH-tBu | Me | S | 558 |
| 96 | —C(O)NH-tBu | di-Me | | 572 |

The following compounds of structural formula IX, as their hydrochloride salts, were also prepared in a similar manner as Example 75, employing the appropriate piperidine and piperazine intermediates:

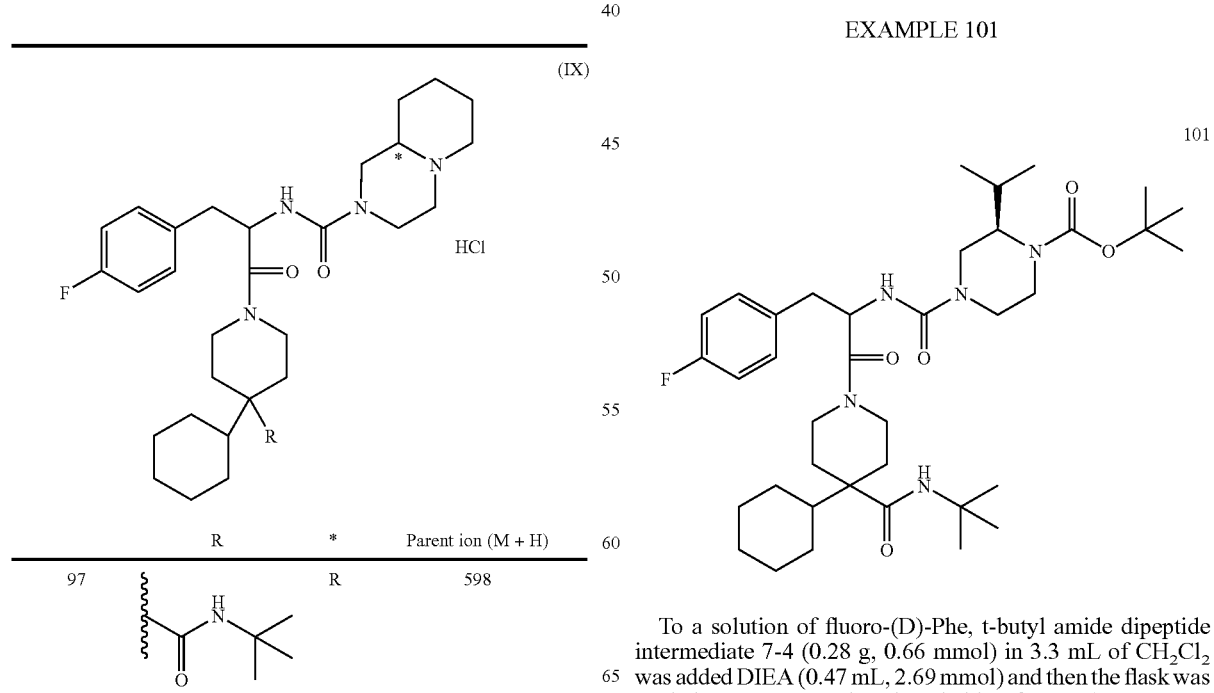

| | R | * | Parent ion (M + H) |
|---|---|---|---|
| 97 | —C(O)NH-tBu | R | 598 |
| 98 | —C(O)O-iPr | R | 585 |
| 99 | —C(O)NH-tBu | S | 598 |
| 100 | —C(O)O-iPr | S | 585 |

EXAMPLE 101

To a solution of fluoro-(D)-Phe, t-butyl amide dipeptide intermediate 7-4 (0.28 g, 0.66 mmol) in 3.3 mL of $CH_2Cl_2$ was added DIEA (0.47 mL, 2.69 mmol) and then the flask was cooled to at 0° C. 4-Nitrophenyl chlorofomate (0.13 g, 0.66 mmol) was added and the yellow mixture was stirred at 0° C.

for 0.5 h. Compound 5 (0.15 g, 0.66 mmol) was then added and stirred at 0° C. for another 0.5 h, warmed to room temperature and stirred for 2 h. The mixture was diluted with CH$_2$Cl$_2$, washed with water, 1 N NaOH (5 mL) and brine (5 mL), dried over MgSO$_4$, filtered, and concentrated to give a yellow oil. Purification by column chromatography (9:1 to 3:1 CH$_2$Cl$_2$-acetone) gave compound 101 as a white foamy-solid.

The following compounds of structural formula X, as their hydrochloride salts, were also prepared in a similar manner as Example 101, employing the appropriate piperidine and piperazine intermediates:

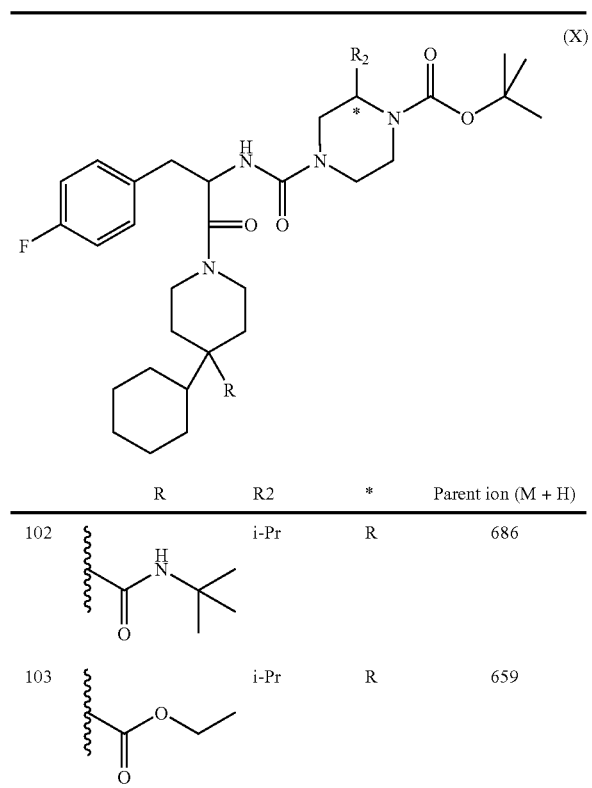

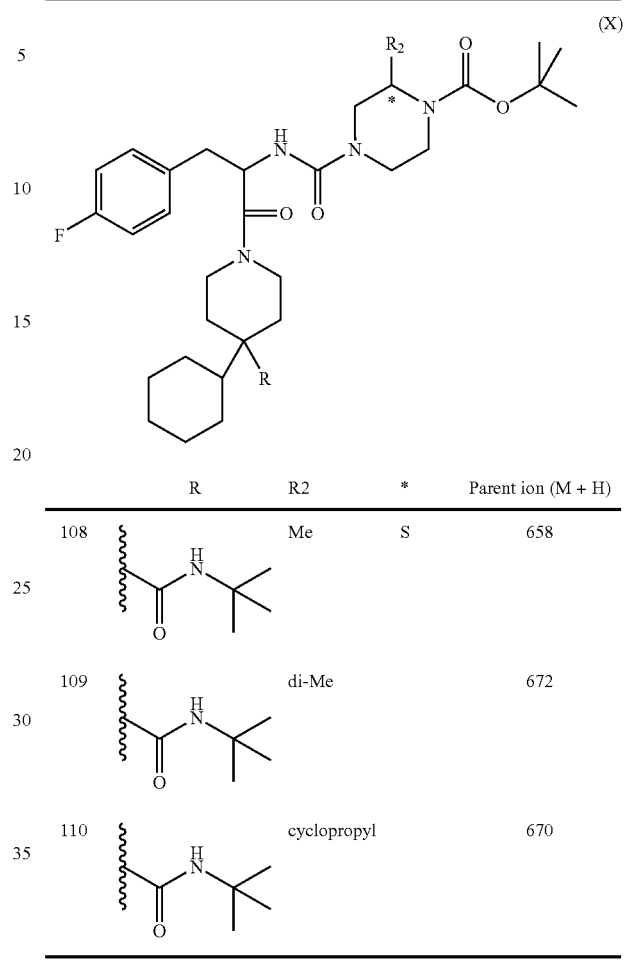

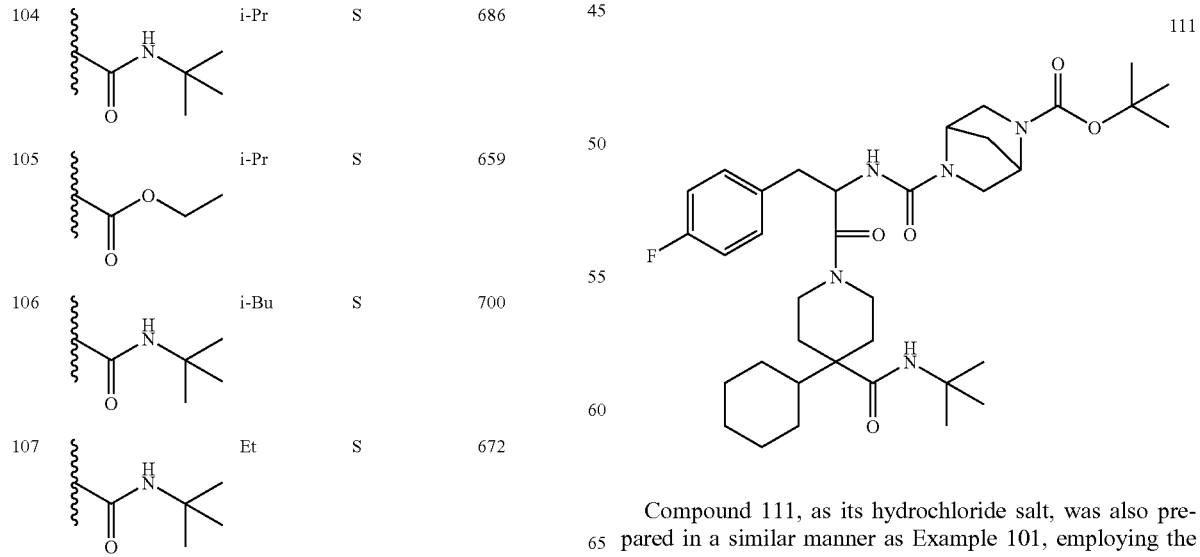

EXAMPLE 111

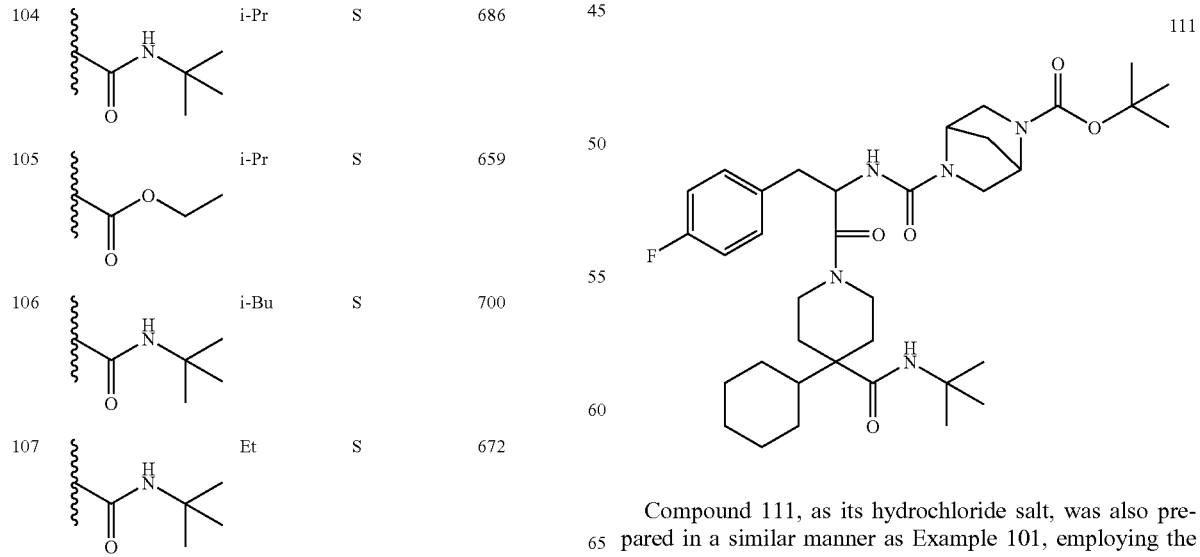

Compound 111, as its hydrochloride salt, was also prepared in a similar manner as Example 101, employing the appropriate piperidine and piperazine intermediates. ES-MS: Calcd. for C$_{36}$H$_{54}$FN$_5$O$_5$: 655.41. Found 656 (M+H).

EXAMPLE 112

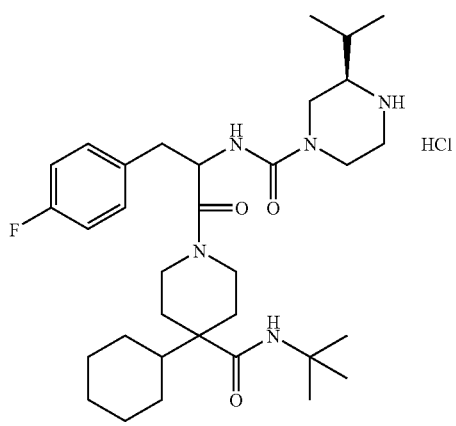

112

The compound of Example 101 (0.28 g, 0.41 mmol) was dissolved in 1.0 mL of CH$_2$Cl$_2$ and 1.0 mL of trifluoroacetic acid. This solution was stirred for 30 min at room temperature and then concentrated, washed with 5 mL of 1 N NaOH solution, dried over K$_2$CO$_3$, filtered and concentrated. Purification by column chromatography (3% to 20% MeOH—CH$_2$Cl$_2$) gave a white foamy-solid. To the solution of this base in 0.5 mL of CH$_2$Cl$_2$ was added 1 M HCl in ethyl ether (0.41 mL, 0.41 mmol). The precipitate was concentrated to give compound 112 as a white solid.

The following compounds of structural formula XI, as their hydrochloride salts, were also prepared in a similar manner as Example 112, employing the appropriate piperidine and piperazine intermediates:

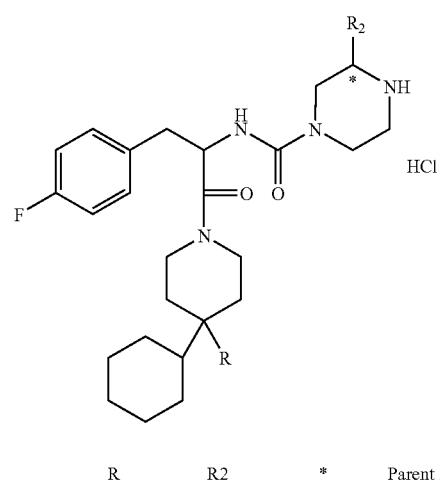

(XI)

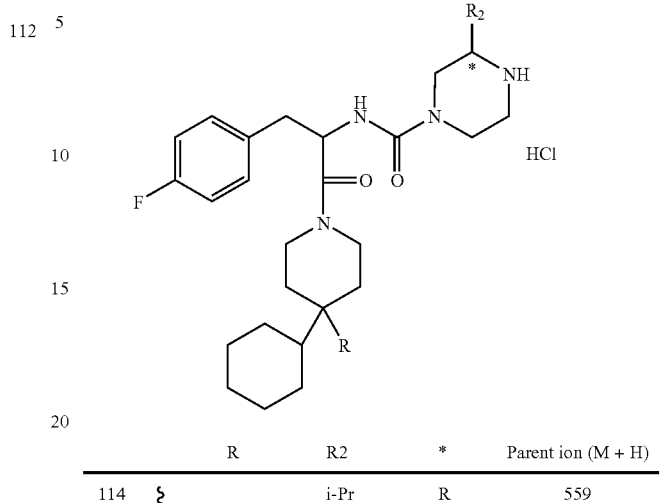

| | R | R2 | * | Parent ion (M + H) |
|---|---|---|---|---|
| 113 | ![NHtBu amide] | i-Pr | R | 586 |
| 114 | ![OEt ester] | i-Pr | R | 559 |
| 115 | ![NHtBu amide] | i-Pr | S | 586 |
| 116 | ![OEt ester] | i-Pr | S | 559 |
| 117 | ![NHtBu amide] | i-Bu | S | 600 |
| 118 | ![NHtBu amide] | Et | S | 572 |
| 119 | ![NHtBu amide] | Me | S | 558 |
| 120 | ![NHtBu amide] | di-Me | | 572 |
| 121 | ![NHtBu amide] | cyclopropyl | | 570 |

EXAMPLE 122

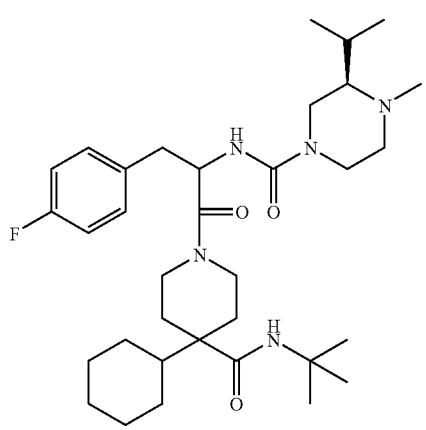

The compound of Example 103 (0.16 g, 0.23 mmol) in 1.2 mL of 1:1 TFA-CH$_2$Cl$_2$ was stirred at room temperature for 0.5 h, and then concentrated. This TFA salt was dissolved in 1.2 mL of MeOH and then sodium acetate (0.09 g, 1.15 mmol) and formaldehyde (0.08 mL, 1.1 mmol) were added. After 20 min, sodium cyanoborohydride (1.0 M solution in THF, 0.74 mL, 0.74 mmol) was added and stirred at room temperature overnight. This mixture was concentrated and the resulting slurry was dissolved in EtOAc, washed with 1 N NaOH and brine, dried over MgSO$_4$, filtered, and concentrated. Purification by column chromatography (3% to 10% MeOH—CH$_2$Cl$_2$) gave compound 122 as a white foamy-solid. ES-MS: Calcd. for C$_{34}$H$_{54}$FN$_5$O$_3$: 599.42. Found 600 (M+H).

EXAMPLE 123

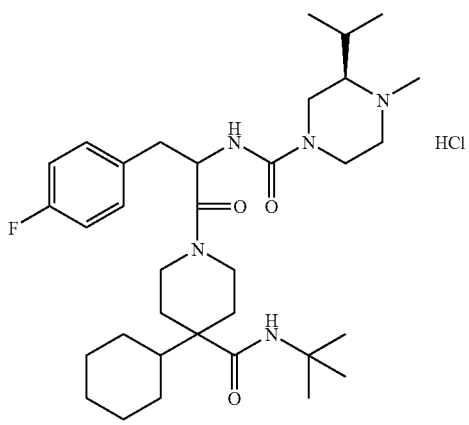

The compound of Example 122 (0.1 g, 0.17 mmol) was diluted with 0.5 mL of CH$_2$Cl$_2$ and then 1 M HCl solution in ethyl ether (0.20 ml, 0.20 mmol) was used. The precipitate was concentrated to give compound 123 as a white solid. ES-MS: Calcd. for C$_{34}$H$_{541}$N$_5$O$_3$: 599.42. Found: 600 (M+H).

EXAMPLE 124

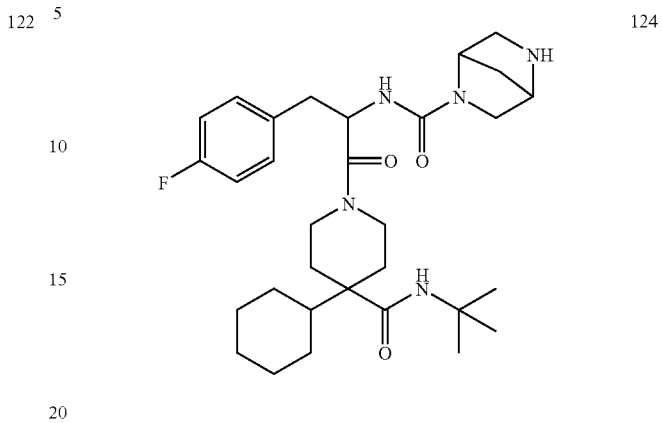

The compound of Example 111 (0.39 g, 0.60 mmol) was diluted with 3.0 mL of 1:1 TFA-CH$_2$Cl$_2$ solution and stirred at room temperature for 0.5 h. The mixture was concentrated, washed with 5 mL of 1 N NaOH solution, dried over K$_2$CO$_3$, filtered and concentrated to give compound 124 as a white foamy-solid.

ES-MS: Calcd. for C$_{31}$H$_{46}$FN$_5$O$_3$: 555.36. Found 556 (M+H).

The following compounds of structural formula XII, as their hydrochloride salts, were also prepared in a similar manner as Example 124, employing the appropriate piperidine and piperazine intermediates:

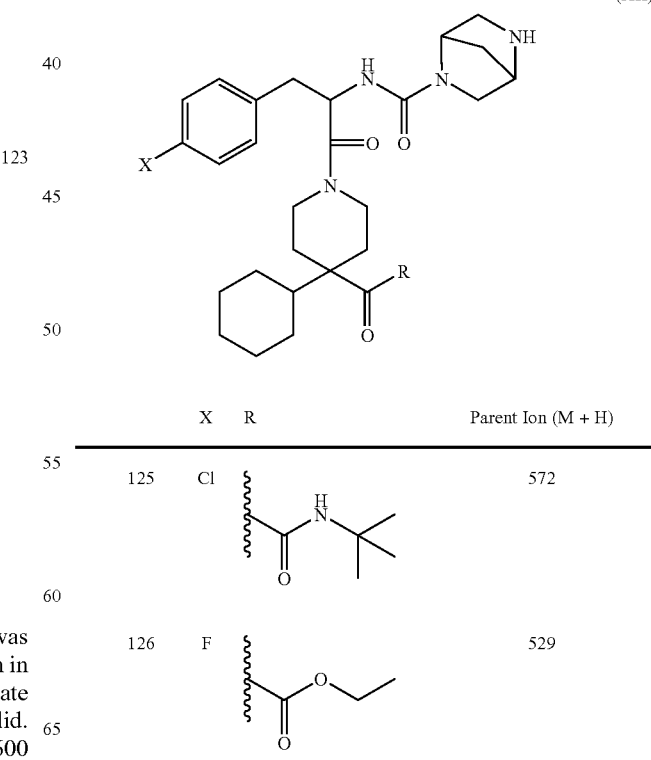

| | X | R | Parent Ion (M + H) |
|---|---|---|---|
| 125 | Cl | | 572 |
| 126 | F | | 529 |

EXAMPLE 129

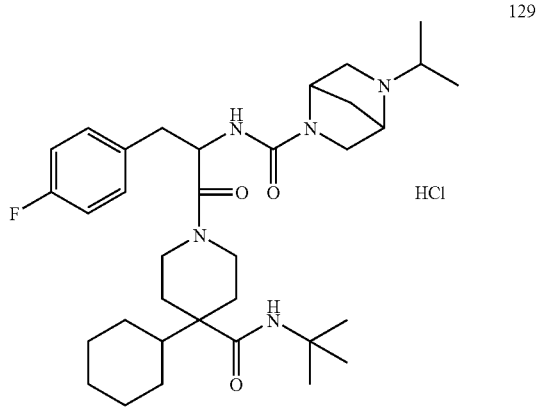

The compound of Example 128 (0.11 g, 0.19 mmol) was diluted with 0.7 mL of CH$_2$Cl$_2$ and then 1 M HCl solution in ethyl ether (0.22 ml, 0.22 mmol) was added. The precipitate was concentrated to give compound 129 as a white solid. ES-MS: Calcd for C$_{34}$H$_{52}$FN$_5$O$_3$: 597.41. Found 598 (M+H).

The compounds of structural formula XIII were synthesized in a similar fashion to that of Compound 129 using formaldehyde, acetaldehyde or acetone in the reductive amination step to make Compound 128.

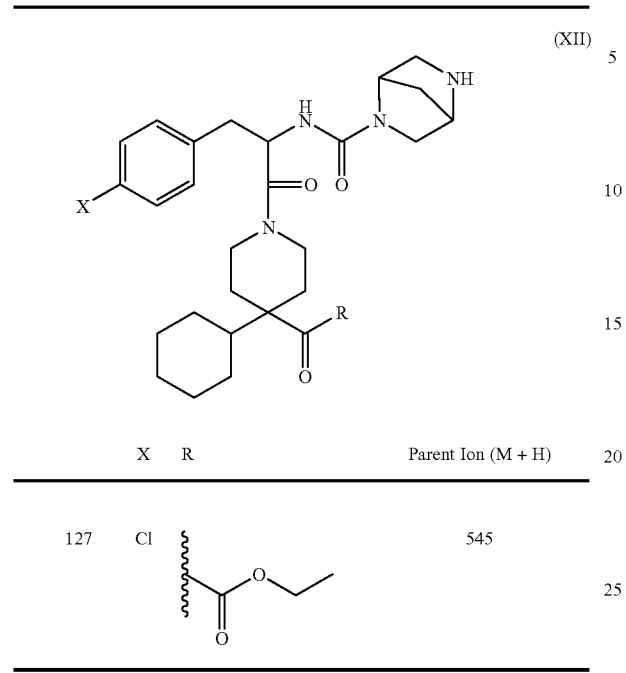

| | X | R | Parent Ion (M + H) |
|---|---|---|---|
| 127 | Cl | (ethyl ester) | 545 |

EXAMPLE 128

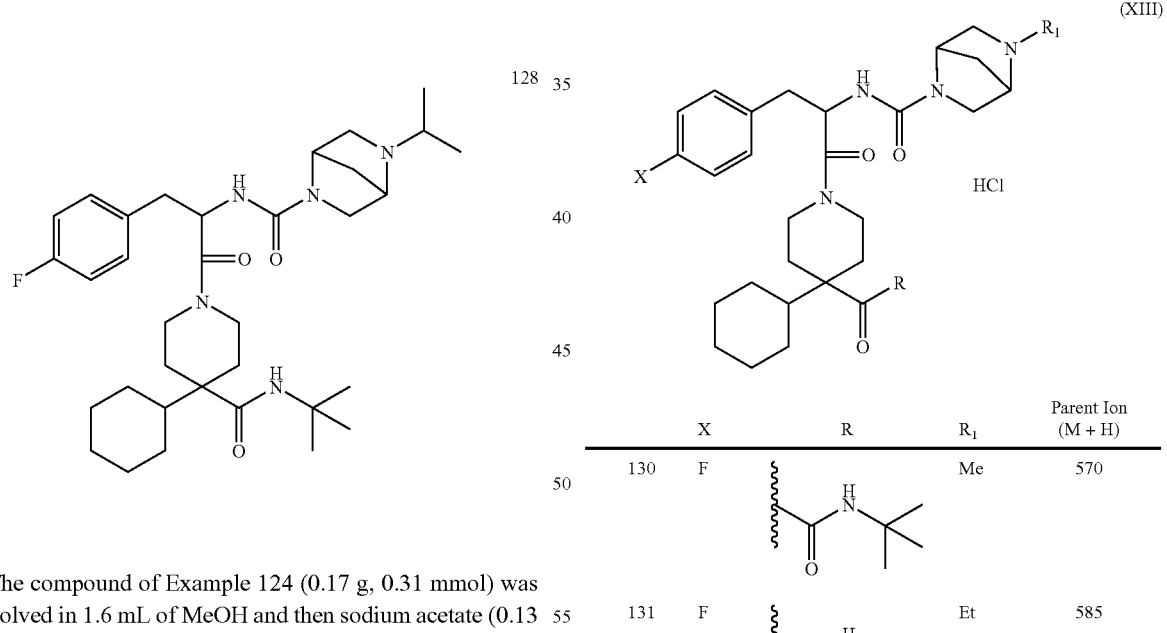

| | X | R | R$_1$ | Parent Ion (M + H) |
|---|---|---|---|---|
| 130 | F | (C(O)NH-tBu) | Me | 570 |
| 131 | F | (C(O)NH-tBu) | Et | 585 |
| 132 | Cl | (C(O)NH-tBu) | Me | 586 |

The compound of Example 124 (0.17 g, 0.31 mmol) was dissolved in 1.6 mL of MeOH and then sodium acetate (0.13 g, 1.55 mmol), trifluoroacetic acid (0.02 mL, 0.31 mmol), and acetone (0.11 mL, 1.50 mmol) were added. After 20 min, sodium cyano-borohydride (1.0 M solution in THF, 1.0 mL, 1.0 mmol) was added and stirred at room temperature overnight. This mixture was concentrated and the resulting slurry was dissolved in EtOAc, washed with 1 N NaOH and brine, dried over MgSO$_4$, filtered, and concentrated. Purification by column chromatography (3% to 20% MeOH—CH$_2$Cl$_2$) gave compound 128 as a white foamy-solid. ES-MS: Calcd for C$_{34}$H$_{52}$FN$_5$O$_3$: 597.41. Found 598 (M+H).

-continued

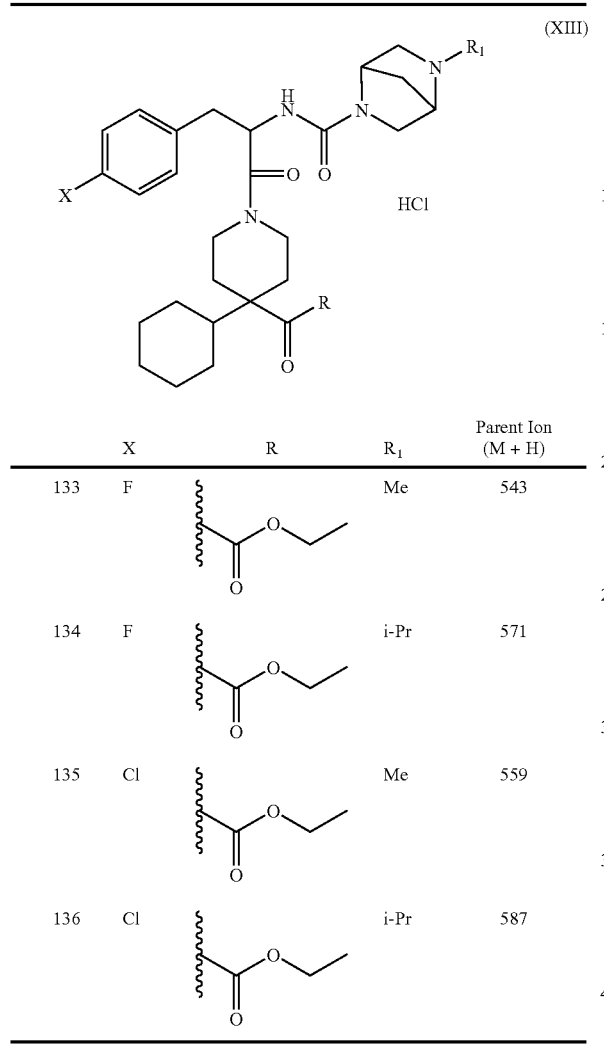

(XIII)

| | X | R | $R_1$ | Parent Ion (M + H) |
|---|---|---|---|---|
| 133 | F | ethyl ester | Me | 543 |
| 134 | F | ethyl ester | i-Pr | 571 |
| 135 | Cl | ethyl ester | Me | 559 |
| 136 | Cl | ethyl ester | i-Pr | 587 |

EXAMPLE 137

137

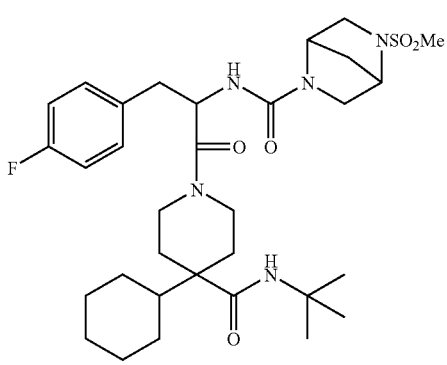

The TFA salt of compound 124 (0.060 g, 0.090 mmol) was dissolved in 0.9 mL of $CH_2Cl_2$ and purged under nitrogen. The mixture was cooled at 0° C. in an ice-water bath and then triethylamine (0.05 mL, 0.360 mmol) and methanesulfonyl chloride (0.008 mL, 0.108 mmol) were then added. The mixture was stirred at 0° C. for 9 min, warmed to room temperature, and stirred at room temperature. After 68.5 h, the mixture was diluted with $CH_2Cl_2$ and washed twice with 1N HCl solution, sat. $NaHCO_3$ solution, water, and brine, dried over sodium sulfate, filtered and concentrated to give a clear oil. Purification by column chromatography (1:1 $CH_2Cl_2$-acetone) gave compound 137 as a white solid. ES-MS: Calcd for $C_{32}H_{48}FN_5O_5S$: 633.82. Found 634 (M+H).

EXAMPLE 138

138

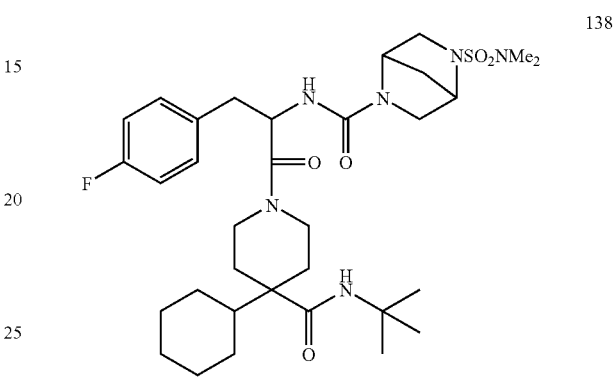

The TFA salt of compound 124 (0.060 g, 0.090 mmol) was dissolved in 0.9 mL of $CH_2Cl_2$ and purged under nitrogen. The mixture was cooled at 0° C. in an ice-water bath and then triethylamine (0.05 mL, 0.360 mmol) and dimethylsulfamoyl chloride (0.012 mL, 0.108 mmol) were then added. The mixture was stirred at 0° C. for 7 min, warmed to room temperature, and stirred at room temperature. After 68.5 h, the mixture was diluted with $CH_2Cl_2$ and washed twice with 1N HCl solution, sat. $NaHCO_3$ solution, water, and brine, dried over sodium sulfate, filtered and concentrated to give a clear oil. Purification by column chromatography (1:1 $CH_2Cl_2$-acetone) gave compound 138 as a white solid. ES-MS: Calcd for $C_{33}H_{51}FN_6O_5S$: 662.86. Found 663 (M+H).

BIOLOGICAL ASSAYS

A. Binding Assay.

The membrane binding assay was used to identify competitive inhibitors of $^{125}$I-NDP-alpha-MSH binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BR1); 100 mL 10% heat-inactivated fetal bovine serum (Sigma); 10 mL 10,000 unit/mL penicillin & 10,000 µg/ml streptomycin (Gibco/BR1); 10 mL 200 mM L-glutamine (Gibco/BR1); 1 mg/mL geneticin (G418) (Gibco/BR1). The cells were grown at 37° C. with $CO_2$ and humidity control until the desired cell density and cell number was obtained.

The medium was poured off and 10 mLs/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mLs/monolayer membrane preparation buffer having the composition:

10 mM Tris pH 7.2-7.4; 4 μg/mL Leupeptin (Sigma); 10 μM Phosphoramidon (Boehringer Mannheim); 40 μg/mL Bacitracin (Sigma); 5 μg/mL Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mLs/monolayer membrane prep buffer and aliquots were placed in tubes (500-1000 μL/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM $CaCl_2$; 1 mM $MgCl_2$; 5 mM KCl; 0.2% BSA; 4 μg/mL Leupeptin (SIGMA); 10 μM Phosphoramidon (Boehringer Mannheim); 40 μg/mL Bacitracin (SIGMA); 5 μg/mL Aprotinin (SIGMA); and 10 mM Pefabloc (Boehringer Mannheim). One hundred μL of membrane binding buffer containing 10-40 μg membrane protein was added, followed by 100 μM 125I-NDP-α-MSH to final concentration of 100 pM. The resulting mixture, was vortexed briefly and incubated for 90-120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 μL of Packard Microscint-20 was added to each well. The top was sealed and the radioactivity quantitated in a Packard Topcount Microplate Scintillation counter.

B. Functional Assay.

Functional cell based assays were developed to discriminate melanocortin receptor agonists from antagonists.

Cells (for example, CHO- or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997 March; 11(3): 274-80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/mL bovine serum albumin. Cells were counted and diluted to 1 to $5 \times 10^6$/mL. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min, and an $EC_{50}$ dose (approximately 10 nM alpha-MSH) was added to the cells. The assay was terminated at 45 min and cAMP quantitated as above. Percent inhibition was determined by comparing the amount of cAMP produced in the presence to that produced in the absence of test compound.

Representative compounds of the present invention were tested and found to bind to the melanocortin-4 receptor. These compounds were generally found to have $IC_{50}$ values less than 2 μM. Representative compounds of the present invention were also tested in the functional assay and found generally to activate the melanocortin-4 receptor with $EC_{50}$ values less than 1 μM.

C. In Vivo Food Intake Models.

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 h post compound administration is measured.

2) Food intake in diet induced obese mice. Male C57/B16J mice maintained on a high fat diet (60% fat calories) for 6.5 months from 4 weeks of age are dosed intraperitoneally with test compound. Food intake and body weight are measured over an eight day period. Biochemical parameters relating to obesity, including leptin, insulin, triglyceride, free fatty acid, cholesterol and serum glucose levels are determined.

EXAMPLES Of A PHARMACEUTICAL COMPOSITION

As a specific embodiment of an oral composition of a composition of the present invention, 5 mg of Example 1 is formulated with sufficient finely divided lactose to provide a total amount of 580 to 590 mg to fill a size O hard gelatin capsule.

As another specific embodiment of an oral composition of a compound of the present invention, 10 mg of Example 2 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I:

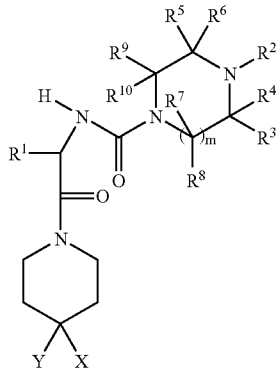

or a pharmaceutically acceptable salt thereof; wherein
m is 1 or 2;
each p is independently 0, 1, or 2;
each n is independently 0, 1, or 2;
$R^1$ is 4-chlorobenzyl; 4-fluorobenzyl; 3,4-difluorobenzyl; 3,5-difluorobenzyl, 2-cyano-4-fluorobenzyl; or 4-methoxybenzyl;
$R^3$, $R^4$, $R^5$, $R^6$, $R^7$, $R^8$, $R^9$, and $R^{10}$ are each independently selected from the group consisting Of:
  hydrogen,
  $C_{1-8}$ alkyl,
  $(CH_2)_n$-aryl,
  $(CH_2)_nC_{3-6}$ cycloalkyl,
  $(CH_2)_n$-heteroaryl, and
  $(CH_2)_n$-heterocyclyl;
in which aryl and heteroaryl are unsubstituted or substituted with one to three groups independently selected from $R^{11}$; and alkyl, cycloalkyl, and heterocyclyl are unsubstituted or substituted with one to three groups independently selected from $R^{11}$ and oxo;
  or $R^3$ and $R^5$ and the carbon atoms to which they are attached form a 5- to 7-membered ring;
  or $R^3$ and $R^9$ and the carbon atoms to which they are attached form a 5- to 7-membered ring;
  or $R^5$ and $R^7$ and the carbon atoms to which they are attached form a 5- to 7-membered ring;
  or $R^7$ and $R^9$ and the carbon atoms to which they are attached form a 5- to 7-membered ring;
$R^2$ is selected from the group consisting of
  hydrogen,
  $C_{2-6}$ alkenyl,
  $C_{1-8}$ alkyl,
  $(CH_2)_n$-aryl,
  $(CH_2)_nC_{3-6}$ cycloalkyl,
  $(CH_2)_n$-heteroaryl,
  $(CH_2)_n$-heterocyclyl,
  $(CH_2)_{1-2}OR^{12}$,
  $(CH_2)_{1-2}CO_2R^{12}$,
  $(CH_2)_{1-2}CONR^{12}R^{12}$,
  $CH_2C\equiv CH$, and
  $CH_2CHF_2$;
in which aryl and heteroaryl are unsubstituted or substituted with one to three groups independently selected from $R^{11}$; and alkyl, cycloalkyl, and heterocyclyl are unsubstituted or substituted with one to three groups independently selected from $R^{11}$ and oxo;
  or $R^2$ and $R^3$ and the carbon atoms to which they are attached form a 5- to 7-membered ring;
  or $R^3$ and $R^4$ and the carbon atom to which they are attached form a 3- to 6-membered spirocyclic ring;
$R^{11}$ is selected from the group consisting of
  hydrogen,
  $C_{1-6}$ alkyl,
  $(CH_2)_n$-phenyl,
  $(CH_2)_n$-naphthyl,
  $(CH_2)_n$-heteroaryl,
  $(CH_2)_n$-heterocyclyl,
  $(CH_2)_nC_{3-7}$ cycloalkyl,
  halogen,
  $OR^{12}$,
  $(CH_2)_nN(R^{12})_2$,
  $(CH_2)_nC\equiv N$,
  $(CH_2)_nCO_2R^{12}$,
  $NO_2$,
  $(CH_2)_nNR^{12}SO_2R^{12}$,
  $(CH_2)_nSO_2N(R^{12})_2$,
  $(CH_2)_nS(O)_pR^{12}$,
  $(CH_2)_nNR^{12}C(O)N(R^{12})_2$,
  $(CH_2)_nC(O)N(R^{12})_2$,
  $(CH_2)_nNR^{12}C(O)R^{12}$,
  $(CH_2)_nNR^{12}CO_2R^{12}$,
  $O(CH_2)_nC(O)N(R^{12})_2$,
  $CF_3$,
  $CH_2CF_3$,
  $OCF_3$, and
  $OCH_2CF_3$;
wherein phenyl, naphthyl, heteroaryl, cycloalkyl, and heterocyclyl are unsubstituted or substituted with one to three substituents independently selected from halogen, hydroxy, $C_{1-4}$ alkyl, trifluoromethyl, and $C_{1-4}$ alkoxy; and wherein any methylene ($CH_2$) carbon atom in $R^{11}$ is unsubstituted or substituted with one to two groups independently selected from halogen, hydroxy, and $C_{1-4}$ alkyl; or two substituents when on the same methylene ($CH_2$) carbon atom are taken together with the carbon atom to which they are attached to form a cyclopropyl group;
  each $R^{12}$ is independently selected from the group consisting of
    hydrogen,
    $C_{1-8}$ alkyl,
    $(CH_2)_n$-phenyl,
    $(CH_2)_n$-naphthyl,
    $(CH_2)_n$-heteroaryl, and
    $(CH_2)_nC_{3-7}$ cycloalkyl;
  wherein any methylene ($CH_2$) carbon atom in $R^{12}$ is unsubstituted or substituted with one to two groups independently selected from halogen, hydroxy, and $C_{1-4}$ alkyl; or two $R^{12}$ groups together with the atom to which they are attached form a 5- to 8-membered mono- or bicyclic ring system optionally containing an additional heteroatom selected from O, S, and $NC_{1-4}$ alkyl;
    each $R^{13}$ is independently selected from the group consisting of
      hydrogen,
      $C_{1-8}$ alkyl,
      $(CH_2)_n$-aryl,
      $(CH_2)_n$-heteroaryl,
      $(CH_2)_n$-heterocyclyl, and
      $(CH_2)_nC_{3-7}$ cycloalkyl;
  wherein alkyl, aryl, heteroaryl, heterocyclyl, and cycloalkyl are unsubstituted or substituted with one to three groups independently selected from halogen, hydroxy, $C_{1-3}$ alkoxy, $C_{1-3}$ alkylthio, carboxy, $C_{1-4}$ alkyloxycarbonyl, amino, $C_{1-4}$ alkylamino, and di($C_{1-4}$ alkylamino);

or two $R^{13}$ groups together with the atoms to which they are attached form a 5- to 8-membered mono- or bi-cyclic ring system optionally containing an additional heteroatom selected from O, S, $NR^{12}$, NBoc, and NCbz;

X is selected from the group consisting of
$C_{1-8}$ alkyl,
$(CH_2)_nC_{3-8}$ cycloalkyl,
$(CH_2)_n$-phenyl,
$(CH_2)_n$-naphthyl,
$(CH_2)_n$-heteroaryl,
$(CH_2)_n$heterocyclyl,
$(CH_2)_nC{\equiv}N$,
$(CH_2)_nCON(R^{13}R^{13})$,
$(CH_2)_nCO_2R^{13}$,
$(CH_2)_nCOR^{13}$,
$(CH_2)_nNR^{13}C(O)R^{13}$,
$(CH_2)_nNR^{13}CO_2R^{13}$,
$(CH_2)_nNR^{13}C(O)N(R^{13})_2$,
$(CH_2)_nNR^{13}SO_2R^{13}$,
$(CH_2)_nS(O)_pR^{13}$,
$(CH_2)_nSO_2N(R^{13})(R^{13})$,
$(CH_2)_nOR^{13}$,
$(CH_2)_nOC(O)R^{13}$,
$(CH_2)_nOC(O)OR^{13}$,
$(CH_2)_nOC(O)N(R^{13})_2$,
$(CH_2)_nN(R^{13})(R^{13})$, and
$(CH_2)_nNR^{13}SO_2N(R^{13})(R^{13})$;

wherein phenyl, naphthyl, and heteroaryl are unsubstituted or substituted with one to three groups independently selected from $R^{11}$; alkyl, cycloalkyl, and heterocyclyl are unsubstituted or substituted with one to three groups independently selected from $R^{11}$ and oxo; and wherein any methylene ($CH_2$) carbon atom in X is unsubstituted or substituted with one to two groups independently selected from halogen, hydroxy, and $C_{1-4}$ alkyl; and Y is $C_{1-8}$ alkyl, $(CH_2)_nC_{3-7}$ cycloalkyl, $(CH_2)_n$-aryl, $(CH_2)_n$- heterocyclyl, or $(CH_2)_n$-heteroaryl; wherein aryl and heteroaryl are unsubstituted or substituted with one to three groups independently selected from $R^{11}$; and $(CH_2)_n$ alkyl, cycloalkyl, and heterocyclyl are unsubstituted or substituted with one to three groups independently selected from $R^{11}$ and oxo.

2. The compound of claim 1 wherein $R^2$ is selected from the group consisting of
hydrogen,
$C_{1-8}$ alkyl,
$CH_2$-aryl,
$CH_2$-heteroaryl,
$CH_2$-heterocyclyl,
$CH_2C_{3-6}$ cycloalkyl,
$CH_2CO_2R^{12}$,
$CH_2CONR^{12}R^{12}$,
$CH_2OR^{12}$,
$CH_2C{\equiv}CH$, and
$CH_2CHF_2$;
wherein aryl and heteroaryl are unsubstituted or substituted with one to three groups independently selected from $R^{11}$; and alkyl, cycloalkyl, and heterocyclyl are unsubstituted or substituted with one to three groups independently selected from $R^{11}$ and oxo.

3. The compound of claim 2 wherein $R^2$ is hydrogen or $C_{1-4}$ alkyl.

4. The compound of claim 3 wherein $R^2$ is hydrogen.

5. The compound of claim 1 wherein X is selected from the group consisting of $C_{1-6}$ alkyl, $(CH_2)_n$-phenyl, $(CH_2)_n$-naphthyl, $(CH_2)_n$-heteroaryl, $(CH_2)_n$-heterocyclyl, $(CH_2)_nC(O)N(R^{13})(R^{13})$, $(CH_2)_nCO_2R^{13}$, $(CH_2)_nS(O)_pR^{13}$, $(CH_2)_nOR^{13}$, $(CH_2)_nNR^{13}C(O)R^{13}$, and $(CH_2)_nNR^{13}SO_2R^{13}$; wherein phenyl, naphthyl, and heteroaryl are unsubstituted or substituted with one to three groups independently selected from $R^{11}$; alkyl and heterocyclyl are unsubstituted or substituted with one to three groups independently selected from $R^{11}$ and oxo; and the $(CH_2)_n$ group is unsubstituted or substituted with one to three groups independently selected from $R^{12}$, halogen, $S(O)_pR^{12}$, $N(R^{12})_2$, and $OR^{12}$.

6. The compound of claim 5 wherein X is selected from the group consisting of $C_{1-6}$ alkyl, $(CH_2)_{0-1}$-phenyl, $(CH_2)_{0-1}$-heteroaryl, $(CH_2)_{0-1}$-heterocyclyl, $(CH_2)_{0-1}NHC(O)R^{13}$, $(CH_2)_{0-1}CO_2R^{13}$, and $(CH_2)_{0-1}C(O)N(R^{13})(R^{13})$; wherein phenyl and heteroaryl are unsubstituted or substituted with one to three groups independently selected from $R^{11}$; and alkyl and heterocyclyl are unsubstituted or substituted with one to three groups independently selected from $R^{11}$ and oxo.

7. The compound of claim 6 wherein heteroaryl is selected from the group consisting of pyridyl, pyrazinyl, pyrimidinyl, triazolyl, tetrazolyl, thiadiazolyl, oxadiazolyl, pyrazolyl, and imidazolyl.

8. The compound of claim 1 wherein Y is $C_{3-6}$ cycloalkyl or $C_{1-6}$ alkyl, wherein alkyl and cycloalkyl are unsubstituted or substituted with one to three groups independently selected from $R^{11}$ and oxo.

9. The compound of claim 8 wherein Y is cyclohexyl or $C_{1-6}$ alkyl, wherein the cyclohexyl and alkyl groups are unsubstituted or substituted with one to three groups independently selected from $R^{11}$ and oxo.

10. The compound of claim 1 wherein m is 1.

11. The compound of claim 1 wherein $R^3$, $R^4$, $R^5$, $R^6$, $R^7$, $R^8$, $R^9$, and $R^{10}$ are each independently hydrogen or $C_{1-4}$ alkyl; or $R^3$ and $R^5$ and the carbon atoms to which they are attached form a 5- to 7-membered ring; or $R^3$ and $R^9$ and the carbon atoms to which they are attached form a 5- to 7-membered ring.

12. The compound of claim 11 wherein $R^3$, $R^4$, $R^5$, and $R^6$ are each independently hydrogen or $C_{1-4}$ alkyl, and $R^7$, $R^8$, $R^9$, and $R^{10}$ are hydrogen.

13. The compound of claim 12 wherein $R^3$ and $R^5$ are each independently hydrogen or $C_{1-4}$ alkyl; and $R^4$ and $R^6$ are hydrogen.

14. A compound of structural formula II:

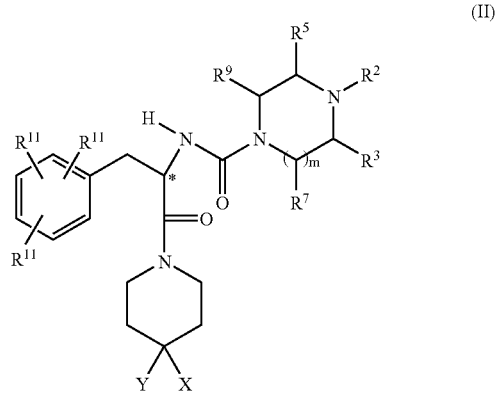

(II)

wherein m is 1 or 2;
each $R^{11}$ is independently selected from the group consisting of
 hydrogen,
 halogen,
 cyano,
 $C_{1-4}$ alkyl,
 $C_{1-4}$ alkoxy,
 $C_{1-4}$ alkylthio,
 trifluoromethyl, and
 trifluoromethoxy;
$R^2$ is hydrogen or $C_{1-4}$ alkyl, unsubstituted or substituted with one to three groups independently selected from $R^{11}$ and oxo;
$R^3$, $R^5$, $R^7$, and $R^9$ are each independently hydrogen or $C_{1-4}$ alkyl; or $R^3$ and $R^5$ and the carbon atoms to which they are attached form a 5- to 7-membered ring; or $R^3$ and $R^9$ and the carbon atoms to which they are attached form a 5- to 7-membered ring;
Y is $C_{5-7}$ cycloalkyl or $C_{1-6}$ alkyl, wherein alkyl and cycloalkyl are unsubstituted or substituted with one to three groups independently selected from $R^{11}$ and oxo; and
X is selected from the group consisting of

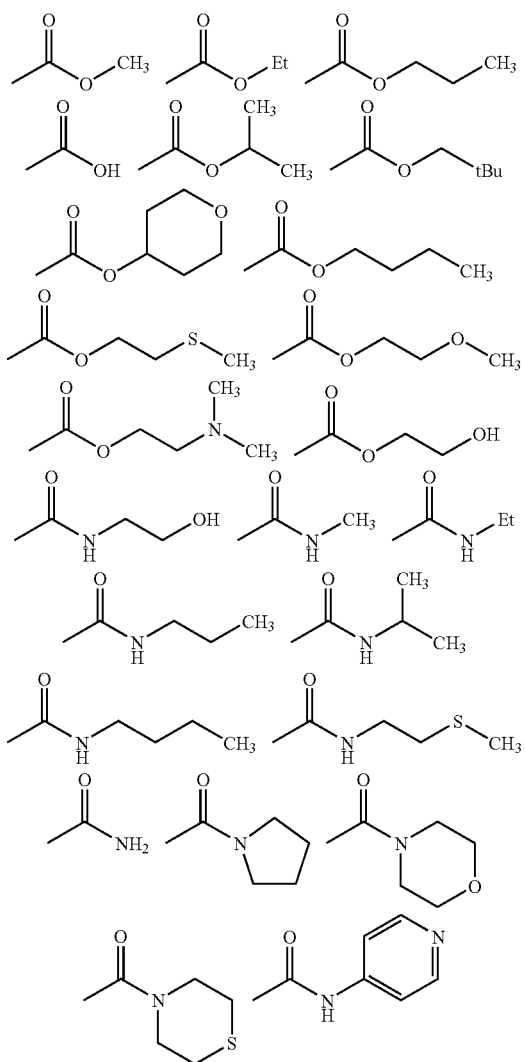

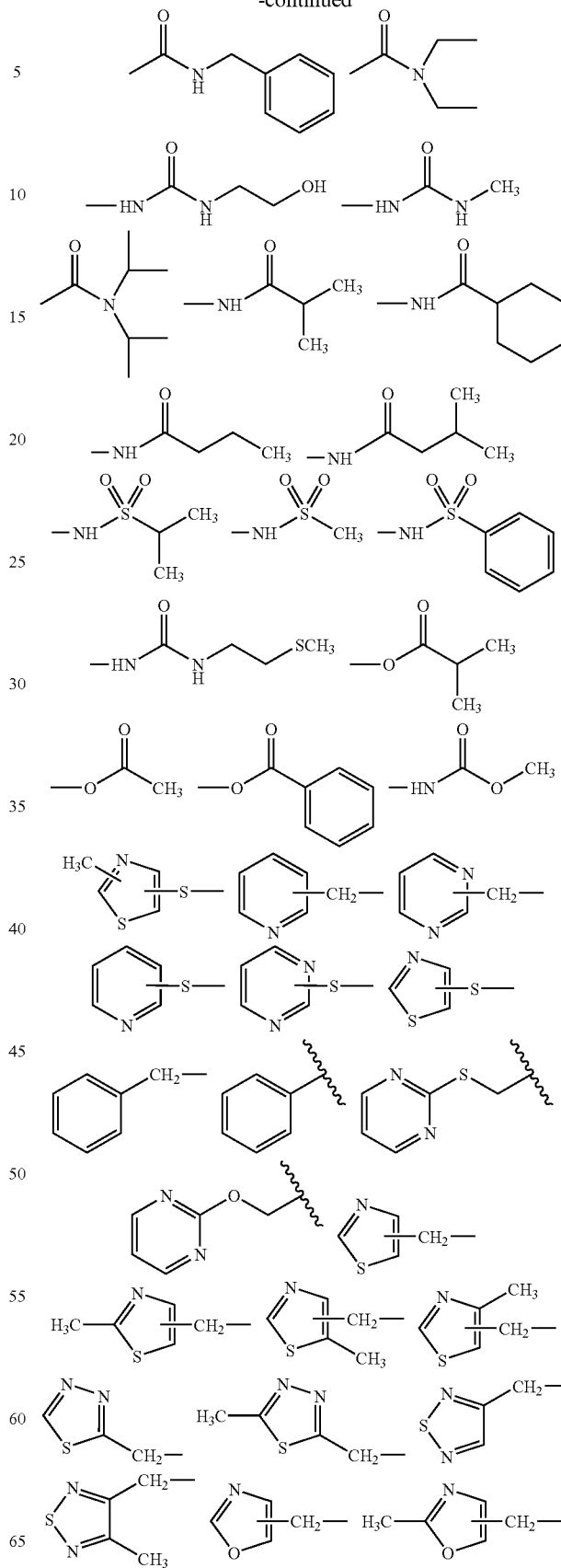

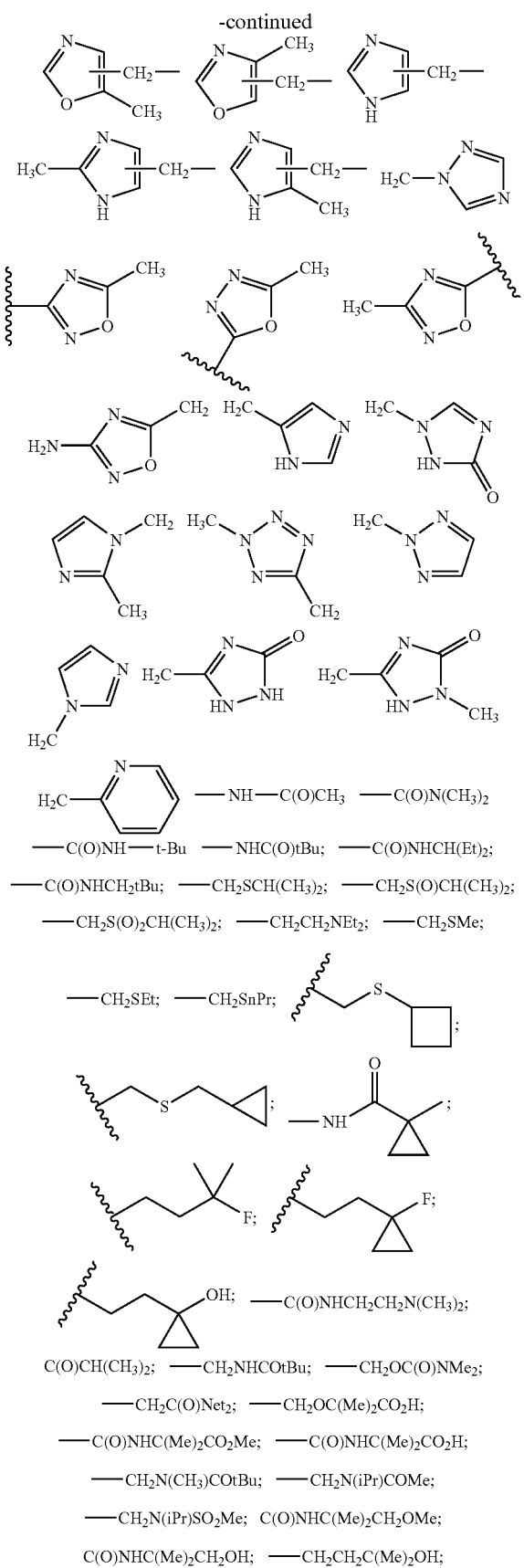
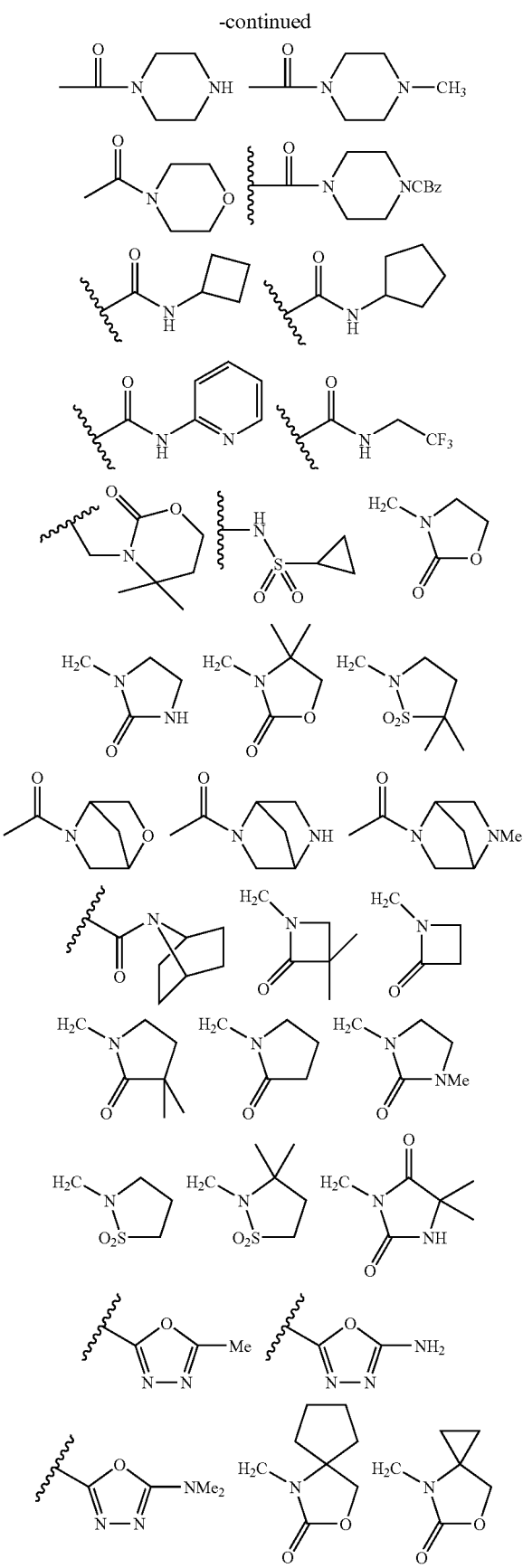

-continued
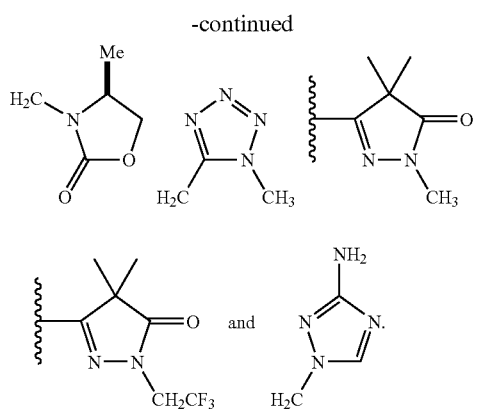
and
15. The compound of claim 14 wherein the carbon atom marked with * has the R configuration.
16. The compound of claim 14 wherein m is 1.
17. The compound of claim 14 wherein $R^3$ and $R^5$ are each independently hydrogen or $C_{1-4}$ alkyl, and $R^7$ and $R^9$ are hydrogen.
18. The compound of claim 15 of structural formula III selected from the group consisting of:
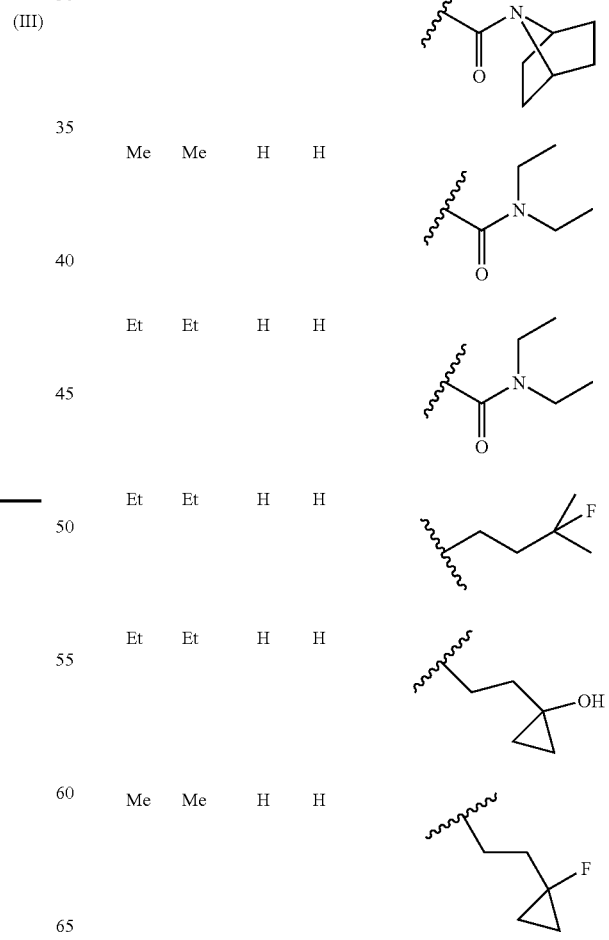
-continued
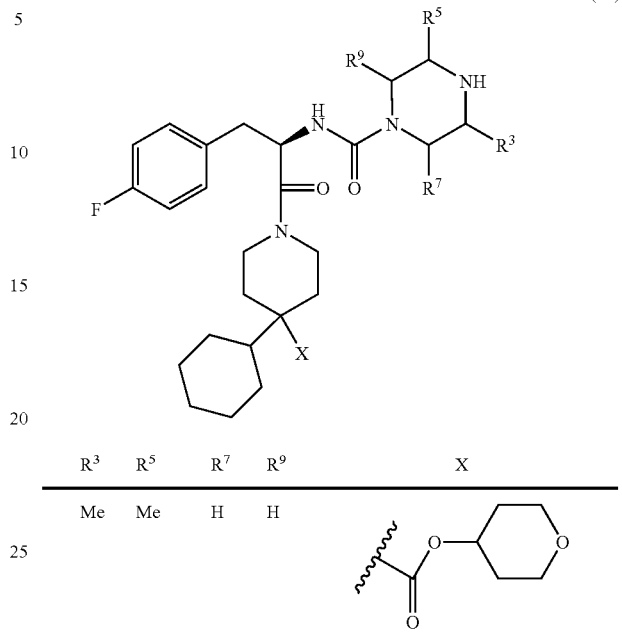

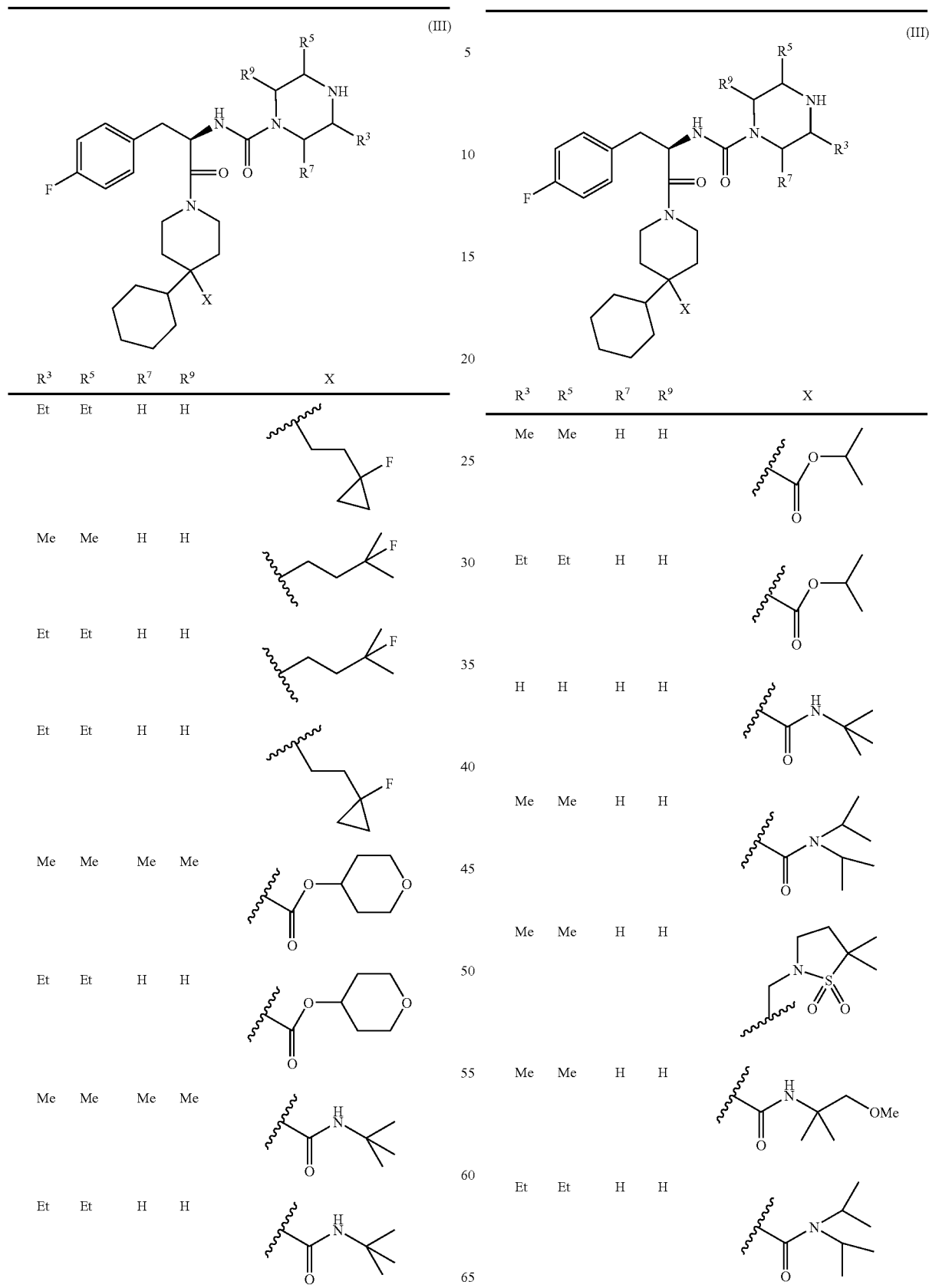

-continued
(III)
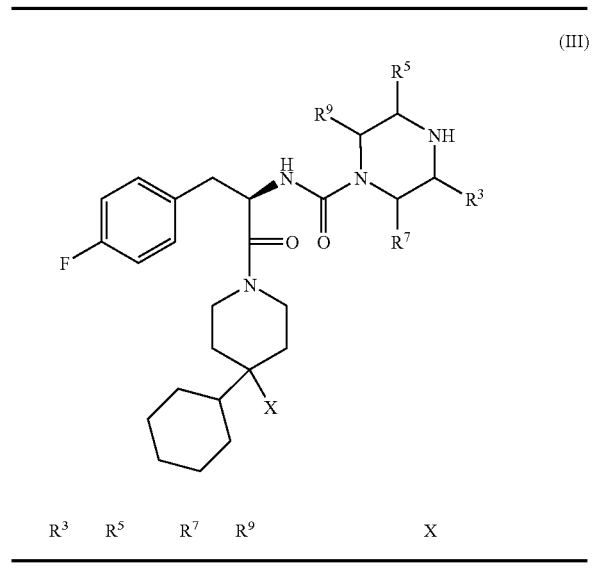
| R³ | R⁵ | R⁷ | R⁹ | X |
|----|----|----|----|---|
| Et | Et | H | H | 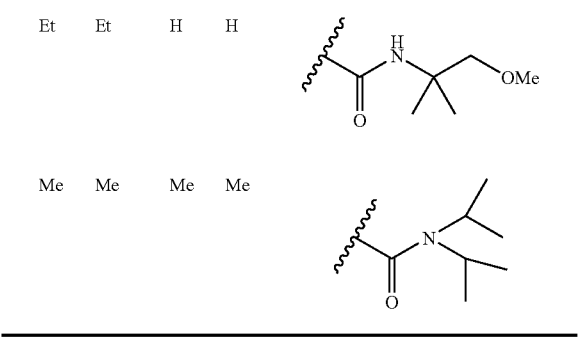 |
| Me | Me | Me | Me | |
or a pharmaceutically acceptable salt thereof.
19. The compound of claim 15 of structural formula IV selected from the group consisting of:
(IV)
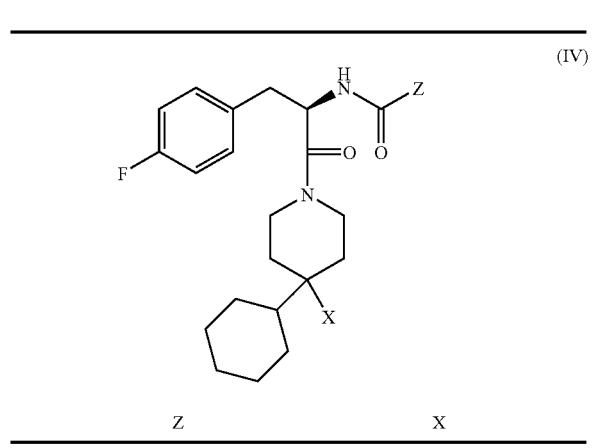
| Z | X |
|---|---|
| 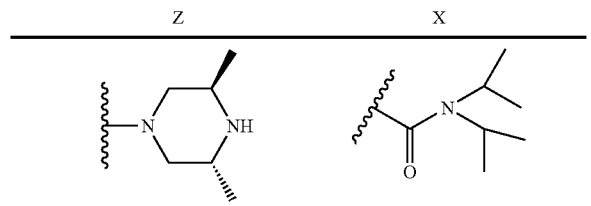 | |
-continued
(IV)
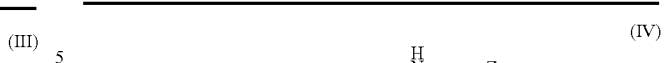
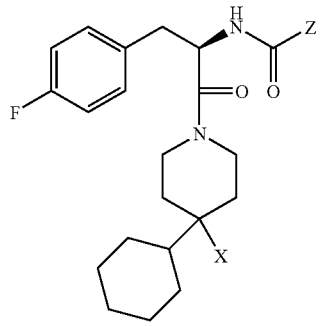
| Z | X |
|---|---|
| 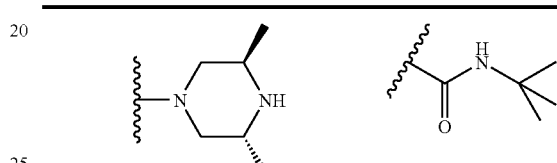 | |
| 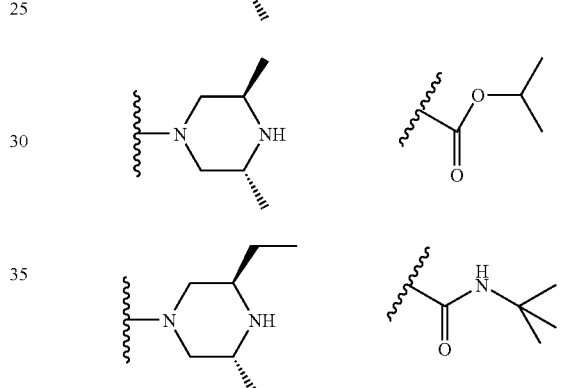 | |
| D1 | |
| 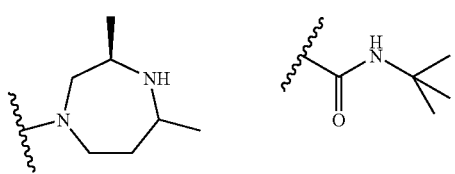 | |
| D2 | |
| 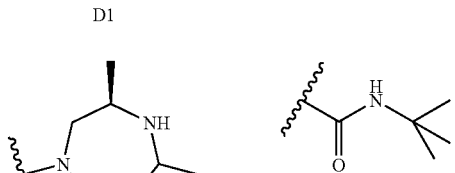 | |
| 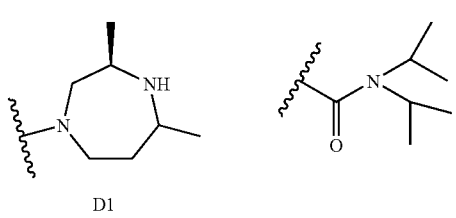 | |
| D1 | |

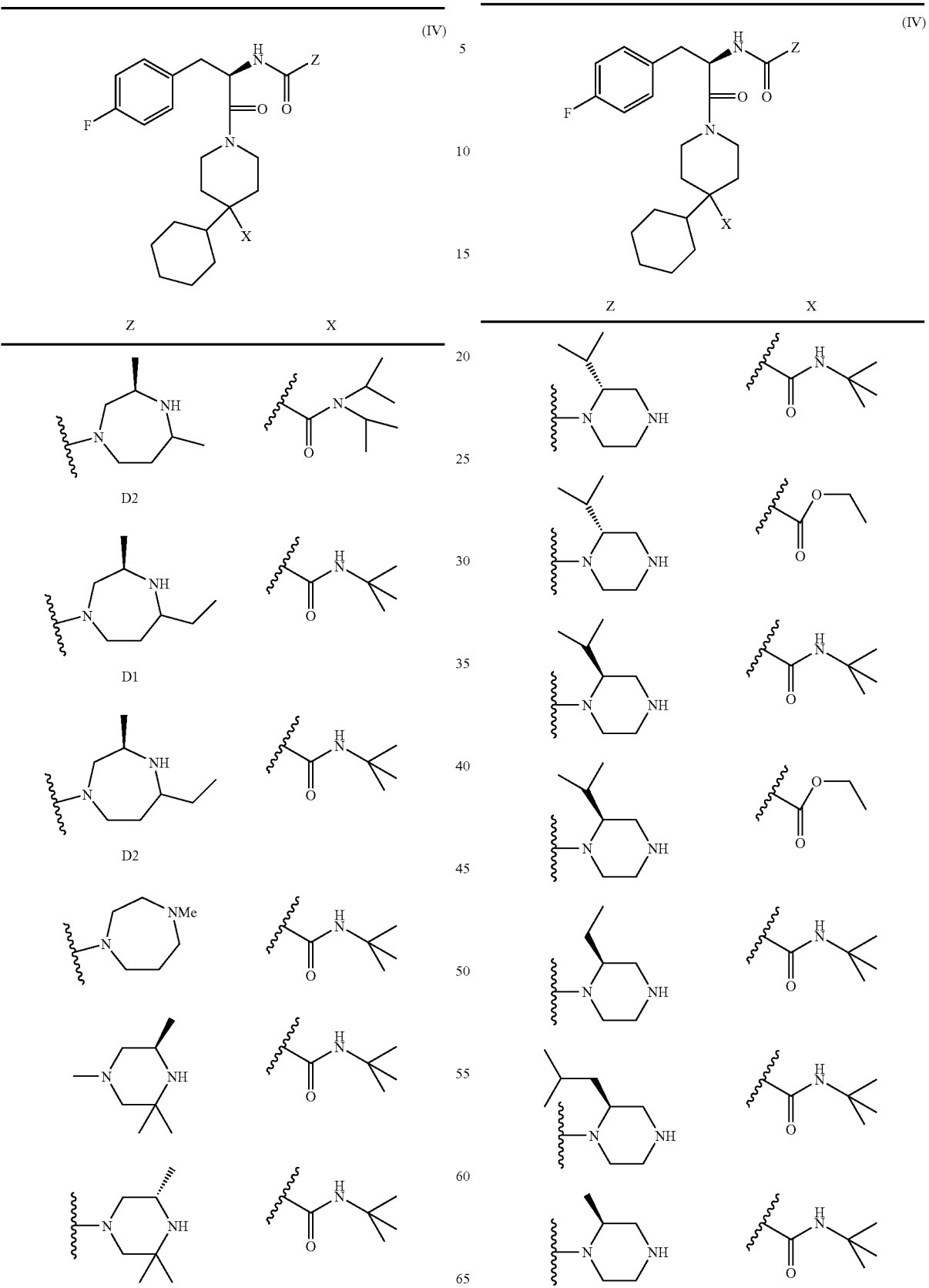

| 131 | 132 |
|---|---|
| -continued | -continued |
| (IV) 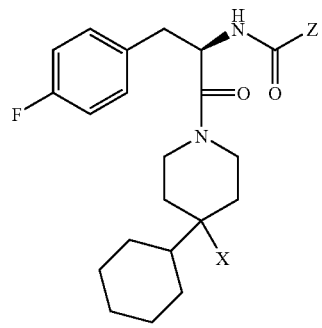 | (IV) 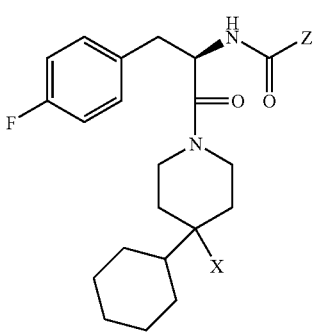 |
| Z | X | Z | X |
|---|---|---|---|
| 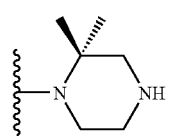 | 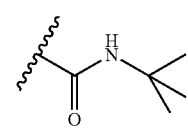 | 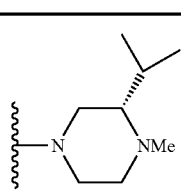 | 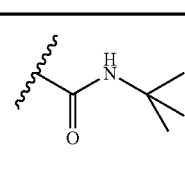 |
| 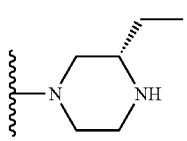 | 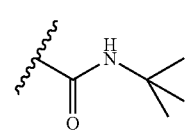 | 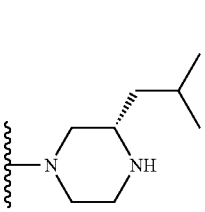 | 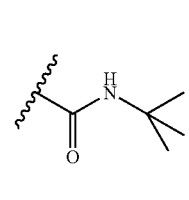 |
| 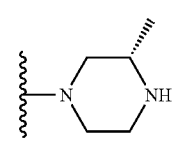 | 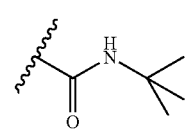 | 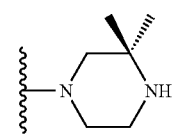 | 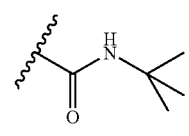 |
(additional rows on page 131 with isopropyl piperazine Z and tert-butyl amide / ethyl ester X groups)

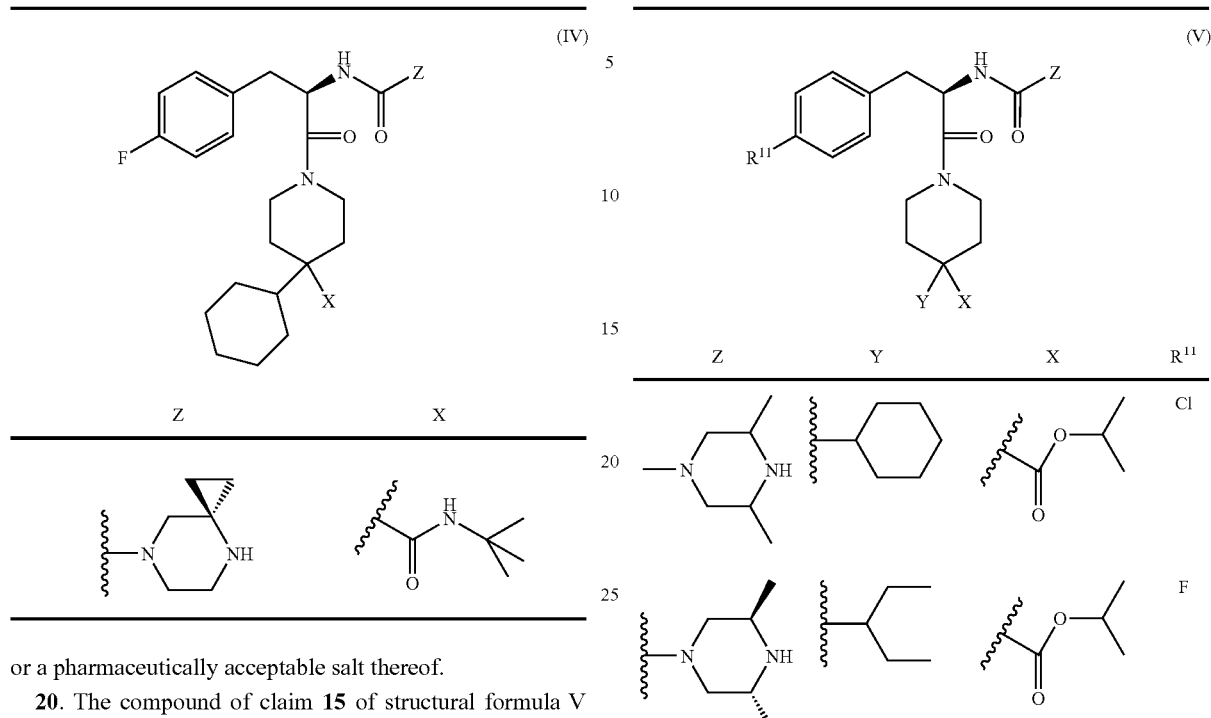
or a pharmaceutically acceptable salt thereof.
20. The compound of claim 15 of structural formula V selected from the group consisting of:
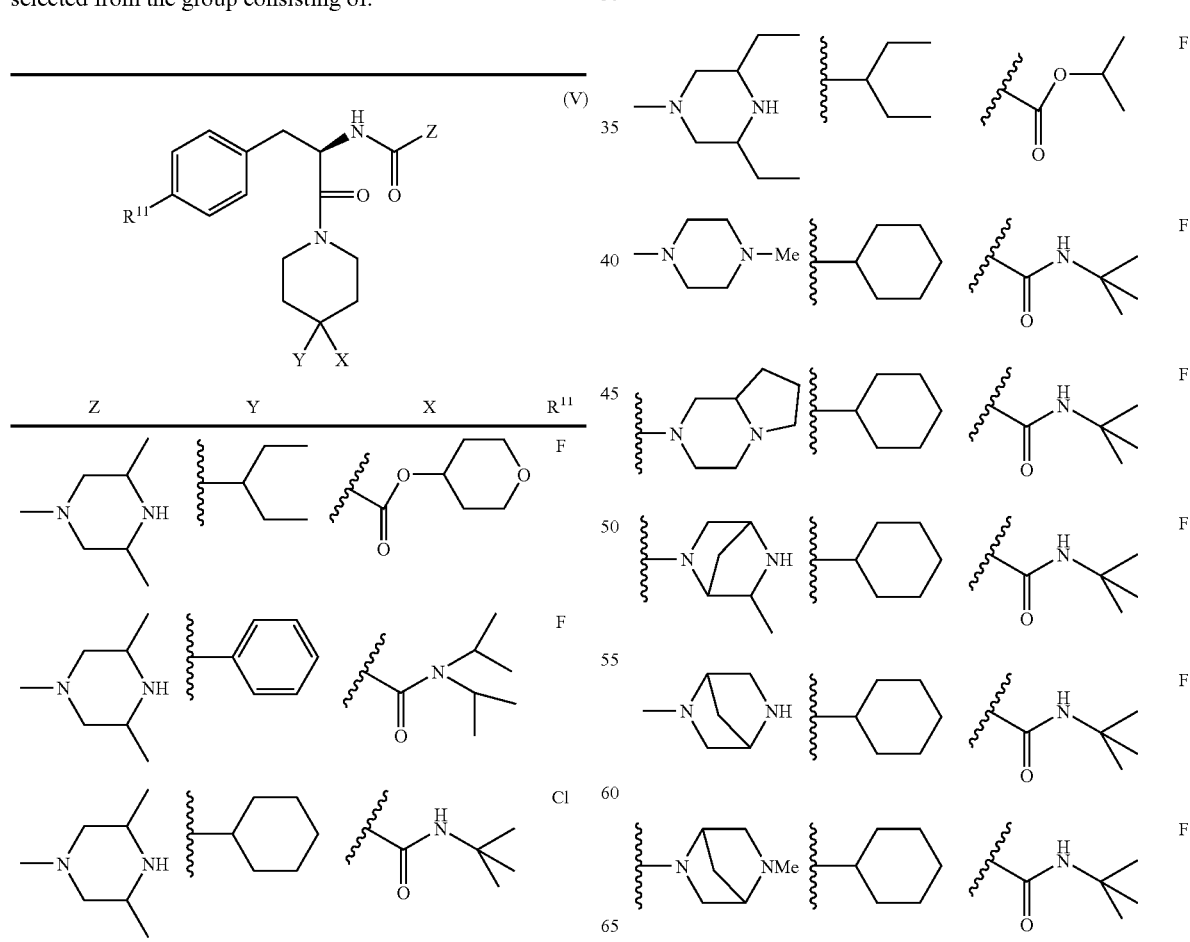

-continued
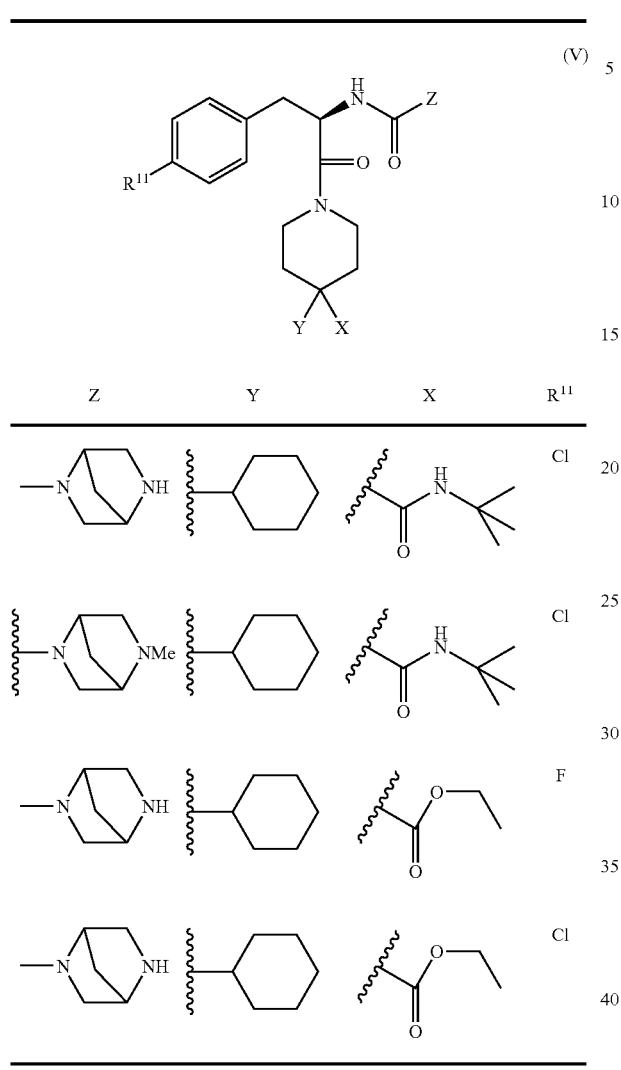
or a pharmaceutically acceptable salt thereof.
21. The compound of claim 15 selected from the group consisting of:
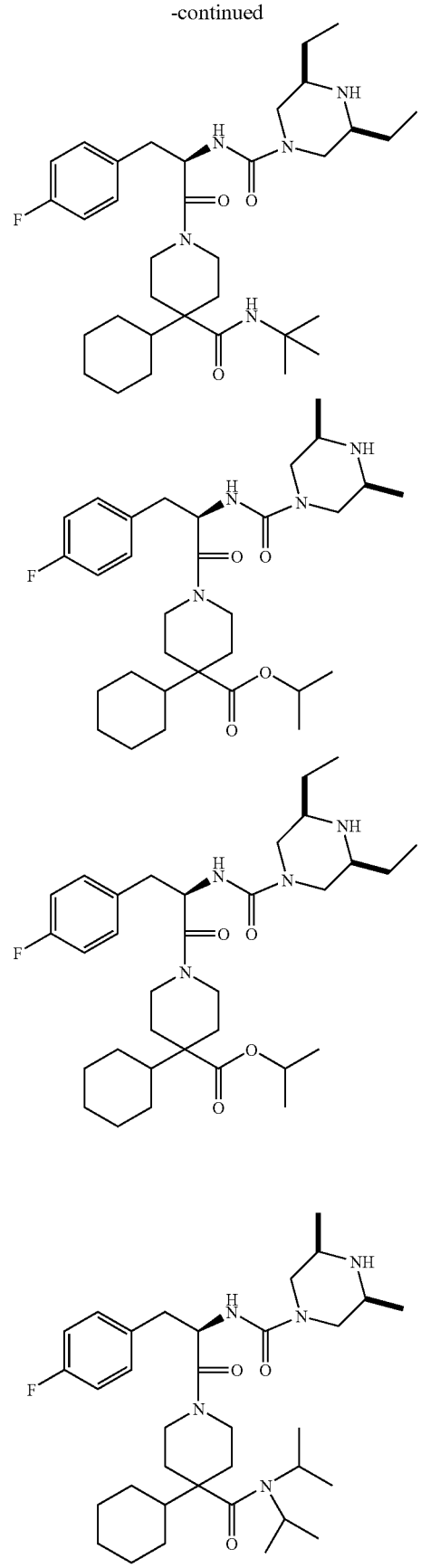

-continued

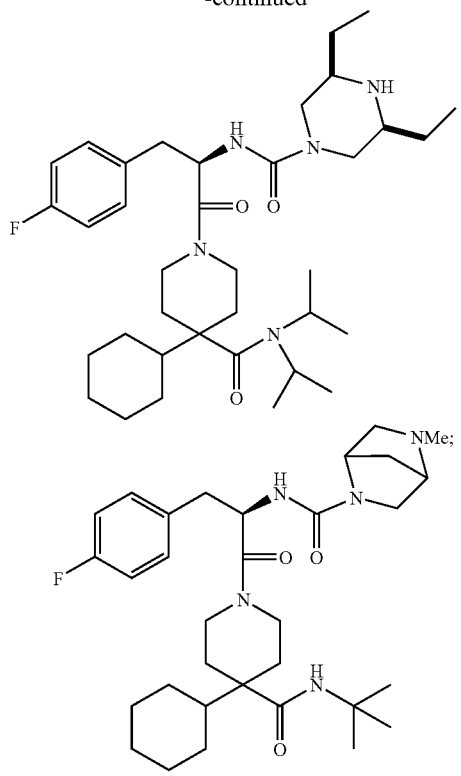

and or a pharmaceutically acceptable salt thereof.

22. A pharmaceutical composition which comprises a compound of claim 1 and a pharmaceutically acceptable carrier.

23. The compound of claim 21 which is:

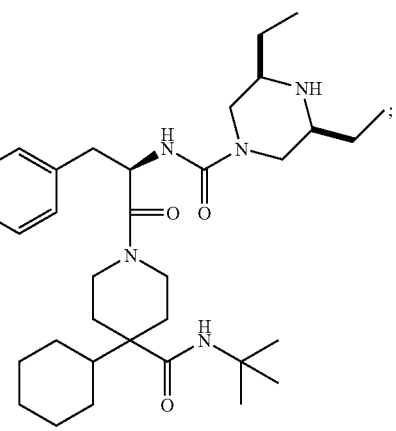

or a pharmaceutically acceptable salt thereof.

24. The compound of claim 21 wherein the pharmaceutically acceptable salt thereof is the hydrochloric acid salt.

25. The compound of claim 21 wherein the pharmaceutically acceptable salt thereof is the sulfuric acid salt.

26. The compound of claim 21 wherein the pharmaceutically acceptable salt thereof is the benzenesulfonic acid salt.

* * * * *